US008088387B2

(12) United States Patent
Steeves et al.

(10) Patent No.: US 8,088,387 B2
(45) Date of Patent: Jan. 3, 2012

(54) METHOD OF TARGETING SPECIFIC CELL POPULATIONS USING CELL-BINDING AGENT MAYTANSINOID CONJUGATES LINKED VIA A NON-CLEAVABLE LINKER, SAID CONJUGATES, AND METHODS OF MAKING SAID CONJUGATES

(75) Inventors: Rita M. Steeves, Stoneham, MA (US); Ravi V. J. Chari, Newton, MA (US); Walter A. Blättler, Brookline, MA (US)

(73) Assignee: Immunogen Inc., Waltham, MA (US)

( * ) Notice: Subject to any disclaimer, the term of this patent is extended or adjusted under 35 U.S.C. 154(b) by 1363 days.

(21) Appl. No.: 10/960,602

(22) Filed: Oct. 8, 2004

(65) Prior Publication Data

US 2005/0169933 A1 Aug. 4, 2005

Related U.S. Application Data

(60) Provisional application No. 60/509,901, filed on Oct. 10, 2003.

(51) Int. Cl.
*A61K 39/395* (2006.01)
(52) U.S. Cl. ............... 424/181.1; 424/179.1; 530/391.7; 530/391.9; 530/391.1
(58) Field of Classification Search .................. None
See application file for complete search history.

(56) References Cited

U.S. PATENT DOCUMENTS

| | | | |
|---|---|---|---|
| 4,137,230 A | 1/1979 | Hashimoto et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,424,219 A | 1/1984 | Hashimoto et al. | |
| 4,450,254 A | 5/1984 | Isley et al. | |
| 5,208,020 A * | 5/1993 | Chari et al. ............... 424/181.1 |
| 5,416,064 A * | 5/1995 | Chari et al. ............... 514/229.5 |
| 6,333,410 B1 | 12/2001 | Chari et al. | |
| 6,441,163 B1 | 8/2002 | Chari et al. | |
| 6,531,131 B1 | 3/2003 | Gu et al. | |
| 7,097,840 B2 | 8/2006 | Erickson et al. | |
| 7,754,211 B2 | 7/2010 | Rosenblum et al. | |
| 2004/0241174 A1 * | 12/2004 | Amphlett et al. ........... 424/178.1 |

FOREIGN PATENT DOCUMENTS

| | | |
|---|---|---|
| AU | 2003/259913 A1 | 8/2003 |
| AU | 2003/247762 A1 | 1/2004 |
| EP | 0 425 235 A2 | 5/1991 |
| EP | 1 354 896 A1 | 10/2003 |
| JP | 3-161490 A | 7/1991 |
| JP | 2001-503760 A | 3/2001 |
| JP | 2003-501487 A | 1/2003 |
| WO | 98/20020 A2 | 5/1998 |
| WO | 00/76554 A1 | 12/2000 |
| WO | 01/00244 A2 | 1/2001 |
| WO | 0124763 A2 | 4/2001 |
| WO | 02/16429 A2 | 2/2002 |
| WO | 02057316 A1 | 7/2002 |
| WO | 02098883 A1 | 12/2002 |
| WO | 03/000113 A3 | 1/2003 |
| WO | 03/024392 A2 | 3/2003 |
| WO | 03/057163 A2 | 7/2003 |
| WO | 03/068956 A1 | 8/2003 |
| WO | 03/074081 A1 | 9/2003 |
| WO | 2004/005470 A2 | 1/2004 |
| WO | 2004/016225 A2 | 2/2004 |

OTHER PUBLICATIONS

Roguska et al. (Protein Engineering 1996; 9: 895-904).*
Roguska et al. (Protein Engineering 1996; 9: 895-904, of record).*
Queen et al. (PNAS 1989; 86: 10029-10033).*
Chari, et al. "Immunoconjugates Containing Novel Maytansinoids: Promising Anticancer Drugs", *Cancer Research 52*, 127-133, Jan. 1, 1992.
Liu, et al. "Eradication of large colon tumor xenografts by targeted delivery of maytansinoids", *Proc. Natl. Acad Sci. USA*, vol. 93, pp. 8618-8623, Aug. 1996, Medical Sciences.
Akiyoshi Kawai, et al., "Chemical Modification of Ansamitocins. III. Synthesis and Biological Effects of 3-Acyl Esters of Maytansinol," 1984, pp. 3441-3451, Chemical and Pharmaceutical Bulletin, vol. 32, No. 9.
Examiner's Report dated Aug. 21, 2009 issued in Australian Patent Application No. 2004282491.

(Continued)

*Primary Examiner* — Sheela J Huff
(74) *Attorney, Agent, or Firm* — Sughrue Mion, PLLC

(57) ABSTRACT

The present invention discloses a method for targeting maytansinoids to a selected cell population, the method comprising contacting a cell population or tissue suspected of containing the selected cell population with a cell-binding agent maytansinoid conjugate, wherein one or more maytansinoids is covalently linked to the cell-binding agent via a non-cleavable linker and the cell-binding agent binds to cells of the selected cell population.

143 Claims, 37 Drawing Sheets

OTHER PUBLICATIONS

Y. Arano, et al., "A newly designed radioimmuno-conjugate releasing a hippurate-like radiometal chelate for enhanced target/non-target radioactivity", Nuclear Medicine and Biology, vol. 2, No. 1, pp. 63-69, Jan. 1, 1994.

P. R. Hamann, "Monoclonal Antibody-Drug Conjugates", Expert Opinion on Therapeutic Patents, vol. 15, No. 9, pp. 1087-1103, Jan. 1, 2005.

L. Lam, et al., "Recent Advances in Drug-Antibody Immunoconjugates for the Treatment of Cancer", Drugs Of The Future, vol. 28, No. 9, pp. 905-910, Jan. 1, 2003.

Supplementary European Search Report dated Jul. 1, 2010, as issued in European Patent Application No. 04793896.4.

English translation of Japanese Office Action dated Jan. 4, 2011, as issued in Japanese Application No. 2006-533951.

English translation of Technical Report No. GLMR11/00004 received Apr. 6, 2011, as issued in Costa Rica Patent Application No. 8319.

Technical Report No. GLMR11/00004 received Apr. 6, 2011, as issued in Costa Rica Patent Application No. 8319.

Tolcher, Anthony W., et al., "Phase I Pharmacokinetic and Biologic Correlative Study of Mapatumumab, a Fully Human Monoclonal Antibody with Agonist Activity to Tumor Necrosis Factor-Related Apoptosis-Inducing Ligand Receptor-1", Journal of Clinical Oncology, vol. 25, No. 11, pp. 1390-1396, Apr. 10, 2007.

U.S. Appl. No. 60/488,447, filed Jul. 21, 2003, Gillian Payne, et al.

* cited by examiner

SMCC (Succinimidyl 4-(*N*-maleimidomethyl)cyclohexane-1-carboxylate)

DM1 (thiolated Maytansinoid)

Size Exclusion Chromatography for huC242-SMCC-DM1

Cytotoxicity of huC242-SMCC-DM1
vs. COLO 205 (+) and A375 (−)
Continuous Exposure Clonogenic Assay

→ A375

■ COLO 205
$IC_{50} = 5 \times 10^{-12}$ M

Cytotoxicity of huC242 conjugates vs. COLO 205 cells
24 Hour Exposure Clonogenic Assay --o-- huC242-SPP-DM1
—•— huC242-SMCC-DM1

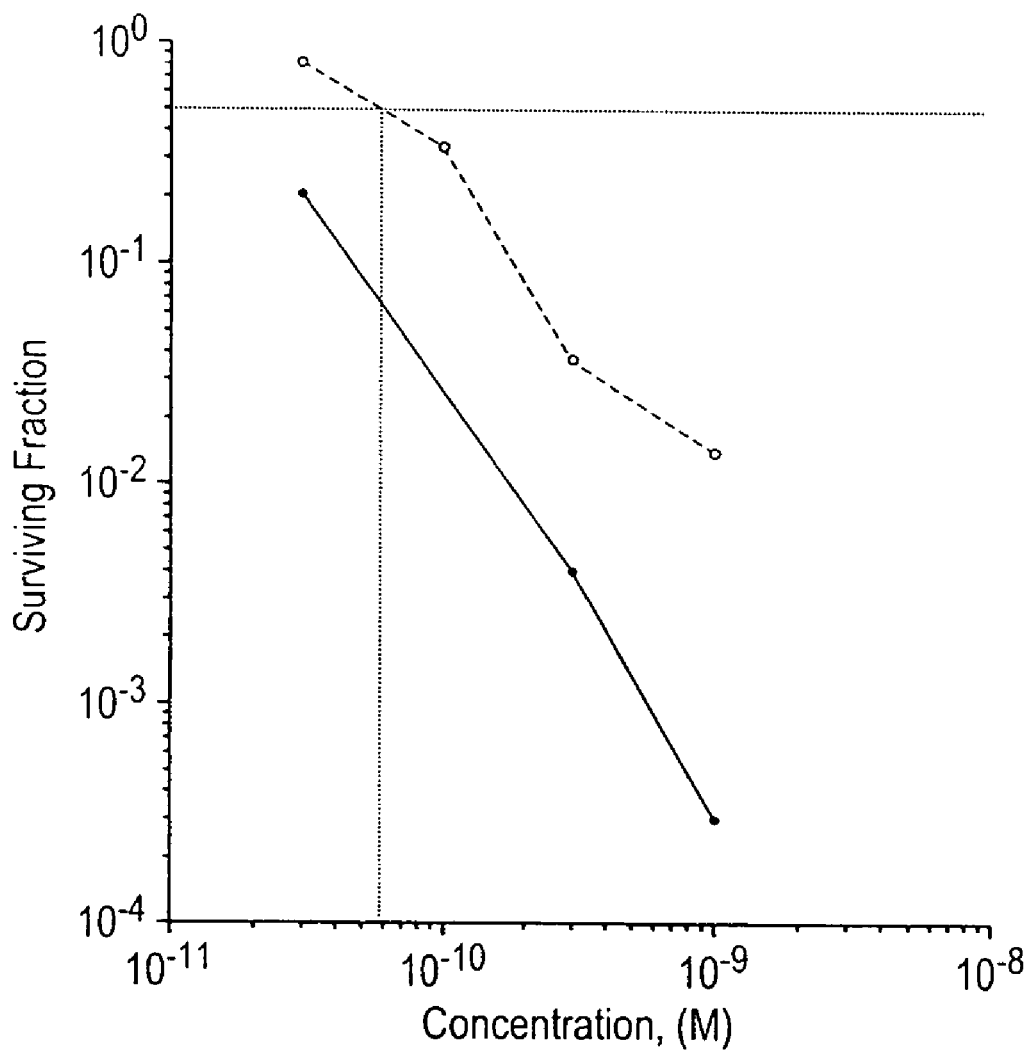

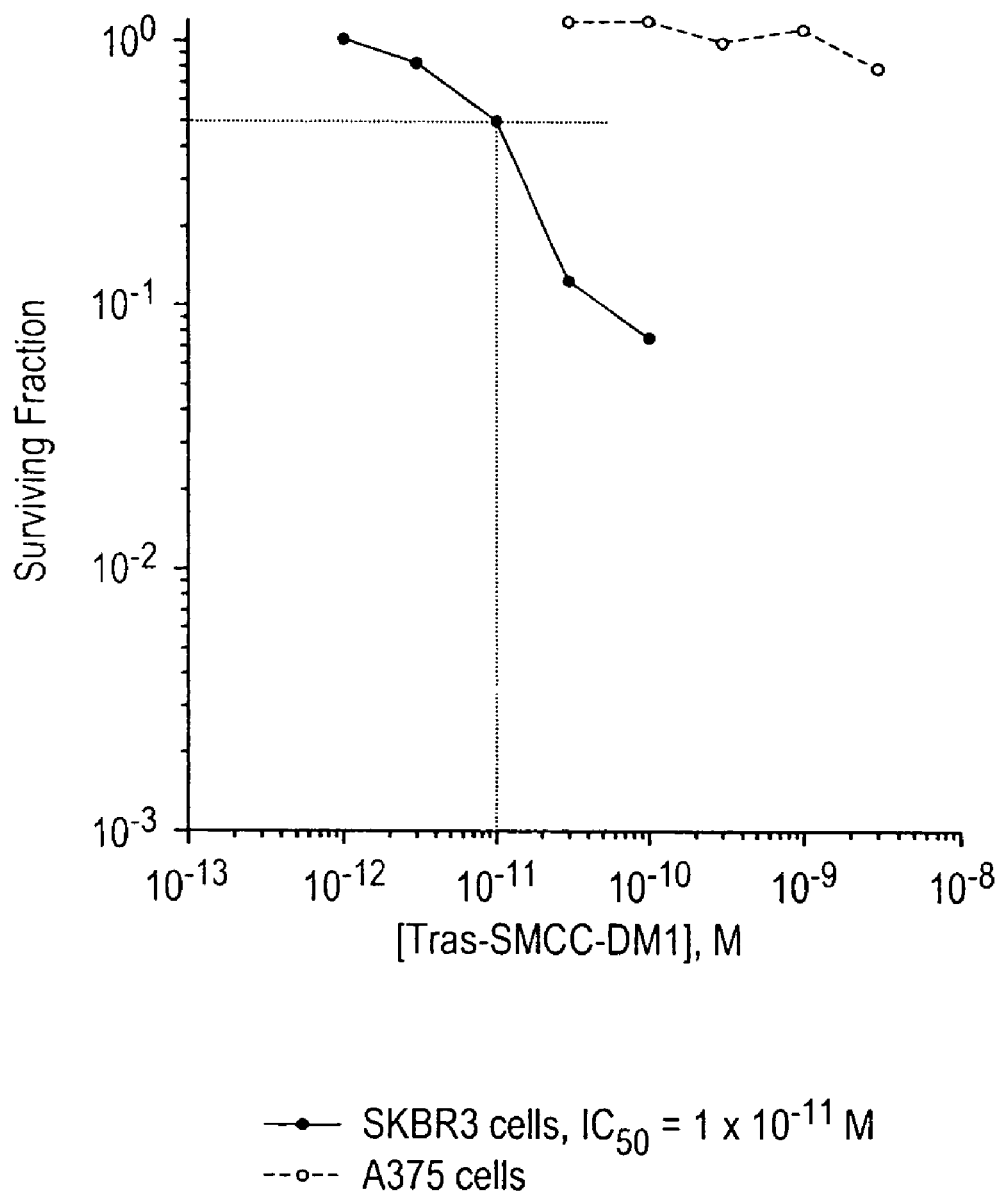

Potency evaluation of My9-6-SMCC-DM1, vs. THP-1 cells
Continuous Exposure Clonogenic Assay

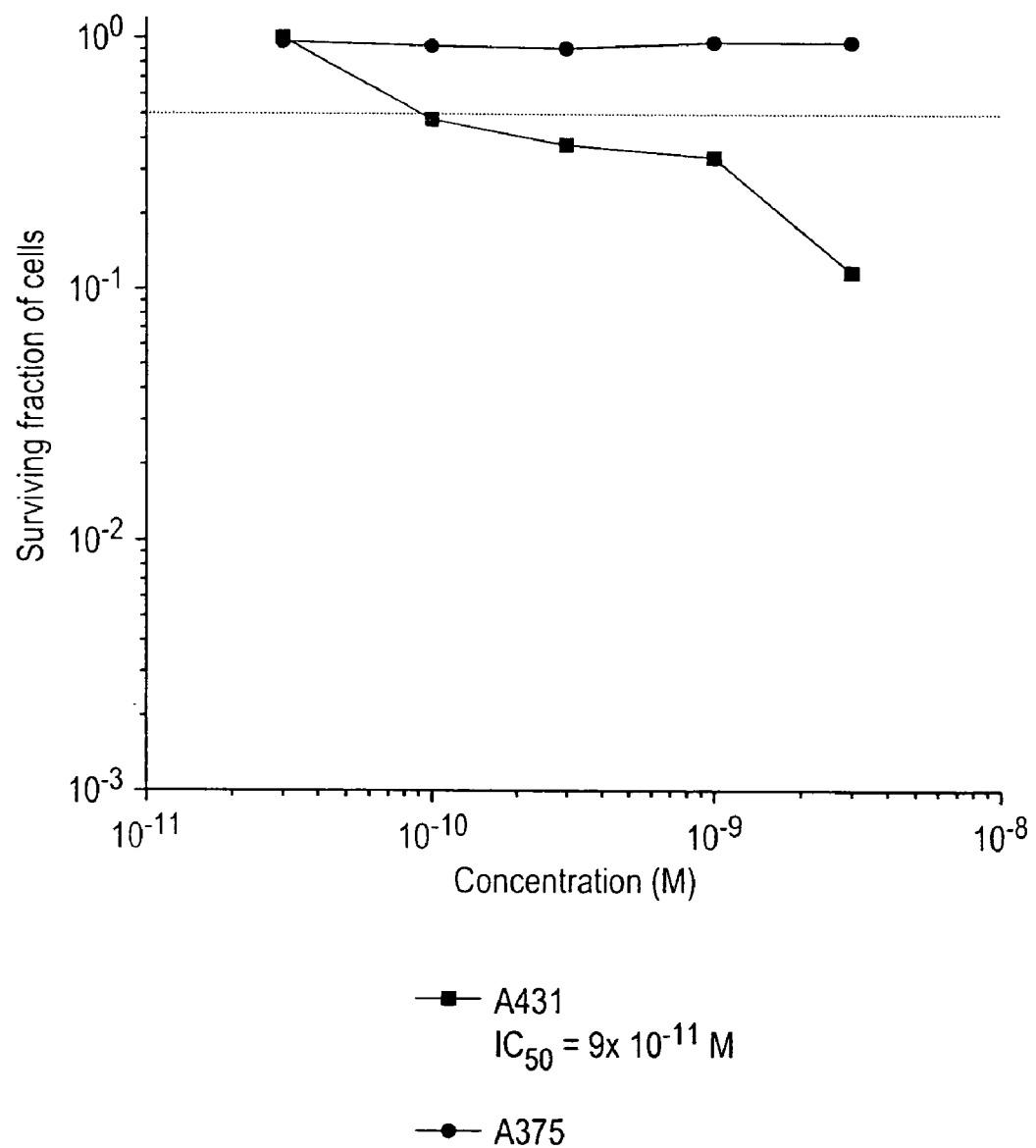

Cytotoxicity of N901-SMCC-DM1 conjugates vs. CHD-163 (+) and A431 (-) Continuous Exposure Clonogenic Assay

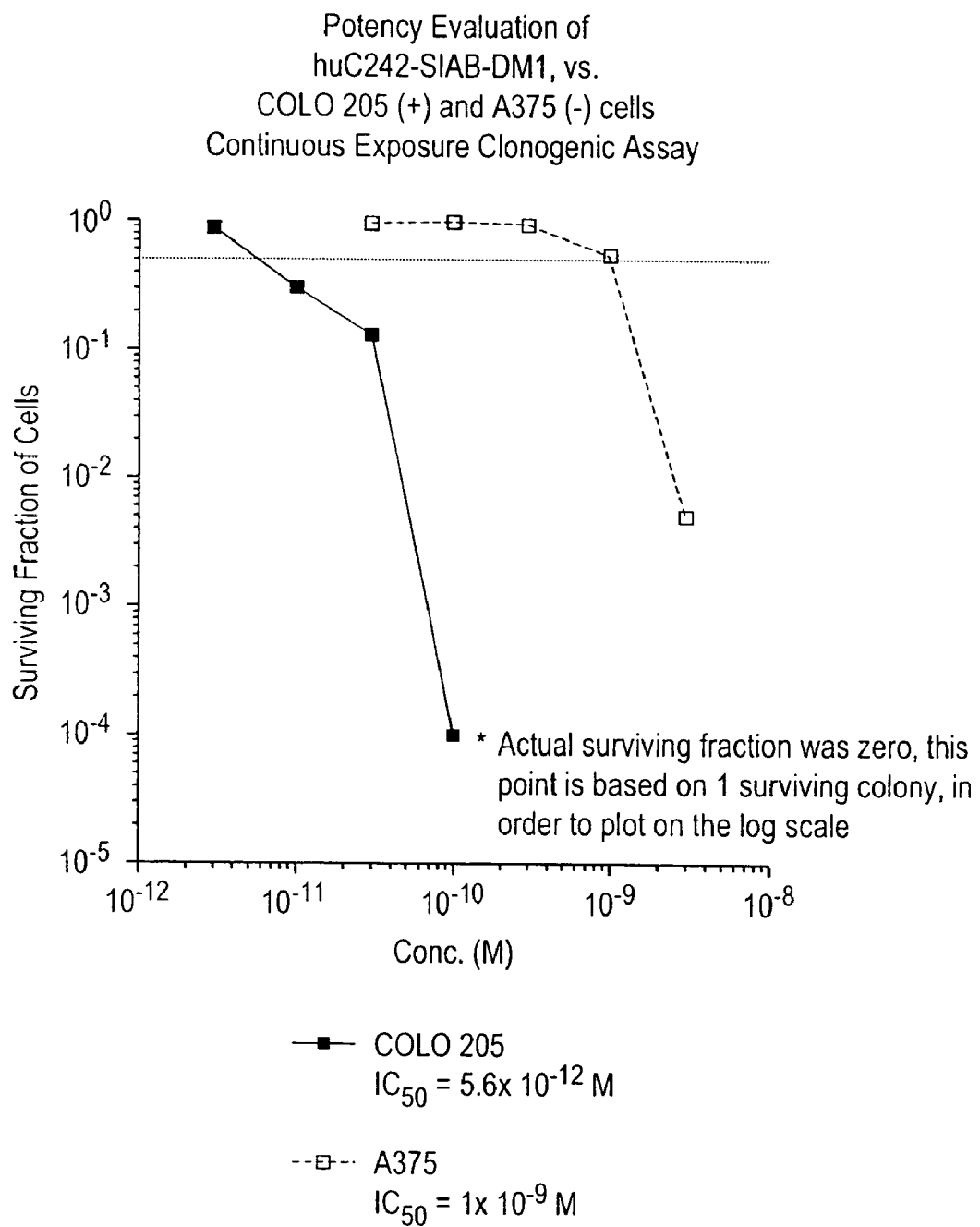

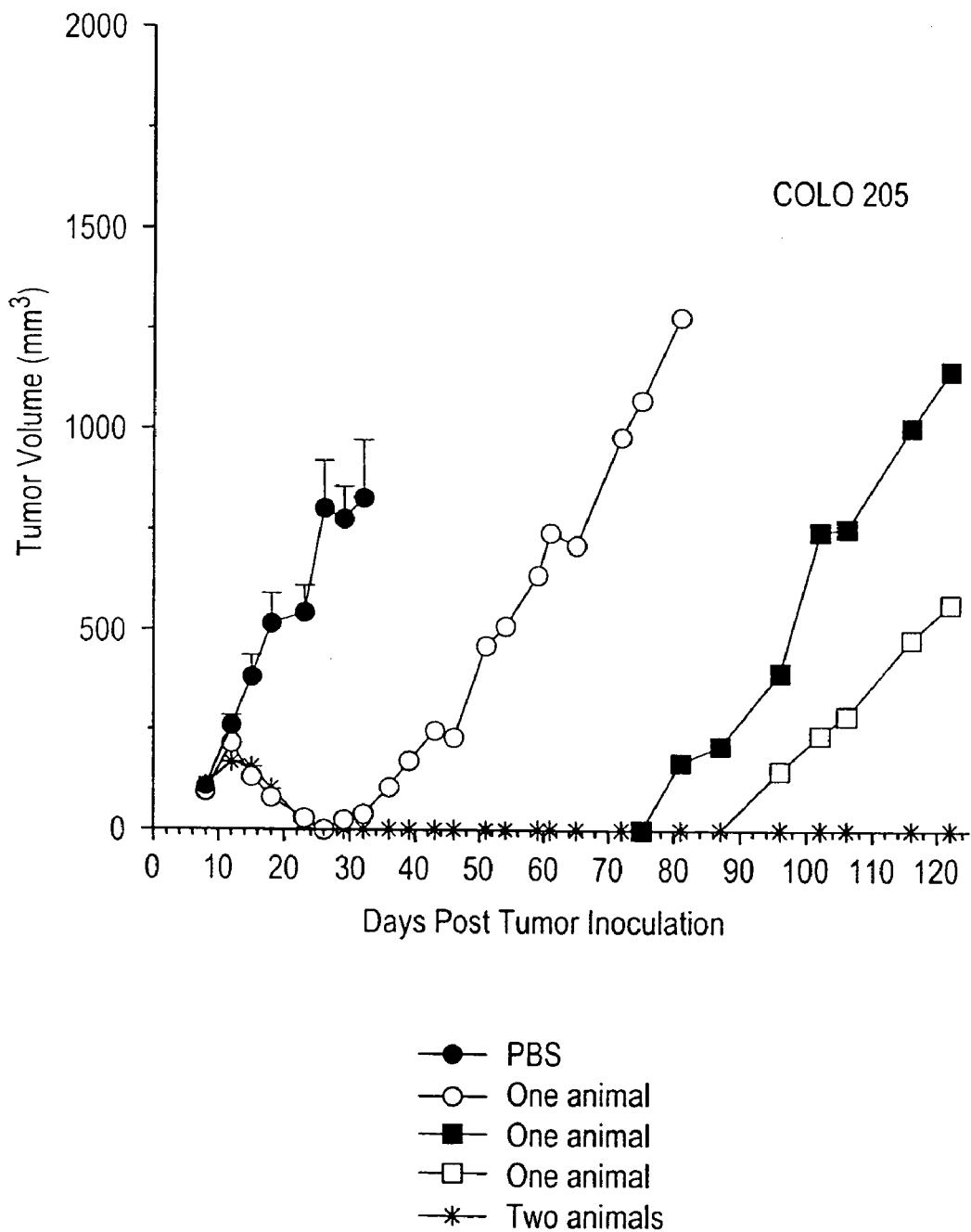

Anti-tumor activity of huC242-SMCC-DM1 against SNU 16 human gastric tumor xenografts in SCID mice

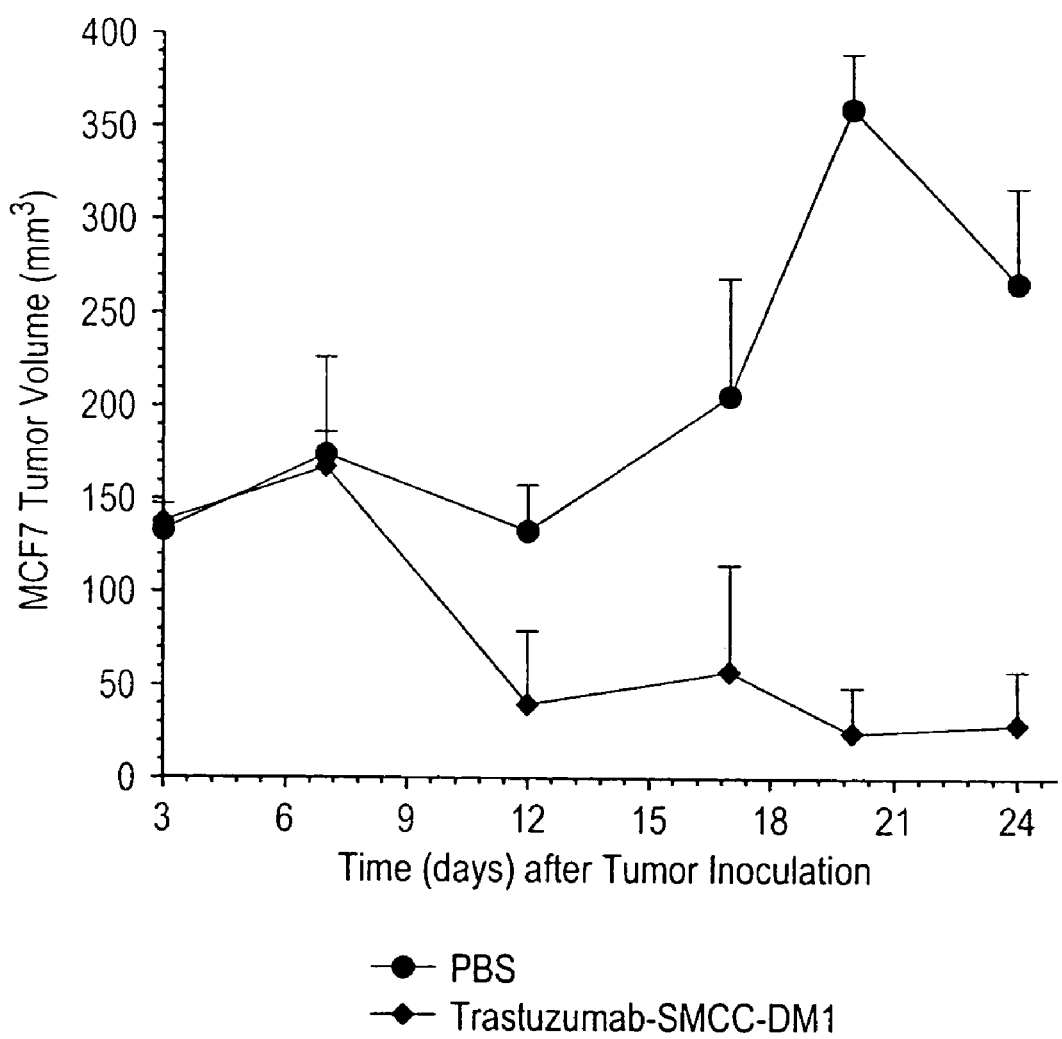

Survival of CD-1 Mice Treated with huC242-SPP-DM1

Survival of CD-1 Mice Treated with huC242-SMCC-DM1

Body Weight of CD-1 Mice Treated with huC242-SPP-DM1

Body Weight of CD-1 Mice Treated with huC242-SMCC-DM1 huC242-SPP-DM1 with COLO 205(Ag+) and Namalwa(Ag-) cells huC242-SMCC-DM1 with COLO 205(Ag+) and Namalwa(Ag-) cells Concentration of huC242 conjugates: $8 \times 10^{-10}$ M

FIG. 15
Representative structures of maleimido-based cross-linking agents
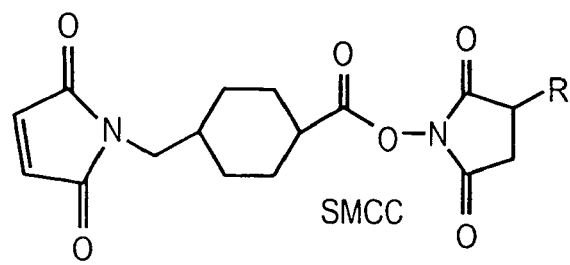
SMCC
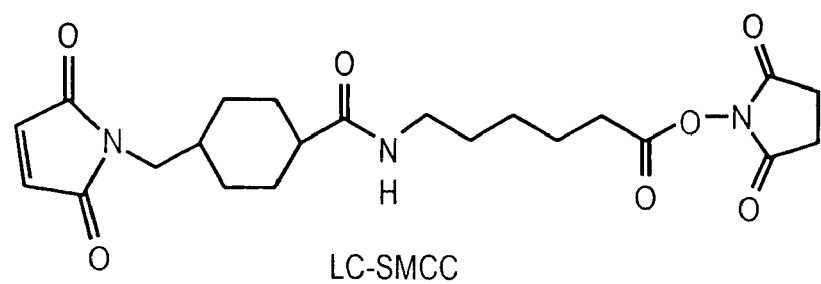
LC-SMCC
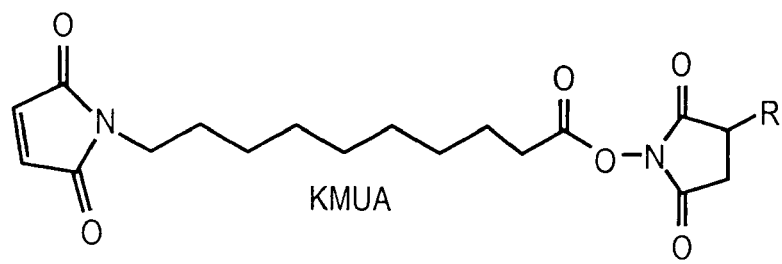
KMUA
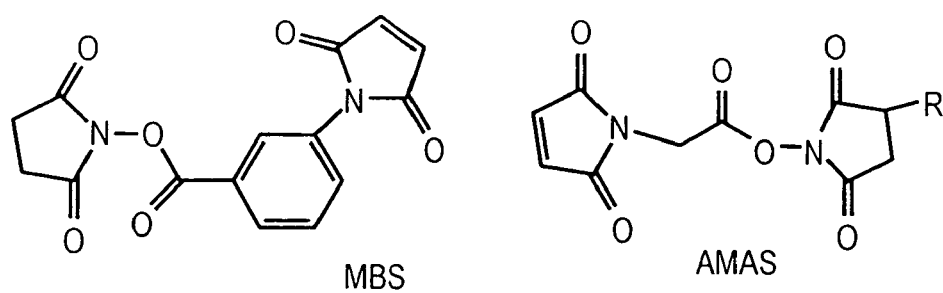
MBS        AMAS
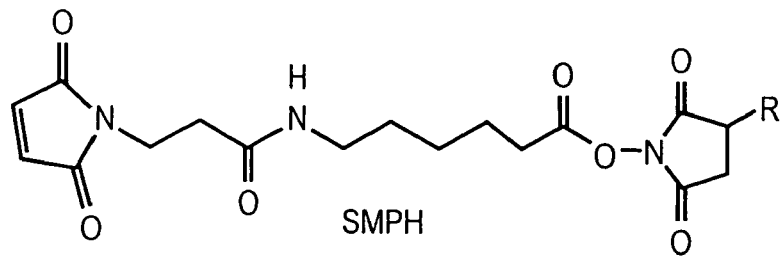
SMPH
In all cases R = H or SO$_3^-$

FIG. 16
Representative structures of haloacetyl-based cross-linking agents
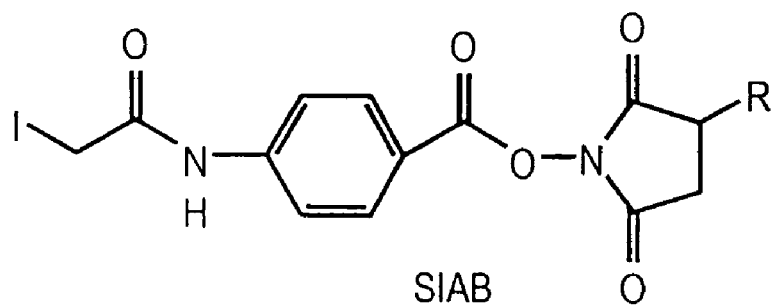
SIAB
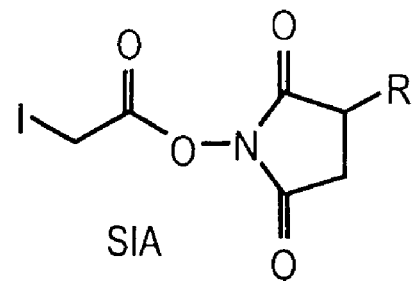
SIA
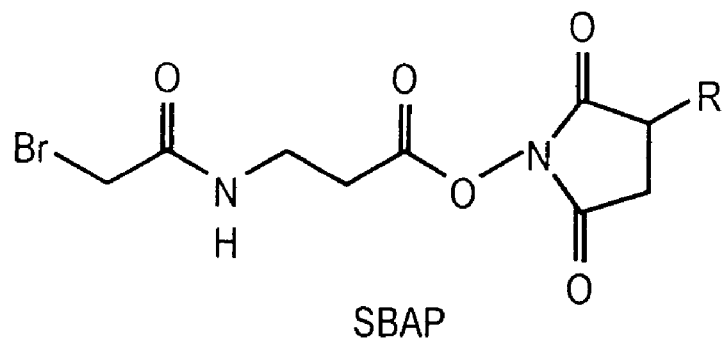
SBAP
In all cases R = H or $SO_3^-$

FIG. 17
Structure of DM1 and antibody-DM1 conjugates from maleimido-derivatized antibodies. As an example the SMCC cross-linking reagent was used.
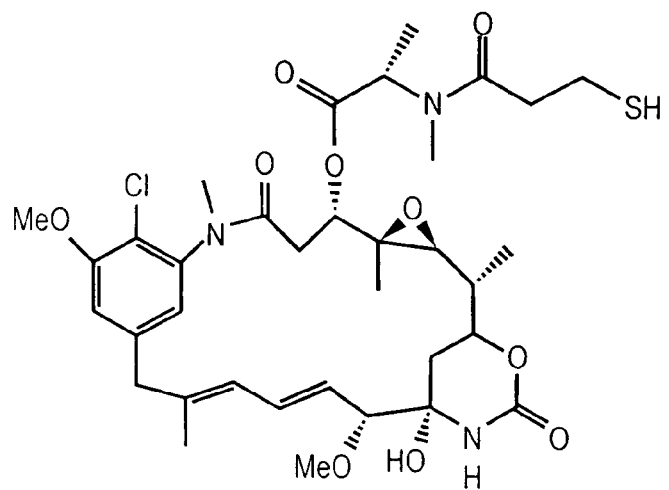
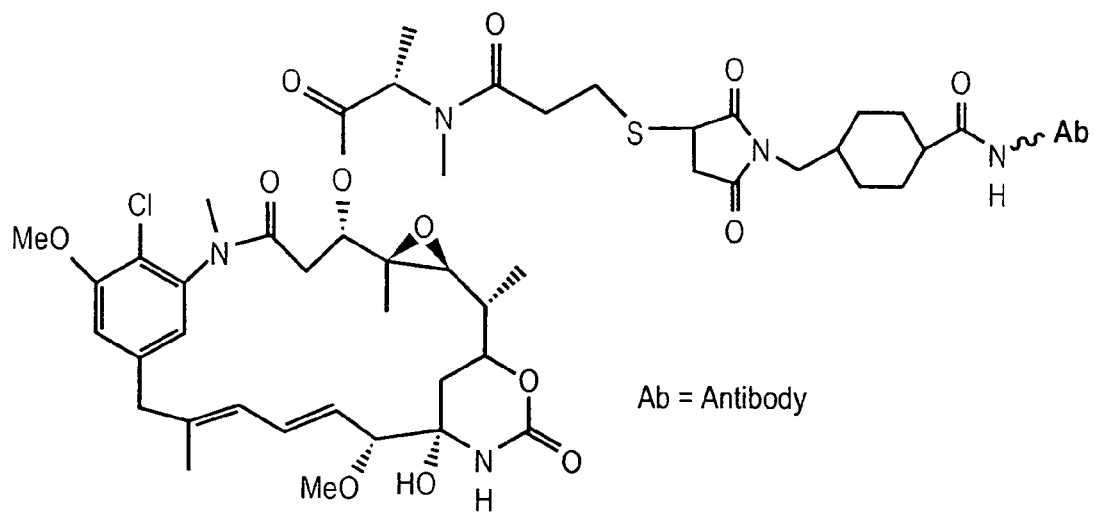
Ab = Antibody Structures of Antibody-DM1 conjugates from haloacetyl-derivatized antibodies. As an example the SIAB cross-linking reagent (top structure) and the SIA reagent (bottom structure) were used.

Ab = Antibody

FIG. 19
Structures of DM4 and antibody-DM4 conjugates derived from maleimido-derivatized antibodies. As an example the SMCC cross-linking reagent was used.
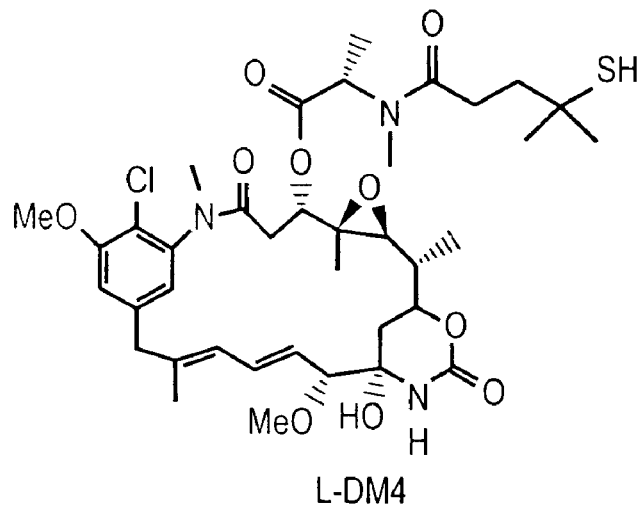
L-DM4
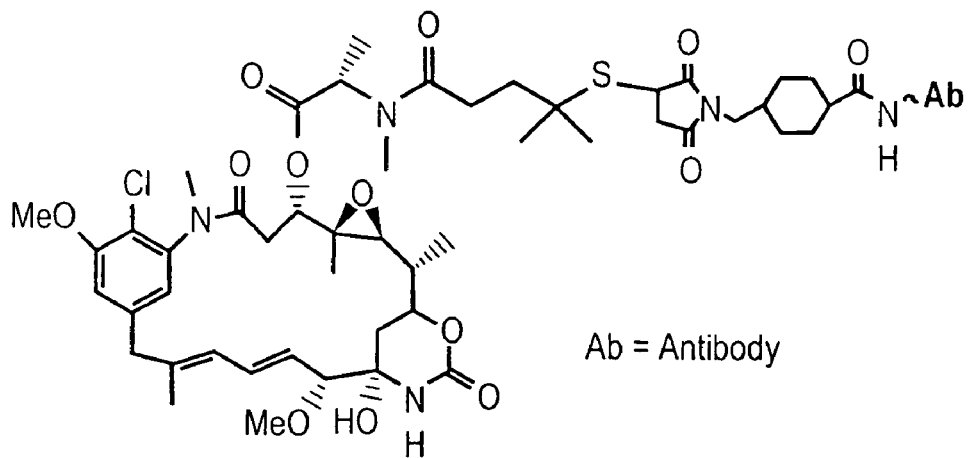
Ab = Antibody
Antibody-DM4 Conjugate Structures of Antibody-DM4 conjugates from haloacetyl-derivatized antibodies. As an example the SIAB cross-linking reagent (top structure) and the SIA reagent (bottom structure) were used.

Ab = Antibody

No Sulfur linker

CB = Cell binding agent

Cytotoxicity of HuC242-non-S-containing non-cleavable linker-DM1 and hC242-SMNP-DM3 vs. COLO 205 and A375 Cells
Continuous Exposure Clonogenic Assay — huC242-non-S-containing non cleavable linker – DM1 / COLO 205, $IC_{50}$ = 7.0 x $10^{-12}$ M — huC24-SMNP-DM3 / COLO 205, $IC_{50}$ = 1.3 x $10^{-11}$ M --○-- huC242-non-S-containing non cleavable linker – DM1 / A375, $IC_{50}$ > 3 x $10^{-9}$ M --□-- huC24-SMNP-DM3 / A 375, $IC_{50}$ > 3 x $10^{-9}$ M FACS binding assay of HuC242-non-S-containing non-cleavable linker-DM1 and huC242-SMNP-DM3 to COLO 205 cells ■— huC242
  $EC_{50} = 4.12 \times 10^{-10}$ M ▲— huC242 non-S-containing non-cleavable linker-DM1
  $EC_{50} = 7.04 \times 10^{-10}$ M ●— huC242-SMNP-DM3
  $EC_{50} = 7.08 \times 10^{-10}$ M Cytotoxicity of Trastuzumab-SMCC-DM1 vs. SK BR 3 and A 375 cells
Continuous Exposure Clonogenic Assay —•— SK BR 3 cells, $IC_{50}$ = 3.6 x $10^{-12}$M
--o-- A 375 cells, $IC_{50}$ > 3.0x$10^{-9}$ M Size Exclusion Chromatography for Trastuzumab-SMCC-DM1

Cytotoxicity of
Trastuzumab-SIAB-DM1
vs. SKBR3 and A 375 cells
Continuous Exposure
Clonogenic Assay —o— SKBR3 cells, $IC_{50} = 5.0 \times 10^{-12}$M
—•— A 375 cells, $IC_{50} > 3.0 \times 10^{-9}$M Size Exclusion Chromatography for Trastuzumab-SIAB-DM1

US 8,088,387 B2

METHOD OF TARGETING SPECIFIC CELL POPULATIONS USING CELL-BINDING AGENT MAYTANSINOID CONJUGATES LINKED VIA A NON-CLEAVABLE LINKER, SAID CONJUGATES, AND METHODS OF MAKING SAID CONJUGATES

This application claims benefit of Provisional U.S. Patent Application Ser. No. 60/509,901, filed Oct. 10, 2003, the entire disclosure of which is incorporated by reference.

FIELD OF THE INVENTION

A method consistent with the present invention relates to targeting specific cell populations using cell-binding agent maytansinoid conjugates linked via a non-cleavable linker. Another method consistent with the present invention is a method of making the conjugate. A composition consistent with the present invention relates to novel cell-binding agent maytansinoid conjugates where the maytansinoid is linked via a non-cleavable linker to the cell-binding agent. Another composition consistent with the present invention relates to novel maytansinoid esters.

BACKGROUND OF THE INVENTION

Maytansinoids are highly cytotoxic drugs. Maytansine was first isolated by Kupchan et al. from the east African shrub *Maytenus serrata* and shown to be 100- to 1000-fold more cytotoxic than conventional cancer chemotherapeutic agents like methotrexate, daunorubicin, and vincristine (U.S. Pat. No. 3,896,111). Subsequently, it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al., 21 J. Med. Chem. 31-37 (1978); Higashide et al. 270 Nature 721-722 (1977); Kawai et al., 32 Chem. Pharm. Bull. 3441-3451 (1984)). Examples of analogues of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4,5.

The naturally occurring and synthetic C-3 esters can be classified into two groups:
(a) C-3 esters with simple carboxylic acids (U.S. Pat. Nos. 4,248,870; 4,265,814; 4,308,268; 4,308,269; 4,309,428; 4,317,821; 4,322,348; and 4,331,598), and
(b) C-3 esters with derivatives of N-methyl-L-alanine (U.S. Pat. Nos. 4,137,230 and 4,260,608; and Kawai et al., 32 Chem. Pharm. Bull. 3441-3451 (1984)).

Esters of group (b) were found to be much more cytotoxic than esters of group (a).

Maytansine is a mitotic inhibitor. Treatment of L1210 cells in vivo with maytansine has been reported to result in 67% of the cells accumulating in mitosis. Untreated control cells were reported to demonstrate a mitotic index ranging from between 3.2 to 5.8% (Sieber et al., 43 Bibl. Haematol. 495-500 (1976)). Experiments with sea urchin eggs and clam eggs have suggested that maytansine inhibits mitosis by interfering with the formation of microtubules through the inhibition of the polymerization of the microtubule protein, tubulin (Remillard et al., 189 Science 1002-1005 (1975)).

In vitro, P388, L1210, and LY5178 murine leukemic cell suspensions have been found to be inhibited by maytansine at doses of $10^{-3}$ to $10^{-1}$ µg/ml with the P388 line being the most sensitive. Maytansine has also been shown to be an active inhibitor of in vitro growth of human nasopharyngeal carcinoma cells, and the human acute lymphoblastic leukemia line C.E.M. was reported inhibited by concentrations as low as $10^{-7}$ µg/ml (Wolpert-DeFillippes et al., 24 Biochem. Pharmacol. 1735-1738 (1975)).

Maytansine has also been shown to be active in vivo. Tumor growth in the P388 lymphocytic leukemia system was shown to be inhibited over a 50- to 100-fold dosage range, which suggested a high therapeutic index; also significant inhibitory activity could be demonstrated with the L1210 mouse leukemia system, the human Lewis lung carcinoma system and the human B-16 melanocarcinoma system (Kupchan, 33 Ped. Proc 2288-2295 (1974)).

Because the maytansinoids are highly cytotoxic, they were expected to be of use in the treatment of many diseases such as cancer. This expectation has yet to be realized. Clinical trials with maytansine were not favorable due to a number of side effects (Issel et al., 5 Cancer Treat. Rev. 199-207 (1978)). Adverse effects to the central nervous system and gastrointestinal symptoms were responsible for some patients refusing further therapy (Issel at 204), and it appeared that maytansine was associated with peripheral neuropathy that might be cumulative (Issel at 207).

Accordingly, targeting techniques to selectively deliver drugs to the target cell were employed. Both cleavable and non-cleavable linkers have been investigated for several drugs, but in most cases, including the case of maytansinoids, in vitro cytotoxicity tests have revealed that antibody-drug conjugates rarely achieve the same cytotoxic potency as the free unconjugated drugs. Thus, it has been generally accepted that for targeted delivery of maytansinoids to be effective, the linkage between the maytansinoid and the cell-binding agent must be cleavable.

Furthermore, in the area of immunotoxins, conjugates containing linkers with disulfide bridges between monoclonal antibodies and catalytically active protein toxins were shown to be more cytotoxic than conjugates containing other linkers. See, Lambert et al., 260 J. Biol. Chem. 12035-12041 (1985); Lambert et al., in Immunotoxins 175-209 (A. Frankel, ed. 1988), and Ghetie et al., 48 Cancer Res. 2610-2617 (1988). This was attributed to the high intracellular concentration of glutathione contributing to the efficient cleavage of the disulfide bond between an antibody molecule and a toxin. More recently, a conjugate of maytansinoids linked to the anti-Her2 breast cancer antibody TA.1 via the non-cleavable linker SMCC was shown to be 200-fold less potent than a conjugate of maytansinoids linked to TA.1 via a linker having a cleavable disulfide bond (Chari et al., 52 Cancer Res. 127-133 (1992)).

Thus, cytotoxic conjugates linked via disulfide-containing cleavable linkers have been sought. Shen et al. described the conversion of methotrexate into a mercaptoethylamide derivative followed by conjugation with poly-D-lysine via a disulfide bond (260 J. Biol. Chem. 10905-10908 (1985)). Preparation of a conjugate of the trisulfide-containing toxic drug calicheamycin with an antibody was also described (Menendez et al., Fourth International Conference on Monoclonal Antibody Immunoconjugates for Cancer, San Diego, Abstract 81 (1989)).

U.S. Pat. Nos. 5,208,020 and 5,416,064, the entire disclosures of which are expressly incorporated herein by reference, disclose cytotoxic conjugates comprising cell-binding agents linked to specific maytansinoid derivatives via cleavable linkers, such as linkers containing disulfide groups, linkers containing acid-labile groups, linkers containing photo-labile groups, linkers containing peptidase-labile groups, and linkers containing esterase-labile groups U.S. Pat. No. 6,333,410 B1, the entire disclosure of which is expressly incorporated herein by reference, discloses a process for preparing and purifying thiol-containing maytansinoids for linking to cell-binding agents, and U.S. Pat. No. 6,441,163 B1, the entire disclosure of which is expressly incorporated herein by reference, discloses a one-step method for preparing cytotoxic conjugates of maytansinoids and cell-binding agents, wherein the linker is a disulfide-containing cleavable linker.

Furthermore, U.S. Pat. No. 5,208,020 teaches antibody-maytansinoid conjugates with non-cleavable linkers, wherein the linker comprises a maleimido group. However, the reference contains no experimental data demonstrating that such conjugates are effective to treat disease.

It has now been found, unexpectedly, that cytotoxic conjugates of maytansinoids and cell-binding agents linked via non-cleavable linkers are extremely potent, and in many cases have unexpected advantages over conjugates of maytansinoids and cell-binding agents with cleavable linkers.

SUMMARY OF THE INVENTION

Illustrative, non-limiting embodiments of the present invention described below overcome the above disadvantages and other disadvantages not described above. Also, the present invention is not required to overcome the disadvantages described above, and an illustrative, non-limiting embodiment of the present invention described below may not overcome any of the problems described above.

One aspect of the present invention is a method for targeting a maytansinoid to a selected cell population comprising contacting a cell population or tissue suspected of containing cells from said selected cell population with a cell-binding agent maytansinoid conjugate, wherein one or more maytansinoids is linked to the cell-binding agent via a non-cleavable linker.

Another aspect of the present invention is a method for treatment of tumors, autoimmune diseases, graft rejections, graft versus host disease, viral infections, parasite infections, and other diseases that can be treated by targeted therapy wherein the targeting agent is a cell-binding agent, said method comprising administering to a subject in need of treatment an effective amount of a cell-binding agent maytansinoid conjugate wherein one or more maytansinoids is linked to the cell-binding agent, or a pharmaceutically acceptable formulation or solvate of said conjugate.

Another aspect of the present invention is a cell-binding agent maytansinoid conjugate, wherein one or more maytansinoids is linked to a cell-binding agent via a non-cleavable linker.

Another aspect of the present invention is a composition comprising the above-described conjugate.

Another aspect of the present invention is a method of making the above-described conjugate.

Another aspect of the present invention is novel maytansinoid esters.

BRIEF DESCRIPTION OF THE DRAWINGS

FIGS. 6A-C and FIG. 7 show graphically the cytotoxicity of huC242-SMCC-DM1 compared to conjugates prepared with disulfide-containing linkers.

FIGS. 8A-D show graphically the cytotoxicity of SMCC-DM1 conjugates linked to various cell-binding agents.

FIG. 9 shows graphically the cytotoxicity of antibody-maytansinoid conjugate huC242-SIAB-DM1.

FIG. 10A shows graphically the antitumor activity of huC242-SMCC-DM1 against COLO205 human colon cancer xenografts in SCID mice.

FIG. 10C shows graphically the anti-tumor efficacy of trastuzumab-SMCC-DM1 against human MCF7 tumor xenografts in SCID mice.

FIG. 15 shows representative structures of maleimido-based cross-linking agents.

FIG. 16 shows representative structures of haloacetyl-based cross-linking agents.

FIG. 17 shows the structure of antibody-SMCC-DM1 conjugates.

FIG. 19 shows the structure of antibody-SMCC-DM4 conjugates.

DETAILED DESCRIPTION OF EXEMPLARY EMBODIMENTS OF THE INVENTION

Figure 1:
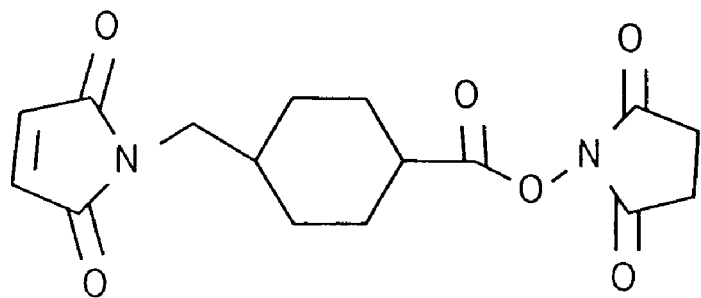
FIG. 1 shows the structure of SMCC.

The art reveals that it is extremely difficult to modify existing drugs without diminishing their cytotoxic potential. However, U.S. Pat. Nos. 6,441,163 B1, 6,333,410 B1, 5,416,064, and 5,208,020 demonstrate that potent cytotoxic agents can be created by linking maytansinoids to appropriate cell-binding agents via cleavable linkers, especially cleavable linkers containing disulfide groups. Cell-binding agent maytansinoid conjugates permit the full measure of the cytotoxic action of the maytansinoids to be applied in a targeted fashion against unwanted cells only, thereby avoiding side effects due to damage to non-targeted, healthy cells.

The present inventors have unexpectedly discovered that maytansinoids linked to cell-binding agents via non-cleavable linkers are superior in several important respects to maytansinoids linked via cleavable linkers. In particular, when compared to conjugates containing cleavable linkers, conjugates with non-cleavable linkers show equivalent antitumor activity both in vitro and in vivo, but demonstrate a marked decrease in plasma clearance rate and in toxicity.

Thus, this invention provides an improved method for targeting cells, especially cells that are to be destroyed, such as tumor cells (particularly solid tumor cells), virus infected cells, microorganism infected cells, parasite infected cells, autoimmune cells (cells that produce autoantibodies), activated cells (those involved in graft rejection or graft vs. host disease), or any other type of diseased or abnormal cells, while exhibiting a minimum of side effects.

The conjugate used in the inventive method has one or more maytansinoids linked to a cell-binding agent via a non-cleavable linker. In one method of making the conjugate, a cell-binding agent, for example an antibody, is first modified with a cross-linking reagent such as SMCC. In a second step, a reactive maytansinoid having a thiol group, such as DM1, is reacted with the modified antibody to produce antibody-maytansinoid conjugates. Alternatively, the maytansinoid can be modified with a cross-linking reagent before being reacted with a cell-binding agent. See, for example, U.S. Pat. No. 6,441,163 B1.

Suitable Maytansinoids

Maytansinoids suitable for use in the present invention are well known in the art, and can be isolated from natural sources according to known methods, produced using genetic engineering techniques (see Yu et al., 99 PNAS 7968-7973 (2002)), or prepared synthetically according to known methods.

Examples of suitable maytansinoids include maytansinol and maytansinol analogues. Examples of suitable maytansinol analogues include those having a modified aromatic ring and those having modifications at other positions.

Specific examples of suitable maytansinol analogues having a modified aromatic ring include:
  (1) C-19-dechloro (U.S. Pat. No. 4,256,746) (prepared by LAH reduction of ansamytocin P2);
  (2) C-20-hydroxy (or C-20-demethyl)±C-19-dechloro (U.S. Pat. Nos. 4,361,650 and 4,307,016) (prepared by demethylation using *Streptomyces* or *Actinomyces* or dechlorination using LAH); and
  (3) C-20-demethoxy, C-20-acyloxy (—OCOR), ±dechloro (U.S. Pat. No. 4,294,757) (prepared by acylation using acyl chlorides).

Specific examples of suitable maytansinol analogues having modifications of other positions include:
  (1) C-9-SH (U.S. Pat. No. 4,424,219) (prepared by the reaction of maytansinol with $H_2S$ or $P_2S_5$);
  (2) C-14-alkoxymethyl(demethoxy/$CH_2OR$)(U.S. Pat. No. 4,331,598);
  (3) C-14-hydroxymethyl or acyloxymethyl ($CH_2OH$ or $CH_2OAc$) (U.S. Pat. No. 4,450,254) (prepared from Nocardia);
  (4) C-15-hydroxy/acyloxy (U.S. Pat. No. 4,364,866) (prepared by the conversion of maytansinol by *Streptomyces*);
  (5) C-15-methoxy (U.S. Pat. Nos. 4,313,946 and 4,315,929) (isolated from Trewia nudlflora);
  (6) C-18-N-demethyl (U.S. Pat. Nos. 4,362,663 and 4,322,348) (prepared by the demethylation of maytansinol by *Streptomyces*); and
  (7) 4,5-deoxy (U.S. Pat. No. 4,371,533) (prepared by the titanium trichloride/LAH reduction of maytansinol).

Many positions on maytansinol are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable. However the C-3 position is preferred and the C-3 position of maytansinol is especially preferred.

According to the present invention, a preferred maytansinoid has a free thiol group. Particularly preferred maytansinoids comprising a free thiol group include N-methyl-alanine-containing esters and N-methyl-cysteine-containing esters of maytansinol are C-3 esters of maytansinol and its analogs. Preferred esters include N-methyl-alanine-containing esters and N-methyl-cysteine-containing esters of maytansinol. Synthesis of esters of maytansinol having a free thiol group has been previously described, for example in U.S. Pat. No. 5,208,020, Chari et al., 52 Cancer Res., 127-131 (1992), and Liu et al., 93 Proc Natl. Acad. Sci., 8618-8623 (1996). Furthermore, U.S. Pat. No. 6,333,410 B1, the entire disclosure of which is hereby incorporated by reference, provides an improved process for the preparation and purification of thiol-containing maytansinoids suitable for linking to cell-binding agents.

Many of the conjugates of the present invention exemplified below utilize the thiol-containing maytansinoid DM1, formally termed $N^{2'}$-deacetyl-$N^{2'}$-(3-mercapto-1-oxopropyl)-maytansine. DM1 is represented by the following structural formula:

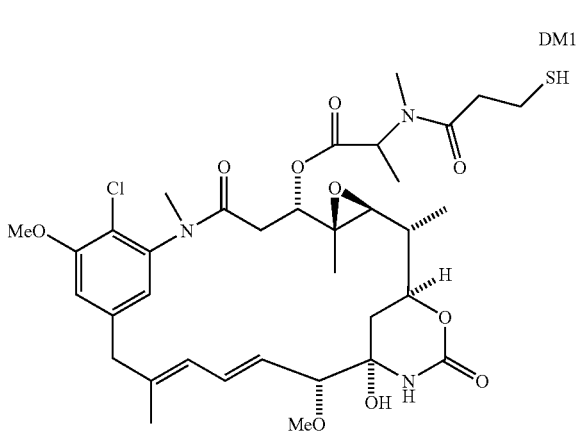

DM1

The synthesis of thiol-containing maytansinoid DM1 has been previously described (U.S. Pat. No. 5,208,020).

U.S. patent application Ser. No. 10/849,136, the entire disclosure of which is hereby incorporated by reference, describes sterically hindered thiol-containing maytansinoids that bear one or two alkyl substituents on the α-carbon bearing the thiol functionality. In addition, the acyl group of the acylated amino acid side chain of the maytansinoid bearing the sulfhydryl group possesses a linear chain length of at least three carbon atoms between the carbonyl group of the amide and the sulfur atom. These novel maytansinoids are suitable for use in the present invention.

The synthesis of maytansinoids having a sterically hindered thiol group can be described by reference to U.S. patent application Ser. No. 10/849,136, especially FIG. 3 therein.

In one aspect of the invention, the maytansinoid contains a sterically hindered thiol group and is represented by formula (II'-L), (II'-D), or (II'-D,L):

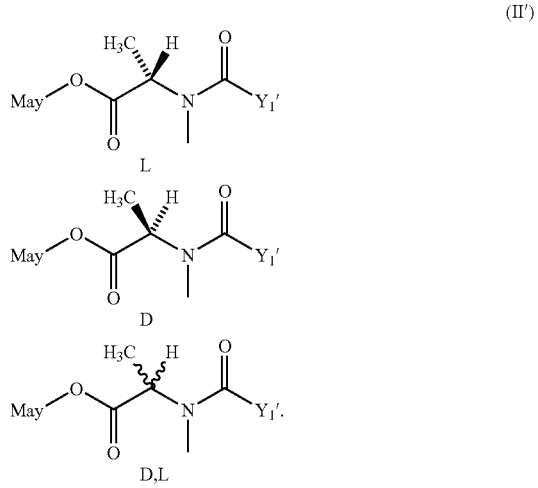

In the formula (II'),
$Y_1'$ represents
$(CR_7R_8)_l(CR_9\!\!=\!\!CR_{10})_p(C\!\!\equiv\!\!C)_qA_o(CR_5R_6)_mD_u(CR_{11}\!\!=\!\!CR_{12})_r(C\!\!\equiv\!\!C)_sB_t(CR_3R_4)_nCR_1R_2SH$.

A, B, and D, each independently is cyclic alkyl or cyclic alkenyl having 3 to 10 carbon atoms, simple or substituted aryl, or heterocyclic aromatic or heterocycloalkyl radical.

$R_1$ to $R_{12}$ are each independently linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition, $R_2$ to $R_{12}$ can be H.

l, m, n, o, p, q, r, s, t, and u are each independently 0 or an integer of from 1 to 5, provided that at least two of l, m, n, o, p, q, r, s, t and u are not both zero.

May represents a maytansinoid that bears a side chain at C-3 hydroxyl, C-14 hydroxymethyl, C-15 hydroxyl or C-20 desmethyl.

Another maytansinoid useful in the invention is represented by formula (II-L), (II-D), or (II-D,L):

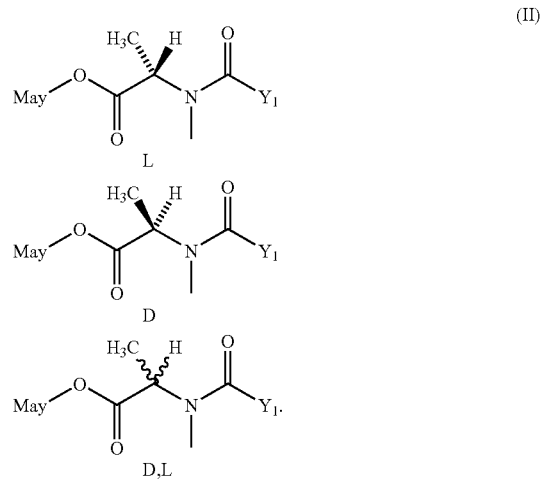

In the formula (II),
$Y_1$ represents $(CR_7R_8)_l(CR_5R_6)_m(CR_3R_4)_nCR_1R_2SH$.

$R_1$ to $R_8$ are each independently linear alkyl or alkenyl having 1 to 10 carbon atoms, branched or cyclic alkyl or alkenyl having 3 to 10 carbon atoms, phenyl, substituted phenyl, heterocyclic aromatic or heterocycloalkyl radical, and in addition $R_2$ to $R_8$ can be H.

l, m and n are each independently an integer of from 1 to 5, and in addition n can be 0.

May represents a maytansinol that bears a side chain at C-3 hydroxyl, C-14 hydroxymethyl, C-15 hydroxyl or C-20 desmethyl.

Another useful maytansinoid is represented by formula $4_1'$:

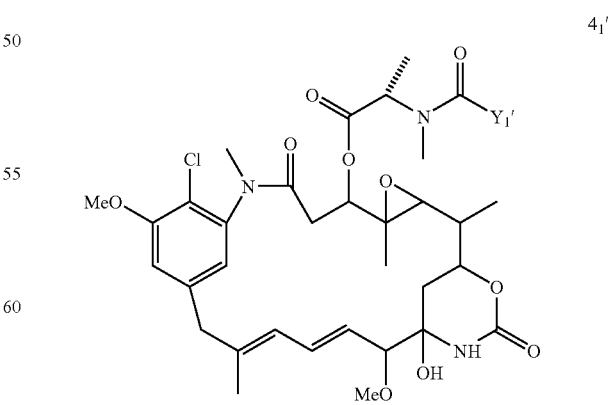

$4_1'$ wherein the substituents are as defined for formula (II') above.

Another useful maytansinoid is represented by formula $4_1$:

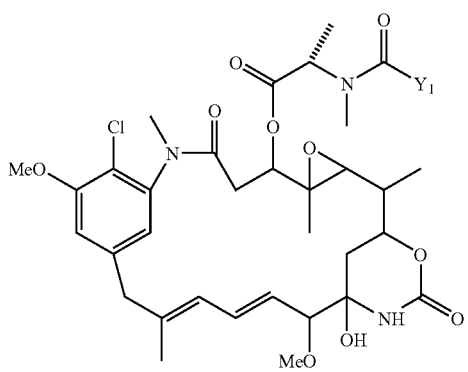

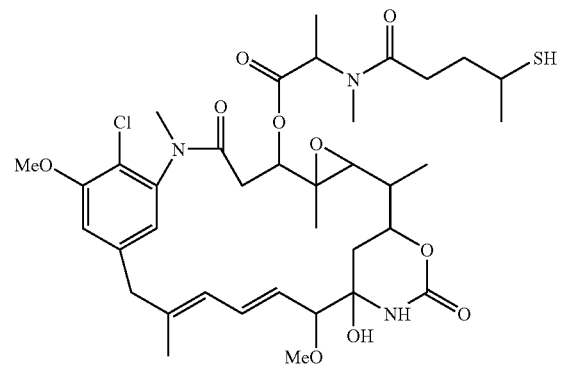

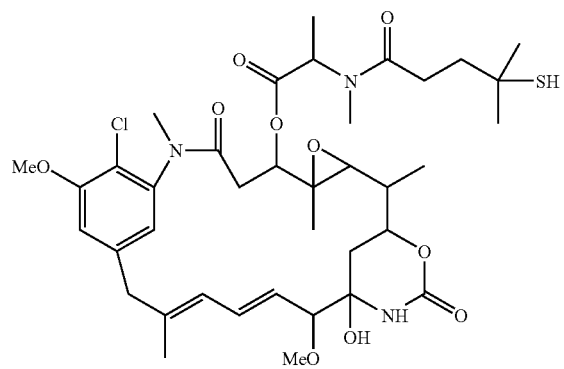

wherein the substituents are as defined for formula (II) above.

Preferred are any of the above-described compounds wherein $R_1$ is H and $R_2$ is methyl or $R_1$ and $R_2$ are methyl.

Especially preferred are any of the above-described compounds, wherein $R_1$ is H, $R_2$ is methyl, $R_5$, $R_6$, $R_7$ and $R_8$ are each H, l and m are each 1, and n is 0; and those wherein $R_1$ and $R_2$ are methyl, $R_5$, $R_6$, $R_7$, $R_8$ are each H, l and m are 1, and n is 0.

Further, the L-aminoacyl stereoisomer is preferred.

Examples of linear alkyls or alkenyls having 1 to 10 carbon atoms include, but are not limited to, methyl, ethyl, propyl, butyl, pentyl, hexyl, propenyl, butenyl and hexenyl.

Examples of branched alkyls or alkenyls having 3 to 10 carbon atoms include, but are not limited to, isopropyl, isobutyl, sec.-butyl, tert-butyl, isopentyl, 1-ethyl-propyl, isobutenyl and isopentenyl.

Examples of cyclic alkyls or alkenyls having from 3 to 10 carbon atoms include, but are not limited to, cyclopropyl, cyclobutyl, cyclopentyl, cyclohexyl, cyclopentenyl, and cyclohexenyl.

Simple aryls include aryls having 6 to 10 carbon atoms, and substituted aryls include aryls having 6 to 10 carbon atoms bearing at least one alkyl substituent containing from 1 to 4 carbon atoms, or alkoxy substituent such as methoxy, ethoxy, or a halogen substituent or a nitro substituent.

Examples of simple aryl that contain 6 to 10 carbon atoms include, but are not limited to, phenyl and naphthyl.

Examples of substituted aryl include, but are not limited to, nitrophenyl, dinitrophenyl.

Heterocyclic aromatic radicals include groups that have a 3 to 10-membered ring containing one or two heteroatoms selected from N, O or S.

Examples of heterocyclic aromatic radicals include, but are not limited to, pyridyl, nitro-pyridyl, pyrollyl, oxazolyl, thienyl, thiazolyl, and furyl.

Heterocycloalkyl radicals include cyclic compounds, comprising 3 to 10-membered ring systems, containing one or two heteroatoms, selected form N, O or S.

Examples of heterocycloalkyl radicals include, but are not limited to, dihydrofuryl, tetrahydrofuryl, pyrrolidinyl, piperidinyl, piperazinyl, and morpholino.

Particularly preferred maytansinoids comprising a side chain that contains a sterically hindered thiol bond are maytansinoids $N^{2'}$-deacetyl-N-$^{2'}$(4-mercapto-1-oxopentyl)-maytansine (termed DM3) and $N^{2'}$-deacetyl-$N^{2'}$-(4-methyl-4-mercapto-1-oxopentyl)-maytansine (termed DM4). DM3 and DM4 are represented by the following structural formulae:

Cell-Binding Agents

The effectiveness of the compounds of the invention as therapeutic agents depends on the careful selection of an appropriate cell-binding agent. Cell-binding agents may be of any kind presently known, or that become known and include peptides and non-peptides. Generally, these can be antibodies (especially monoclonal antibodies), lymphokines, hormones, growth factors, vitamins, nutrient-transport molecules (such as transferrin), or any other cell-binding molecule or substance that specifically binds a target.

More specific examples of cell-binding agents that can be used include:
polyclonal and monoclonal antibodies, including fully human antibodies;
single chain antibodies (polyclonal and monoclonal);
fragments of antibodies (polyclonal and monoclonal) such as Fab, Fab', F(ab')$_2$, and Fv (Parham, 131 J. Immunol. 2895-2902 (1983); Spring et al., 113 J. Immunol. 470-478 (1974); Nisonoff et al., 89 Arch. Biochem. Biophys. 230-244 (1960));
chimeric antibodies and antigen-binding fragments thereof;
domain antibodies (dAbs) and antigen-binding fragments thereof, including camelid antibodies (Desmyter et al., 3 Nature Struct. Biol, 752, 1996);
shark antibodies called new antigen receptors (IgNAR) (Greenberg et al., 374 Nature, 168, 1995; Stanfield et al. 305 Science 1770-1773, 2004);
interferons (e.g. alpha, beta, gamma);
lymphokines such as IL-2, IL-3, IL-4, IL-6;
hormones such as insulin, TRH (thyrotropin releasing hormone), MSH (melanocyte-stimulating hormone), steroid hormones, such as androgens and estrogens;

growth factors and colony-stimulating factors such as EGF, TGF-alpha, FGF, VEGF, G-CSF, M-CSF and GM-CSF (Burgess, 5 Immunology Today 155-158 (1984));

transferrin (O'Keefe et al., 260 J. Biol. Chem. 932-937 (1985)); and vitamins, such as folate.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969, 108; McCafferty et al., WO 92/01047; Liming et al., WO 99/06587). In addition, resurfaced antibodies disclosed in U.S. Pat. No. 5,639,641 may also be used, as may humanized antibodies.

Selection of the appropriate cell-binding agent is a matter of choice that depends upon the particular cell population that is to be targeted, but in general human monoclonal antibodies are preferred if an appropriate one is available.

For example, the monoclonal antibody J5 is a murine IgG2a antibody that is specific for Common Acute Lymphoblastic Leukemia Antigen (CALLA) (Ritz et al, 283 Nature 583-585 (1980)) and can be used if the target cells express CALLA such as in the disease of acute lymphoblastic leukemia.

The monoclonal antibody MY9 is a murine $IgG_1$ antibody that binds specifically to the CD33 antigen (J. D. Griffin et al 8 Leukemia Res., 521-(1984)) and can be used if the target cells express CD33 as in the disease of acute myelogenous leukemia (AML).

Similarly, the monoclonal antibody anti-B4 interchangeably also called B4, is a murine $IgG_1$ that binds to the CD19 antigen on B cells (Nadler et al, 131 J. Immunol. 244-250 (1983)) and can be used if the target cells are B cells or diseased cells that express this antigen such as in non-Hodgkin's lymphoma or chronic lymphoblastic leukemia.

In addition, the monoclonal antibody C242 that binds to the CanAg antigen (U.S. Pat. No. 5,552,293) can be used to treat CanAg expressing tumors, such as colorectal, pancreatic, non-small cell lung, and gastric cancers. HuC242 is a humanized form of the monoclonal antibody C242 that is described in U.S. Pat. No. 5,552,293 and for which the hybridoma is deposited with the ECACC identification Number 90012601. A humanized form can be prepared by either applying the CDR-grafting methodology (U.S. Pat. Nos. 5,585,089; 5,693, 761; and 5,693,762) or the resurfacing methodology (U.S. Pat. No. 5,639,641). HuC242 can also be used to treat CanAg expressing tumors, such as colorectal, pancreatic, non-small cell lung, and gastric cancers.

Further, the antibody trastuzumab can be used to treat breast and other cancers, such as prostate and ovarian cancers that express the Her2 antigen.

Anti-IGF-IR antibodies that bind to insulin growth factor receptor are also useful.

Ovarian cancer and prostate cancer can be successfully targeted with, for example, an anti-MUC1 antibody, such as anti-HMFG-2 (Taylor-Papadimitriou et al., 28. Int. J. Cancer 17-21, 1981) or hCTM01 (56 Cancer Res. 5179-5185, 1996) and an anti-PSMA (prostate-specific membrane antigen), such as J591 (Liu et al. 57 Cancer Res. 3629-3634, 1997) respectively.

Non-antibody molecules can also be used to target specific cell populations. For example, GM-CSF, which binds to myeloid cells, can be used as a cell-binding agent to target diseased cells from acute myelogenous leukemia. In addition, IL-2, which binds to activated T-cells, can be used for prevention of transplant graft rejection, for therapy and prevention of graft-versus-host disease, and for treatment of acute T-cell leukemia. MSH, which binds to melanocytes, can be used for the treatment of melanoma. Folic acid can be used to target the folate receptor expressed on ovarian and other tumors. Epidermal growth factor (EGF) can be used to target squamous cancers such as lung and head and neck. Somatostatin can be used to target neuroblastomas and other tumor types. Cancers of the breast and testes can be successfully targeted with estrogen (or estrogen analogues) or androgen (or androgen analogues) respectively as cell-binding agents.

Cross-Linking Reagents

The maytansinoid is linked to the cell-binding agent by means of a cross-linking reagent that, when reacted, forms a non-cleavable linker between the maytansinoid and the cell-binding agent.

As used herein, a "linker" is any chemical moiety that links a cell-binding agent covalently to a maytansinoid. In some instances, part of the linker is provided by the maytansinoid. For example, DM1, a thiol-containing maytansinoid (FIG. 2), is a derivative of the natural maytansinoid, maytansine, and provides part of the linker. The side chain at the C-3 hydroxyl group of maytansine ends in —CO—$CH_3$, the side chain of DM1 ends in —CO—$CH_2$—$CH_2$—SH. Therefore the final linker is assembled from two pieces, the cross-linking reagent introduced into the cell-binding agent and the side chain from the DM1.

Cleavable linkers are linkers that can be cleaved under mild conditions, i.e. conditions under which the activity of the maytansinoid drug is not affected. Many known linkers fall in this category and are described below.

Disulfide containing linkers are linkers cleavable through disulfide exchange, which can occur under physiological conditions.

Acid-labile linkers are linkers cleavable at acid pH. For example, certain intracellular compartments, such as endosomes and lysosomes, have an acidic pH (pH 4-5), and provide conditions suitable to cleave acid-labile linkers.

Linkers that are photo-labile are useful at the body surface and in many body cavities that are accessible to light. Furthermore, infrared light can penetrate tissue.

Some linkers can be cleaved by peptidases. Only certain peptides are readily cleaved inside or outside cells, see e.g. Trouet et al., 79 Proc. Natl. Acad. Sci. USA, 626-629 (1982) and Umemoto et al. 43 Int. J. Cancer, 677-684 (1989). Furthermore, peptides are composed of α-amino acids and peptidic bonds, which chemically are amide bonds between the carboxylate of one amino acid and the α-amino group of a second amino acid. Other amide bonds, such as the bond between a carboxylate and the ε-amino group of lysine, are understood not to be peptidic bonds and are considered non-cleavable.

Some linkers can be cleaved by esterases. Again only certain esters can be cleaved by esterases present inside or outside cells. Esters are formed by the condensation of a carboxylic acid and an alcohol. Simple esters are esters produced with simple alcohols, such as aliphatic alcohols, and small cyclic and small aromatic alcohols. For example, the present inventors found no esterase that cleaved the ester at C-3 of maytansine, since the alcohol component of the ester, maytansinol, is very large and complex.

A non-cleavable linker is any chemical moiety that is capable of linking a maytansinoid to a cell-binding agent in a stable, covalent manner and does not fall under the categories listed above as cleavable linkers. Thus, non-cleavable linkers are substantially resistant to acid-induced cleavage, light-induced cleavage, peptidase-induced cleavage, esterase-induced cleavage, and disulfide bond cleavage.

"Substantially resistant" to cleavage means that the chemical bond in the linker or adjoining the linker in at least 80%, preferably at least 85%, more preferably at least 90%, even more preferably at least 95%, and most preferably at least 99% of the cell-binding agent maytansinoid conjugate population remains non-cleavable by an acid, a photolabile-cleaving agent, a peptidase, an esterase, or a chemical or a physiological compound that cleaves the chemical bond (such as a disulfide bond) in a cleavable linker, for within a few hours to several days of treatment with any of the agents described above.

Furthermore, "non-cleavable" refers to the ability of the chemical bond in the linker or adjoining to the linker to withstand cleavage induced by an acid, a photolabile-cleaving agent, a peptidase, an esterase, or a chemical or a physiological compound that cleaves a disulfide bond, at conditions under which the maytansinoid or the cell binding agent does not lose its activity.

A person of ordinary skill in the art would readily distinguish non-cleavable from cleavable linkers.

An example of an appropriate control for testing whether a linker is substantially resistant to cleavage is a linker with a chemical bond, such as a disulfide bond, that is susceptible to cleavage by any of the agents described above. One can test whether a linker is substantially resistant to cleavage by measuring the stability of the conjugates by ELISA, HPLC, or other suitable means, over a period of time extending from between a few hours to several days, typically 4 hours to 5 days. ELISA assays can be used to measure the level of stable conjugate in the plasma concentration.

Non-cleavable linkers are also characterized in that the in vivo half-life of conjugates comprising non-cleavable linkers is generally about 20% higher than that of conjugates comprising cleavable linkers. In mice, the in vivo half-life of IgG-maytansinoid conjugates linked via non-cleavable linkers is at least 4 days.

Suitable cross-linking reagents that form non-cleavable linkers between the maytansinoid and the cell-binding agent are well known in the art, and can form non-cleavable linkers that comprise a sulfur atom (such as SMCC) or that are without a sulfur atom.

Preferred cross-linking reagents that form non-cleavable linkers between the maytansinoid and the cell-binding agent comprise a maleimido- or haloacetyl-based moiety. According to the present invention, such non-cleavable linkers are said to be derived from maleimido- or haloacetyl-based moiety. Cross-linking reagents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester [AMAS], succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI) (see FIG. 15 for representative structures of maleimido-based cross-linking reagents). These cross-linking reagents form non-cleavable linkers derived from maleimido-based moieties.

Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA) and N-succinimidyl 3-(bromoacetamido)propionate (SBAP) (see FIG. 16 for representative structures of haloacetyl-based cross-linking agents). These cross-linking reagents form non-cleavable linkers derived from haloacetyl-based moieties.

While the active esters described in FIGS. 15 and 16 are comprised of N-succinimidyl and sulfosuccinimidyl esters, other active esters, such as N-hydroxy phthalimidyl esters, N-hydroxy sulfophthalimidyl esters, ortho-nitrophenyl esters, para-nitrophenyl esters, 2,4-dinitrophenyl esters, 3-sulfonyl-4-nitrophenyl esters, 3-carboxy-4-nitrophenyl esters, pentafluorophenyl esters, and sulfonyl tetrafluorophenyl esters can also be used.

Figure 21:
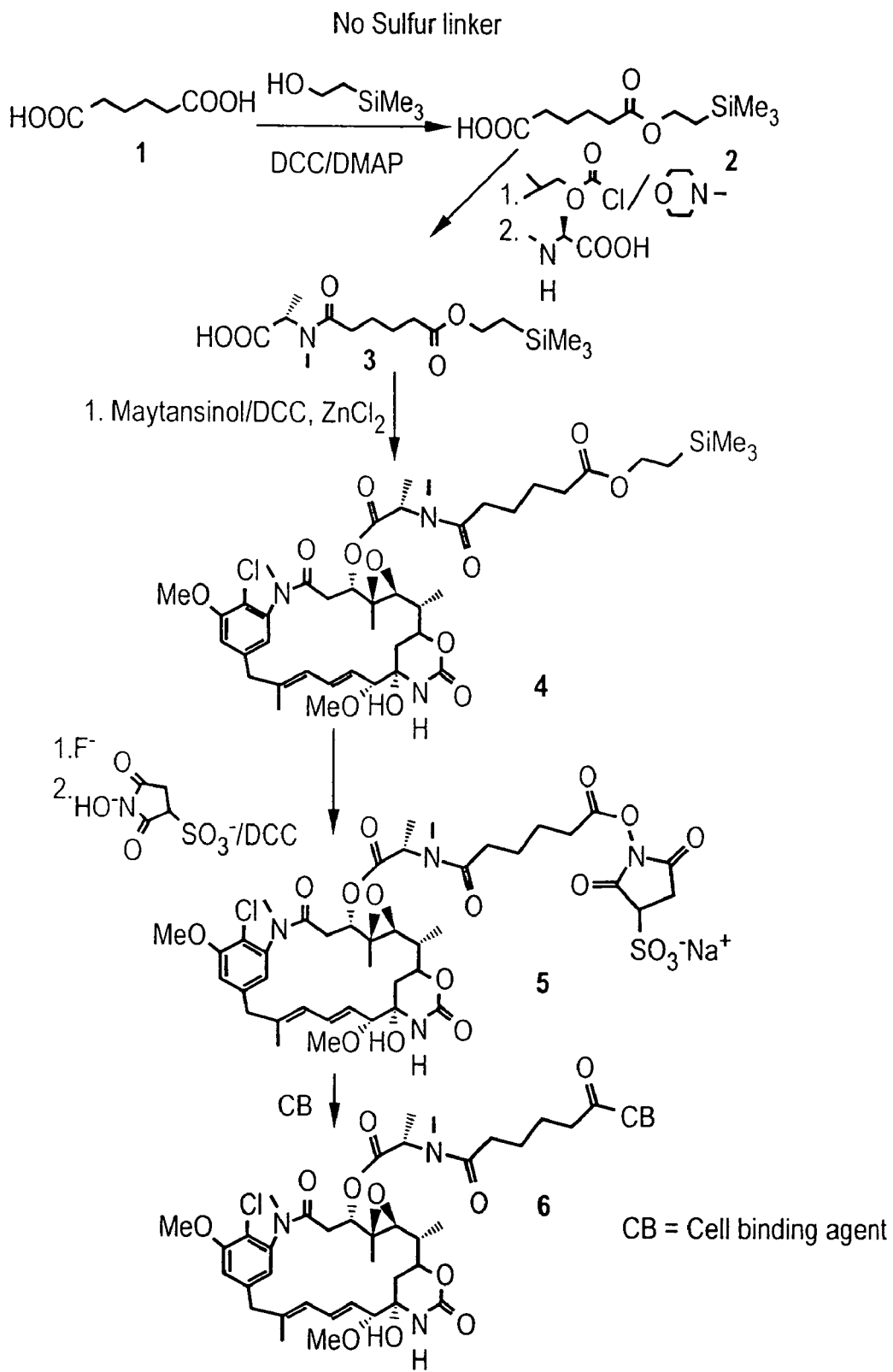
FIG. 21 shows the synthesis of a maytansinoid cell-binding agent conjugate linked via a non-S-containing non-cleavable linker.

Particularly preferred cross-linking reagents form non-cleavable linkers that do not contain a sulfur atom. FIG. 21 shows a maytansinoid molecule derivatized with a cross-linking reagent that is derived from an α,ω-dicarboxylic acid (an alkane or alkene dioic acid wherein the alkane or alkene has 3-24 carbon atoms). When reacted with the cell-binding agent, the cross-linking reagent will form a non-sulfur containing non-cleavable linker (non-S-containing non-cleavable linker).

The maytansinoid molecule of FIG. 21 is made as follows. First a monoester of adipic acid (also known as hexanedioic acid or 1,6-hexanedicarboxylic acid) is prepared by treatment with one equivalent of 2-trimethysilylethanol in the presence of dicyclohexylcarbodiimide. Activation of the remaining carboxylic acid group with isobutyl chloroformate, followed by reaction with N-methyl-L-alanine, provides the acylated N-methyl-L-alanine. Reaction with maytansinol in the presence of dicyclohexylcarbodiimide and zinc chloride, followed by removal of the trimethylsilyl protecting group with tetrabutylammonium fluoride, provides the maytansinoid ester bearing a free carboxy group. Esterification of the carboxyl group by reaction with sulfo N-hydroxysuccinimide in the presence of dicyclohexylcarbodiimide provides the active ester of maytansinol that can react with a cell-binding agent to give a non-cleavable conjugate that does not contain a sulfur atom.

Non-cleavable linkers that do not contain a sulfur atom can also be derived from other dicarboxylic acid based moieties using the method described above. Other suitable dicarboxylic acid based moieties include but are not limited to α,ω-dicarboxylic acids of general formula (IV):

$$\text{HOOC—X}_l\text{—Y}_n\text{—Z}_m\text{—COOH} \tag{IV}$$

In formula (IV), X is a linear or branched alkyl, alkenyl or alkynyl group having 2 to 20 carbon atoms, Y is a cycloalkyl or cycloalkenyl group bearing 3 to 10 carbon atoms, Z is a substituted or unsubstituted aromatic group bearing 6 to 10 carbon atoms or a substituted or unsubstituted heterocyclic group wherein the hetero atom is selected from N, O or S, and wherein l, m and n are each 0 or 1, provided that they are all not 0 at the same time.

Maytansinoids derivatized to contain an active ester that can be directly reacted with a cell-binding agent to form a conjugate having a non-S-containing non-cleavable linker can be represented by formula 5:

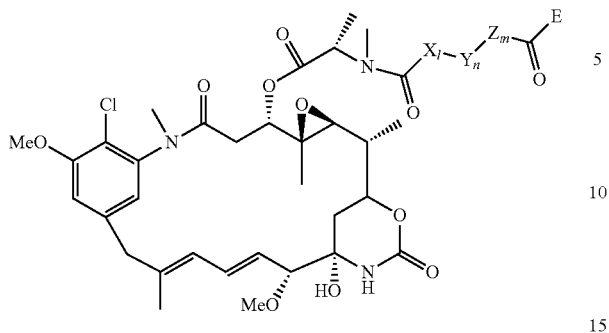

wherein X, Y, Z, l, m and n are all defined as for formula (IV) above, and further wherein E together with the carbonyl group forms an active ester such as N-hydroxy succinimidyl and sulfosuccinimidyl esters, N-hydroxy phthalimidyl ester, N-hydroxy sulfophthalimidyl ester, ortho-nitrophenyl ester, para-nitrophenyl ester, 2,4-dinitrophenyl ester, 3-sulfonyl-4-nitrophenyl ester, 3-carboxy-4-nitrophenyl ester, pentafluorophenyl ester, and sulfonyl tetrafluorophenyl ester.

Preferred is a derivatized maytansinoid represented by formula 6:

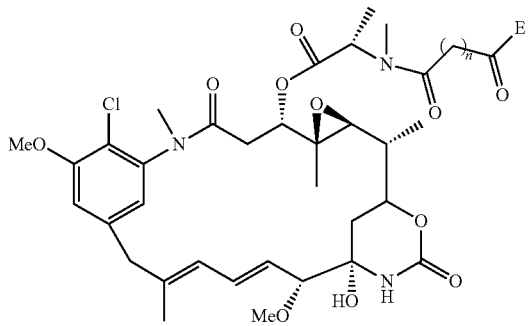

wherein n represents an integer from 3 to 24, and E has the same definition as for the maytansinoid of formula 5.

A more preferred embodiment is the derivatized maytansinoid represented by formula 7:

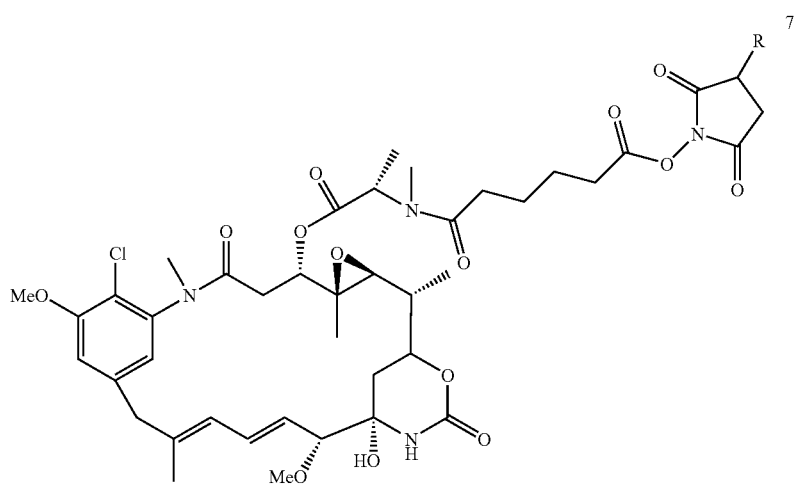

wherein R is H or $SO_3^-Na^+$.

Compounds of the formulae 5, 6, and 7 are novel maytansinoids.

Examples of linear alkyl, alkenyl, or alkynyl groups having 2 to 20 carbon atoms include, but are not limited to, ethyl, propyl, butyl, pentyl, hexyl, propenyl, butenyl, and hexenyl.

Examples of branched alkyl, alkenyl, or alkynyl groups having 2 to 20 carbon atoms include, but are not limited to, isopropyl, isobutyl, sec.-butyl, tert.-butyl, isopentyl, 1-ethyl-propyl, isobutenyl, isopentenyl, ethynyl, propynyl(propargyl), 1-butynyl, 2-butynyl, and 1-hexynyl.

Examples of cycloalkyl or cycloalkenyl groups having from 3 to 10 carbon atoms include, but are not limited to, cyclopropyl, cyclobutyl, cyclopentyl, cyclohexyl, cyclopentenyl, cyclohexenyl, and cycloheptadienyl.

Examples of aromatic groups that contain 6 to 10 carbon atoms include, but are not limited to, phenyl and naphthyl.

Examples of substituted aromatic groups include, but are not limited to, nitrophenyl and dinitrophenyl.

Heterocyclic aromatic groups include, but are not limited to, groups that have a 3 to 10-membered ring containing one or two heteroatoms selected from N, O or S.

Examples of substituted and unsubstituted heterocyclic aromatic groups include, but are not limited to, pyridyl, nitro-pyridyl, pyrollyl, oxazolyl, thienyl, thiazolyl, and furyl.

Heterocycloalkyl radicals include, but are not limited to, cyclic compounds, comprising 3 to 10-membered ring systems, containing one or two heteroatoms, selected from N, O or S.

Examples of heterocycloalkyl radicals include, but are not limited to, dihydrofuryl, tetrahydrofuryl, tetrahydropyrollyl, piperidinyl, piperazinyl, and morpholino.

Examples of α,ω-dicarboxylic acids of the general formula HOOC—$X_l$—$Y_n$—$Z_m$—COOH include, but are not limited to, adipic acid, glutaric acid, pimelic acid, hexene-1,6-dioc acid, pentene-1,5-dioc acid, cyclohexane-dioic acid, and cyclohexene-dioic acid Synthesis of Cytotoxic Conjugates Conjugates of cell-binding agents and maytansinoids can be formed using any techniques presently known or later developed.

Methods of conjugation of cell-binding agents with maytansinoids generally involve two reaction steps. In one method, described in U.S. Pat. No. 5,208,020, a cell-binding agent, such as an antibody, can be modified with a cross-linking reagent to introduce one or more, usually 1-10, reactive groups. The modified cell-binding agent is then reacted with one or more thiol-containing maytansinoids to produce a conjugate.

Alternatively, as disclosed in U.S. Pat. No. 6,441,163 B1, a thiol-containing maytansinoid can first be modified with a cross-linking reagent, followed by reaction of the modified maytansinoid with a cell-binding agent. For example, the thiol-containing maytansinoid can be reacted with the maleimido compounds described in FIG. 15 or with the haloacetyl compounds described in FIG. 16, to give a maytansinoid thioether bearing an active succinimidyl or sulfosuccinimidyl ester. Reaction of these maytansinoids containing an activated linker moiety with a cell-binding agent provides another method of producing a non-cleavable cell-binding agent maytansinoid conjugate.

In another aspect of the invention, as disclosed above, a maytansinoid that does not contain a sulfur atom can first be derivatized by a dicarboxylic acid based cross-linking reagent, followed by reaction with the cell-binding agent, to form a conjugate in which the maytansinoid is linked to the cell-binding agent via a non-S-containing non-cleavable linker.

Typically, an average of 1-10 maytansinoids per antibody are linked. The conjugate can be purified through a Sephadex G-25 column.

The entire disclosures of U.S. Pat. Nos. 5,208,020 and 6,441,163 B1 are expressly incorporated herein by reference.

Representational conjugates of the invention are antibody-maytansinoid derivatives, antibody fragment-maytansinoid derivatives, growth factor-maytansinoid conjugates, such as epidermal growth factor (EGF)-maytansinoid derivatives, hormone-maytansinoid conjugates, such as melanocyte stimulating hormone (MSH)-maytansinoid derivatives, thyroid stimulating hormone (TSH)-maytansinoid derivatives, estrogen-maytansinoid derivatives, estrogen analogue-maytansinoid derivatives, androgen-maytansinoid derivatives, androgen analogue-maytansinoid derivatives, and vitamin-maytansinoid conjugates, such as folate maytansinoid.

Maytansinoid conjugates of antibodies, antibody fragments, protein hormones, protein growth factors and other proteins are made in the same way. For example, peptides and antibodies can be modified with the non-cleavable cross-linking reagents mentioned above. A solution of an antibody in aqueous buffer may be incubated with a molar excess of an antibody-modifying cross-linking reagent such as succinimidyl 4-(N-maleimidomethyl)-cyclohexane-1-carboxylate (SMCC), sulfo-SMCC, -maleimidobenzoyl-N-hydroxysuccinimide ester (MBS), sulfo-MBS, succinimidyl-iodoacetate, or N-succinimidyl-4-(iodoacetyl)-aminobenzoate (SIAB N-succinimidyl-4-(N-maleimidomethyl)-cyclohexane-1-carboxy-(6-amidocaproate), which is a "long chain" analog of SMCC (LC-SMCC), sulfo-LC-SMCC, κ-maleimidoundecanoic acid N-succinimidyl ester (KMUA), sulfo-KMUA, γ-maleimidobutyric acid N-succinimidyl ester (GMBS), sulfo-GMBS, ε-maleimidcaproic acid N-hydroxysuccinimide ester (EMCS), sulfo-EMCS, N-(α-maleimidoacetoxy)-succinimide ester (AMAS), sulfo-AMAS, succinimidyl-6-(β-maleimidopropionamido)hexanoate (SMPH), sulfo-SMPH, N-succinimidyl 4-(p-maleimidophenyl)-butyrate (SMPB), sulfo-SMPH, N-(p-maleimidophenyl)isocyanate (PMPI), N-succinimidyl-4-(iodoacetyl)-aminobenzoate (SIAB), N-succinimidyl iodoacetate (SIA), N-succinimidyl bromoacetate (SBA) and N-succinimidyl 3-(bromoacetamido)propionate (SBAP), as described in the literature. See, Yoshitake et al., 101 Eur. J. Biochem. 395-399 (1979); Hashida et al., J. Applied Biochem. 56-63 (1984); and Liu et al., 18 690-697 (1979); Uto et al., 138 J. Immunol. Meth. 87-94 (1991); Rich et al. 18 J. Med. Chem. 1004-1010 (1975); Kitagawa and Aikawa, 79 J. Biochem. (Tohyo) 233-236 (1976); Tanimori et al., 62 J. Immunol. Meth. 123-128 (1983); Hashida et al., 6 J. Appl. Biochem. 56-63 (1984); Thorpe et al., 140 Eur. J. Biochem. 63-71 (1984), Chrisey et al. 24 Nucl. Acid Res. 3031-3039 (1996), Annunziato et al., 4 Bioconjugate Chem. 212-218 (1993), Rector et al., 24 J. Immunol. Meth. 321-336 (1978), and Inman et al. 2 Bioconjugate. Chem. 458-463 (1991).

The modified antibody is then treated with the thiol-containing maytansinoid (1.25 molar equivalent/maleimido or iodoacetyl group) to produce a conjugate. The mixtures are incubated overnight at about 4° C. The antibody-maytansinoid conjugates are purified by gel filtration through a Sephadex G-25 column. The number of maytansinoid molecules bound per antibody molecule can be determined by measuring spectrophotometrically the ratio of the absorbance at 252 nm and 280 nm. Typically, an average of 1-10 maytansinoids per antibody are linked.

A preferred method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again, conjugates with 1 to 10 drug molecules per antibody molecule result. Examples of antibody-maytansinoid conjugates are shown in FIGS. 17-20.

Similarly, for example, estrogen and androgen cell-binding agents such as estradiol and androstenediol can be esterified at the C-17 hydroxy group by reaction with an appropriately protected thiol group-containing carboxylic acid chloride such as 3-S-acetylpropanoyl chloride. Other methods of esterification can also be employed as described in the literature (Haslam, 36 Tetrahedron 2400-2433 (1980)). The protected or free thiol-containing androgen or estrogen can then be reacted with a thiol-containing maytansinoid to produce conjugates. The conjugates can be purified by column chromatography on silica gel or by HPLC.

A particularly preferred method is to modify maytansinol with a cross-linking reagent that results in a linkage that does not contain any sulfur atoms, followed by reaction of the modified maytansinoid with an antibody to produce conjugates.

Therapeutic Efficacy of the Cytotoxic Conjugates of the Invention

Cell-binding agent maytansinoid conjugates of the invention can be evaluated for their ability to suppress proliferation of various cell lines in vitro. For example, cell lines such as the human colon carcinoma line COLO205, the human melanoma cell line A375, the human myeloid leukemia cell line HL60, the human breast carcinoma line SKBR3, or the human epidermoid carcinoma cell line KB can be used for the assessment of cytotoxicity of these conjugates. Cells to be evaluated can be exposed to the compounds for 24 hours and the surviving fractions of cells measured in direct assays by known methods. (See, e.g. Goldmacher et al., 135 J. Immunol. 3648-3651 (1985), and Goldmacher et al., 102 J. Cell Biol. 1312-1319 (1986).) $IC_{50}$ values can then be calculated from the results of the assays.

High cytotoxicity can be defined as exhibiting a toxicity having an $IC_{50}$ (the inhibiting concentration of a toxic substance that leaves a surviving fraction of 0.5) of about $10^{-8}$ M or less when measured in vitro with SKBR3 cells upon a 24 hour exposure time to the drug.

Figure 4:
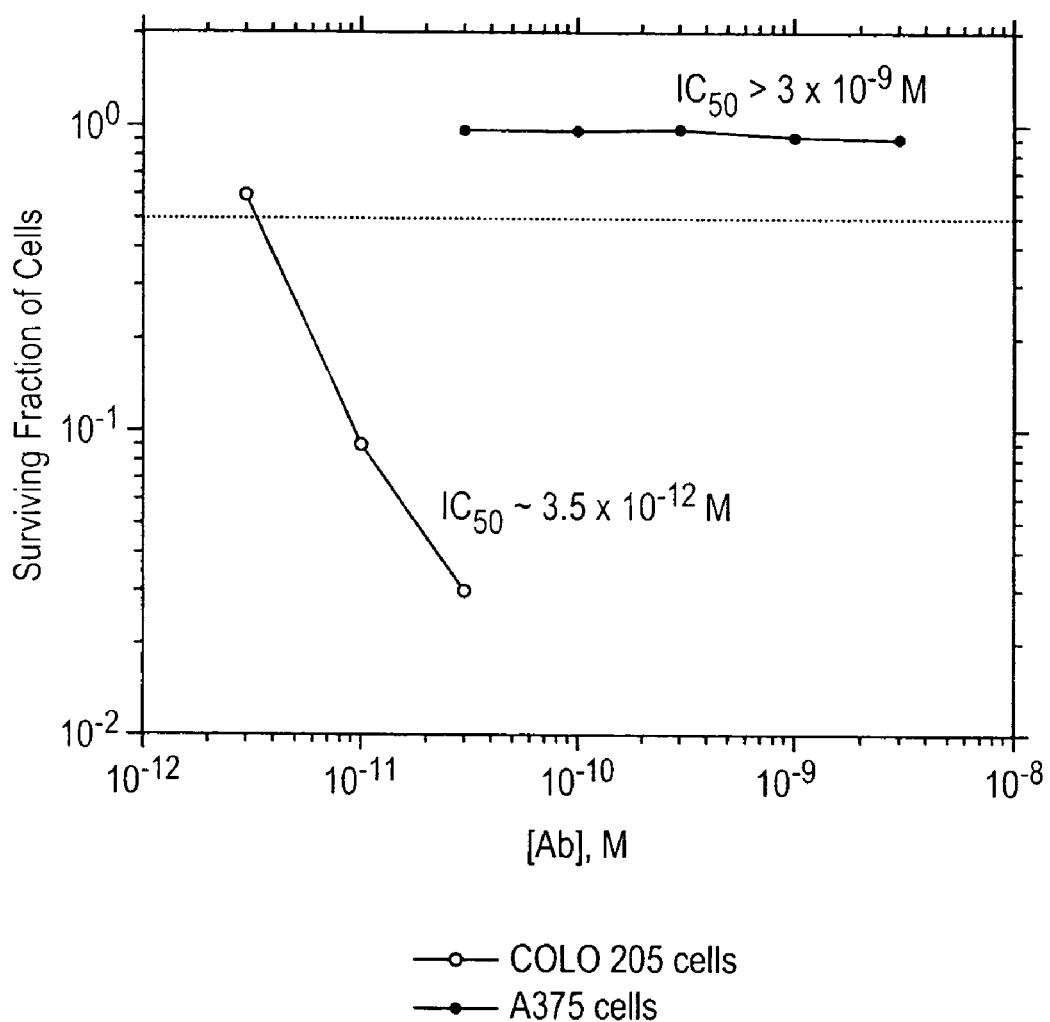
FIG. 4 shows graphically the cytotoxicity of huC242-SMCC-DM1.

The in vitro potency and target specificity of antibody-maytansinoid conjugates of the present invention are shown in FIG. 4. Conjugates of huC242 with DM1 using the cross-linking reagent SMCC are highly potent in destroying antigen positive SKBR3 cells, with an $IC_{50}$ value of $3.5 \times 10^{-12}$ M. In contrast, antigen negative A375 cells are about 800-fold less sensitive demonstrating that maytansinoid conjugates of the present invention are highly potent and specific.

Figure 6A:
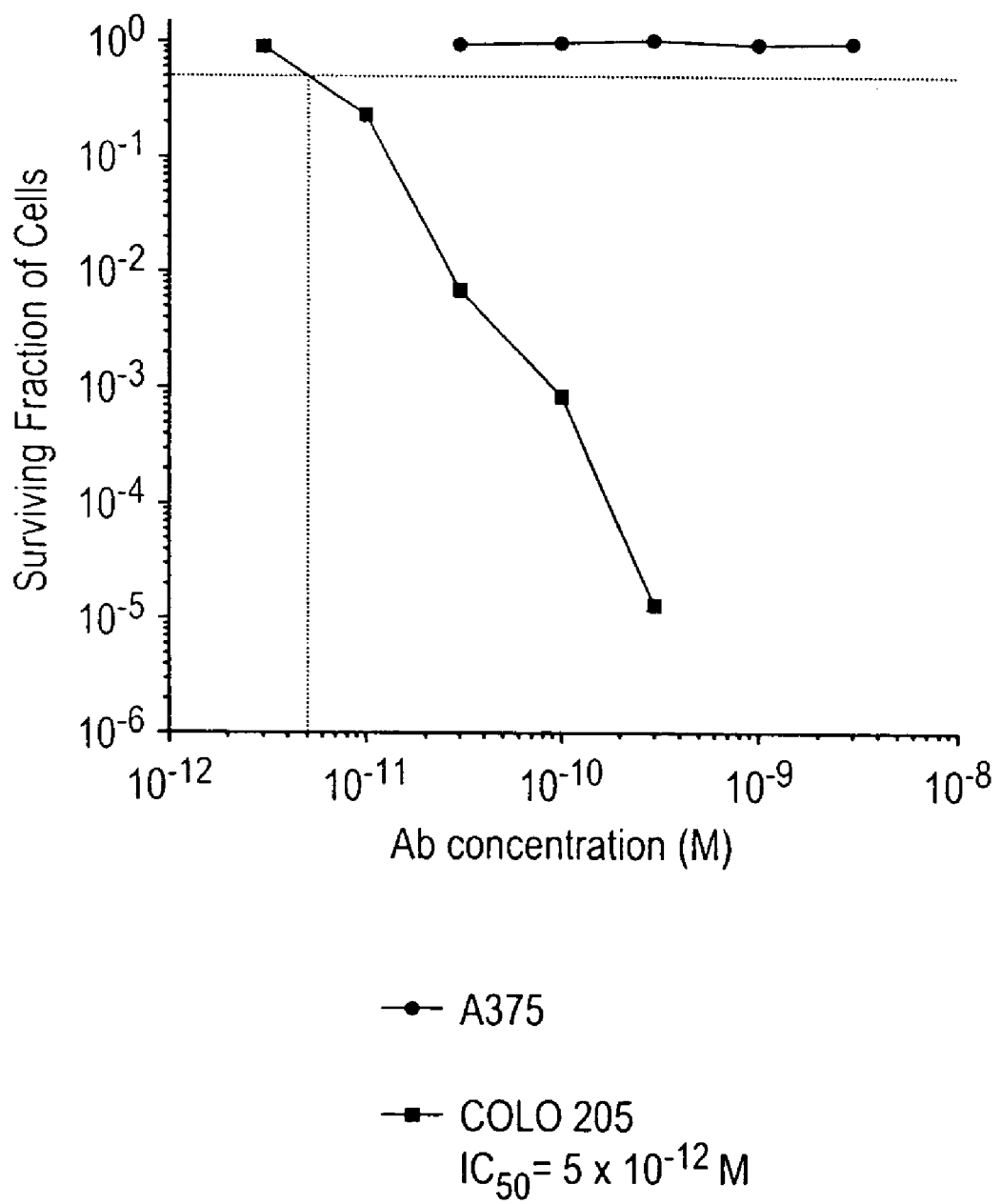
Figure 6B:
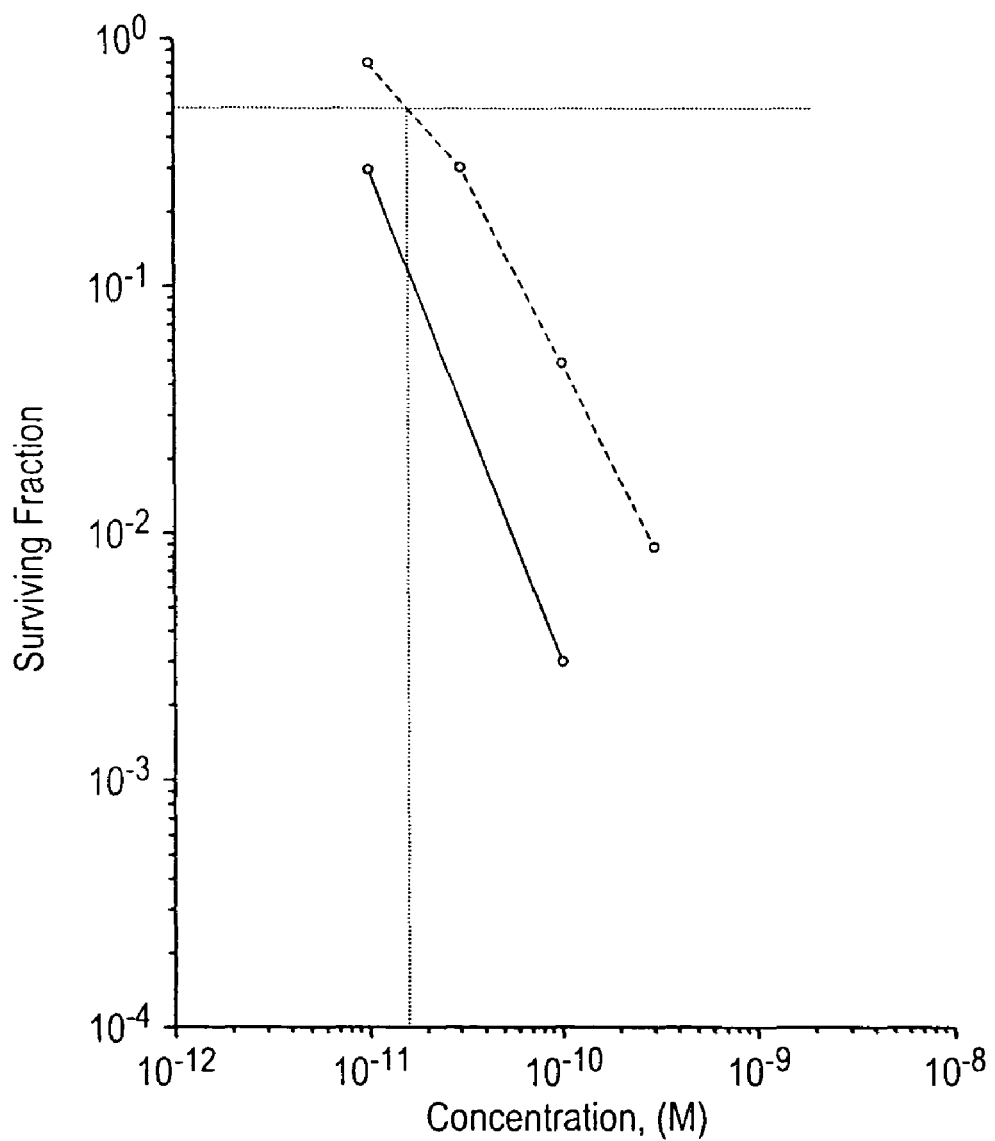
Figure 7:
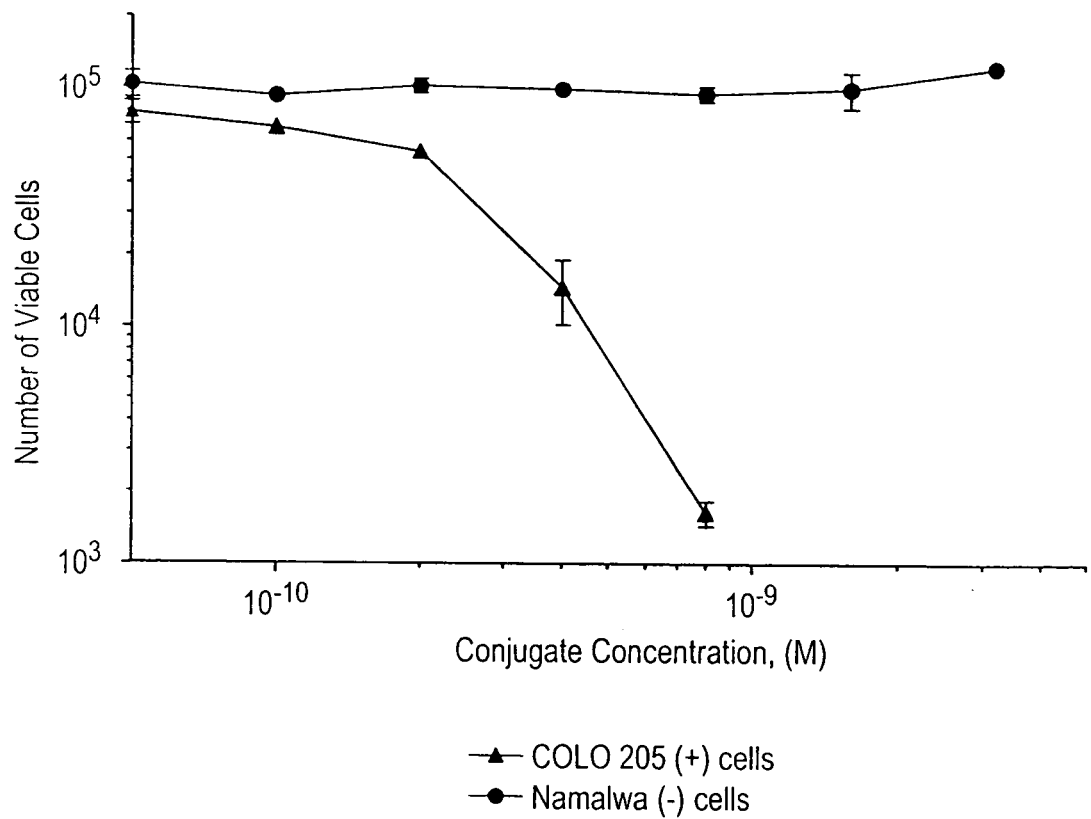
Figure 8B:
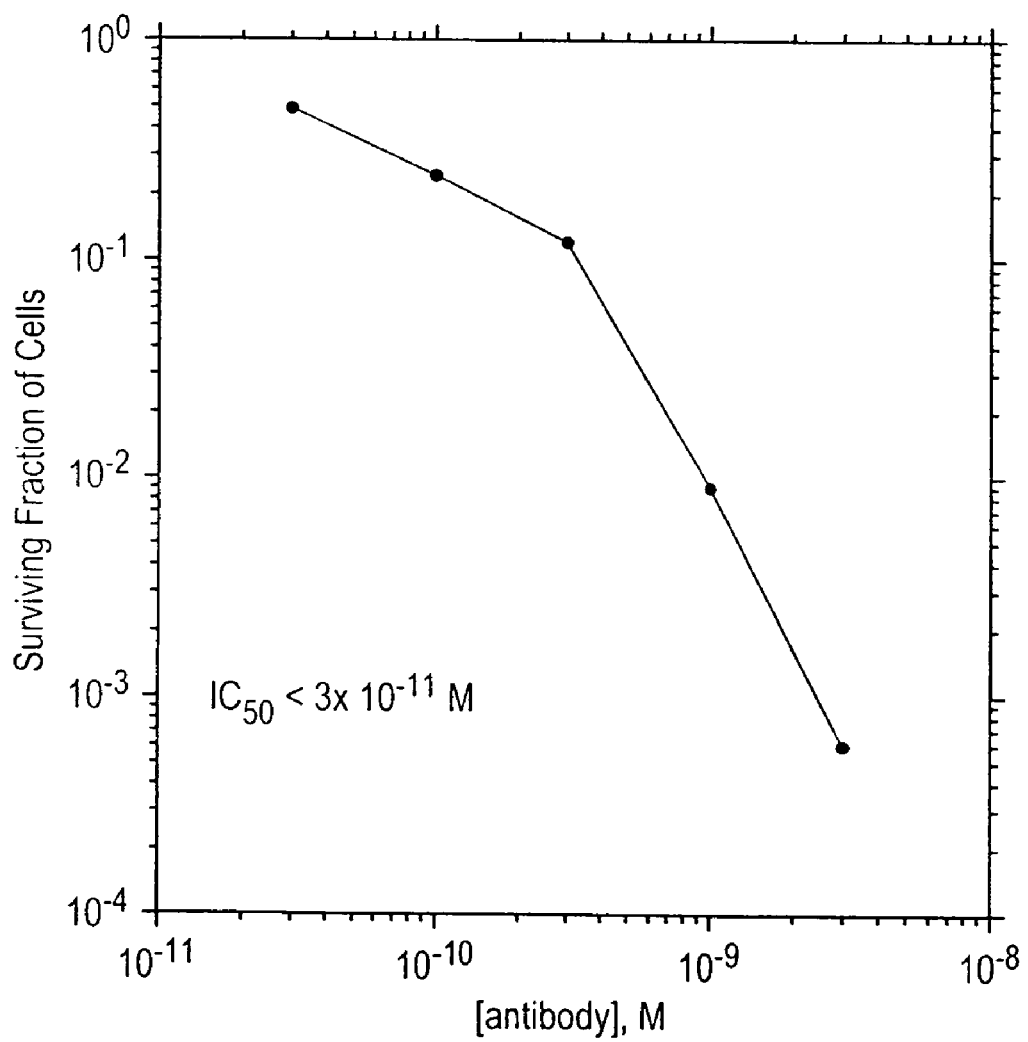
Figure 8D:
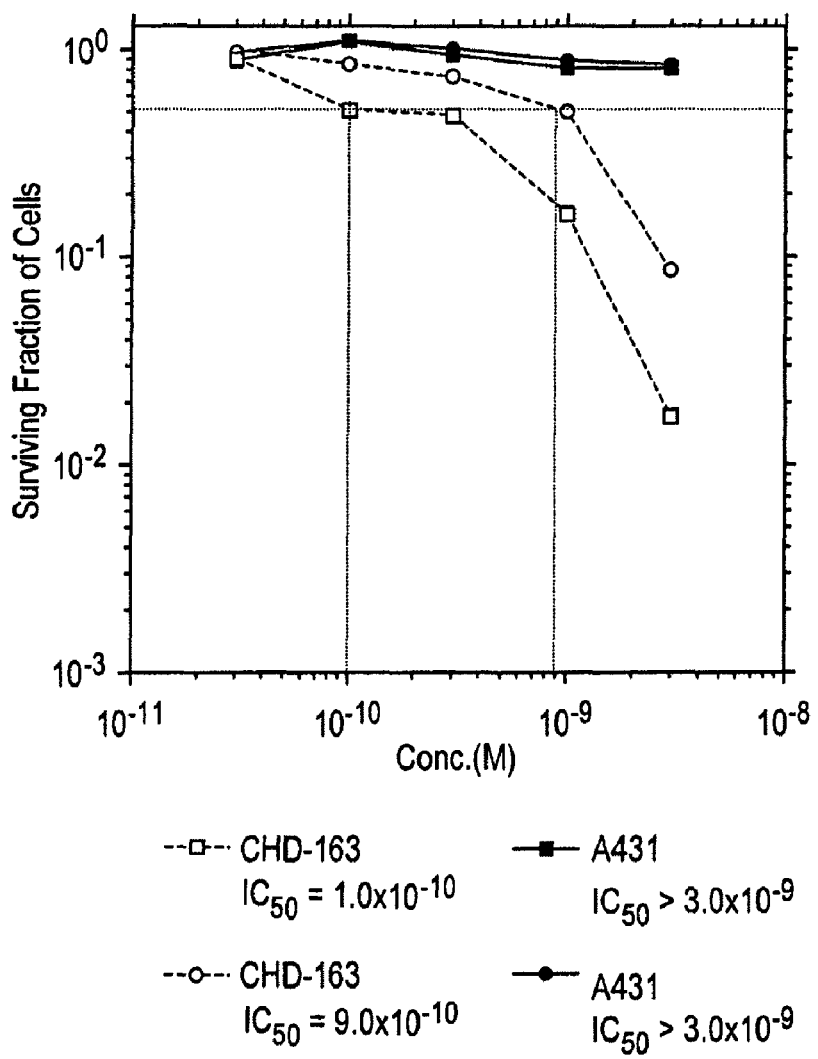

The huC242-SMCC-DM1 conjugate was of equal or greater potency when compared to conjugates prepared with disulfide-containing linkers in clonogenic (FIG. 6A-C) and in indirect cytotoxicity assays (FIG. 7). These results were unexpected, based on previously published data demonstrating that an anti-Her2 antibody conjugated to maytansinoids via SMCC showed no specific activity (Chari et al., 52 Cancer Res. 127-133 (1992).

Activity of conjugates prepared with SMCC non-cleavable linker is not restricted to huC242 conjugates. Specific activity in vitro was also observed with SMCC-DM1 conjugates of trastuzumab, an anti-Her2 antibody; My9-6, an anti-CD33 antibody; KS77, an anti-EGFR antibody; and N901, an anti-CD56 antibody (FIGS. 8A-D and 25).

Figure 22:
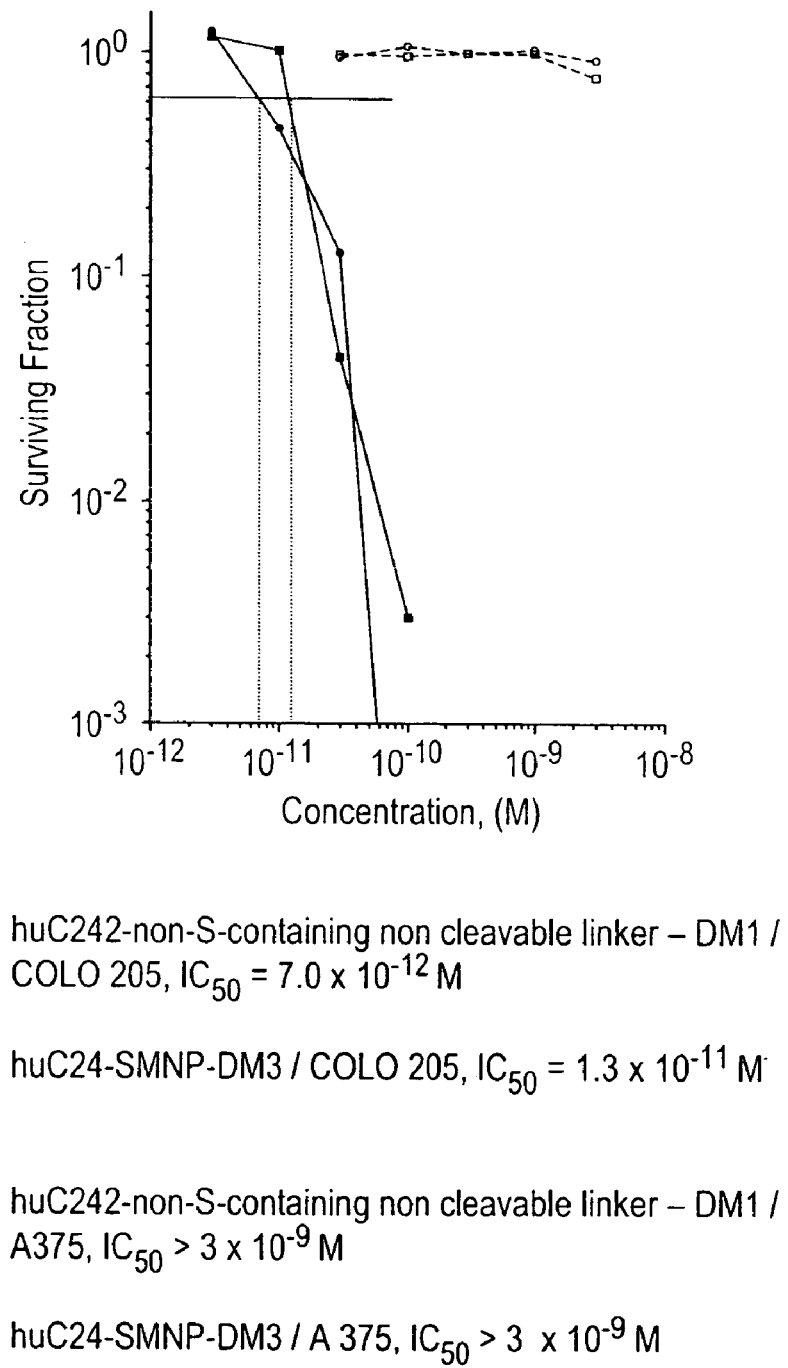
FIG. 22 shows graphically cytotoxicity of huC242-non-S-containing non-cleavable linker-DM1.
Figure 28:
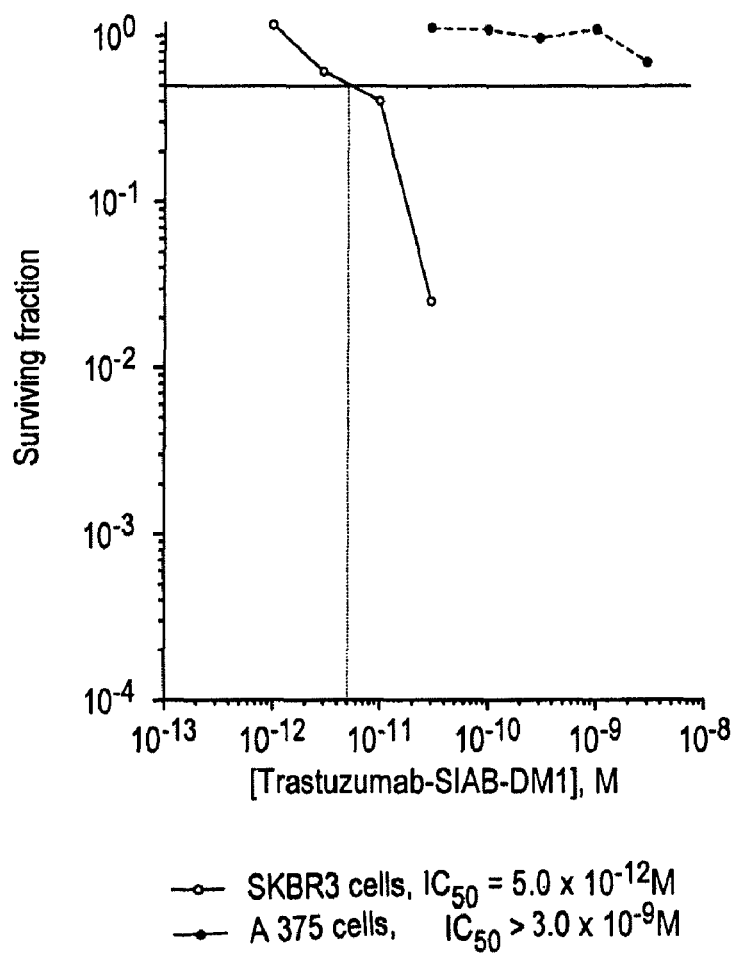
FIG. 28 shows graphically the cytotoxicity and specificity of trastuzumab-SIAB-DM1.

In addition, conjugates with non-cleavable linkers that show specific activity in vitro are not restricted to the SMCC linker. A huC242 conjugate of DM1 synthesized with the non-cleavable linker SIAB showed potent and antigen-specific cytotoxicity in clonogenic assays in vitro (FIG. 9). Further, a trastuzumab conjugate of DM1 synthesized with SIAB was also cytotoxic in clonogenic assays (FIG. 28). Further, a huC242-non-S-containing non-cleavable linker-DM1 conjugate also demonstrated potent and antigen-specific cytotoxicity in clonogenic assays in vitro (FIG. 22).

Figure 10B:
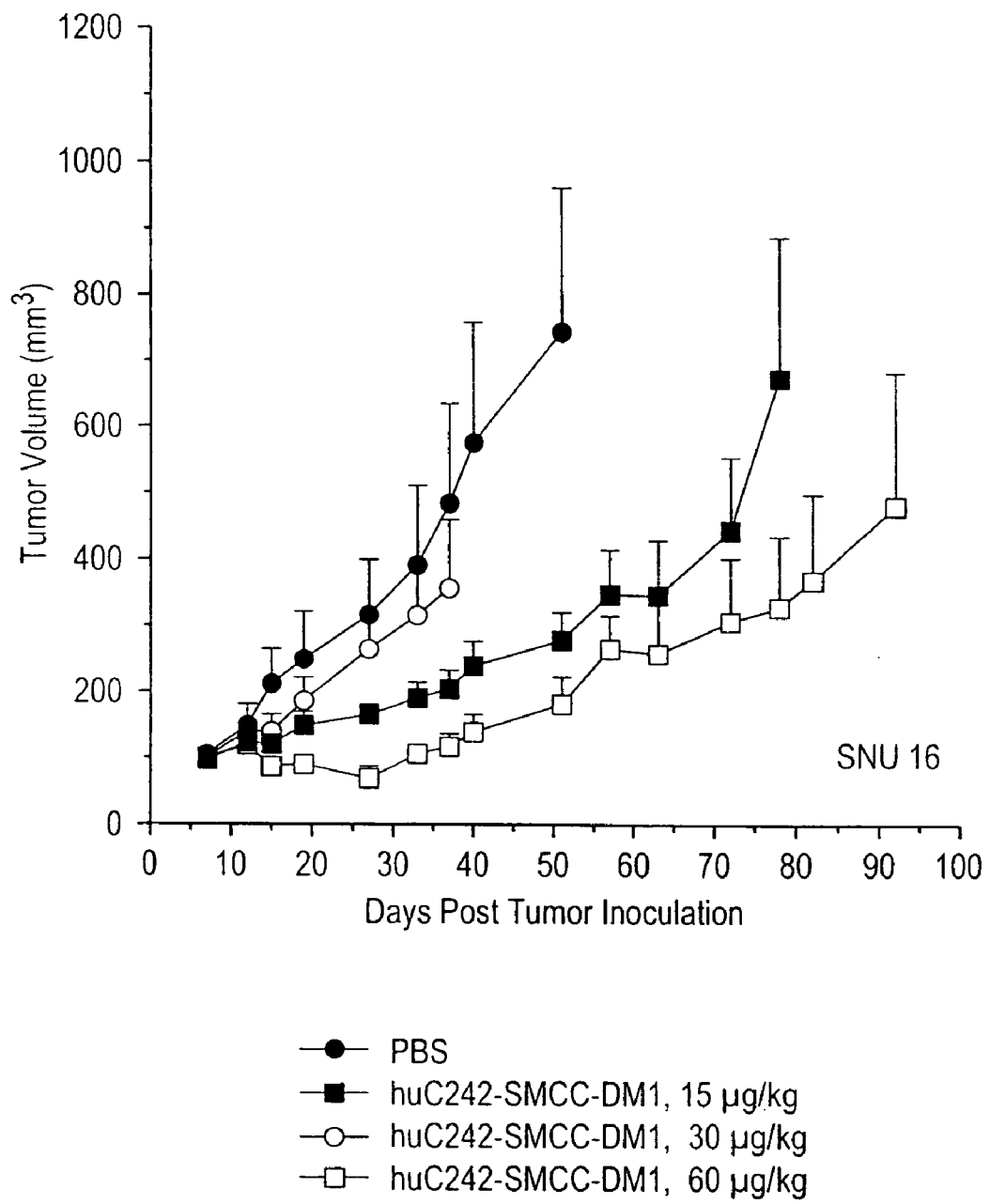
FIG. 10B shows graphically the antitumor activity of huC242-SMCC-DM1 against SNU16 human gastric tumor xenografts in SCID mice.

Antibody conjugates with DM1 using the SMCC linker show anti-tumor efficacy against human tumor xenografts in mice (FIGS. 10A-C). First, as shown in FIG. 10A, marked inhibition of tumor growth was observed upon treatment of COLO 205 colon tumor xenografts with huC242-SMCC-DM1. In this experiment, one group of five animals bearing established subcutaneous tumors was treated with huC242-SMCC-DM1 at a dose of 150 μg/kg of conjugated DM1. Tumor sizes were measured periodically and graphed vs. time after tumor inoculation. All five treated animals had a complete remission, although three animals relapsed thereafter at different time points, whereas two animals stayed tumor-free until termination of the experiment (FIG. 10A). This anti-tumor activity is observed at conjugate doses that have no effect on mouse body weight, a measure of drug toxicity. Second, as shown in FIG. 10B, treatment of mice bearing COLO 205 colon carcinoma tumor xenografts with the huC242-SMCC-DM1 conjugate resulted in complete regression of tumors, with some mice remaining free of detectable tumors for over 2 months post-treatment (FIG. 10A). In this experiment, three groups of five animals each bearing established subcutaneous SNU tumors were treated with huC242-SMCC-DM1 at doses of 15 μg/kg, 30 μg/kg, and 60 μg/kg of conjugated DM1, respectively. Tumor sizes were measured periodically and graphed vs. time after tumor inoculation. HuC242-SMCC-DM1 showed a dose-dependent antitumor effect. Again, this activity was obtained at a conjugate concentration that showed no effect on mouse body weight. A trastuzumab-SMCC-DM1 conjugate also showed significant tumor regression, in a mouse tumor xenograft model with the MCF-7 breast carcinoma cell line (FIG. 10C).

Figure 11:
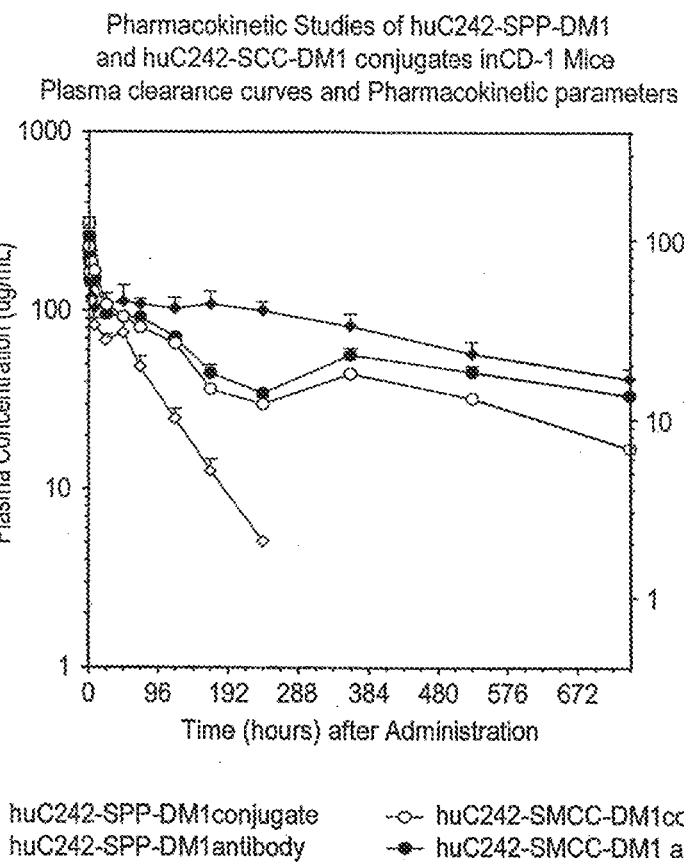
FIG. 11, shows graphically plasma clearance rates of huC242-SMCC-DM1 compared to conjugates prepared with disulfide-containing linkers.

Plasma clearance of antibody-maytansinoid conjugate synthesized with the non-cleavable linker SMCC is very slow and comparable to the clearance of antibody alone. This is in sharp contrast to plasma clearance of conjugates prepared with relatively labile disulfide bonds such as huC242-SPP-DM1. For example, the half-life for clearance of the SMCC conjugate is approximately 320 hours, while the half-life for the SPP conjugate is in the range of 40-50 hours (FIG. 11). However, the clearance of the antibody component for each type of conjugate is identical, suggesting that the difference in measured conjugate clearance rate is due to the loss of maytansinoid from the antibody conjugate in the case of the SPP-DM1 conjugate. The non-cleavable SMCC linkage is therefore much more resistant to maytansinoid-linker cleavage activities present in vivo than the SPP-DM1 conjugate. Further, the decreased clearance rate for the SMCC linked conjugates, compared to SPP-DM1 conjugates, leads to a nearly 5-fold increase in overall maytansinoid exposure of the animal as measured by the area under the curve (AUC). This increased exposure could have substantial impact on drug efficacy in some cases.

Figure 12A:
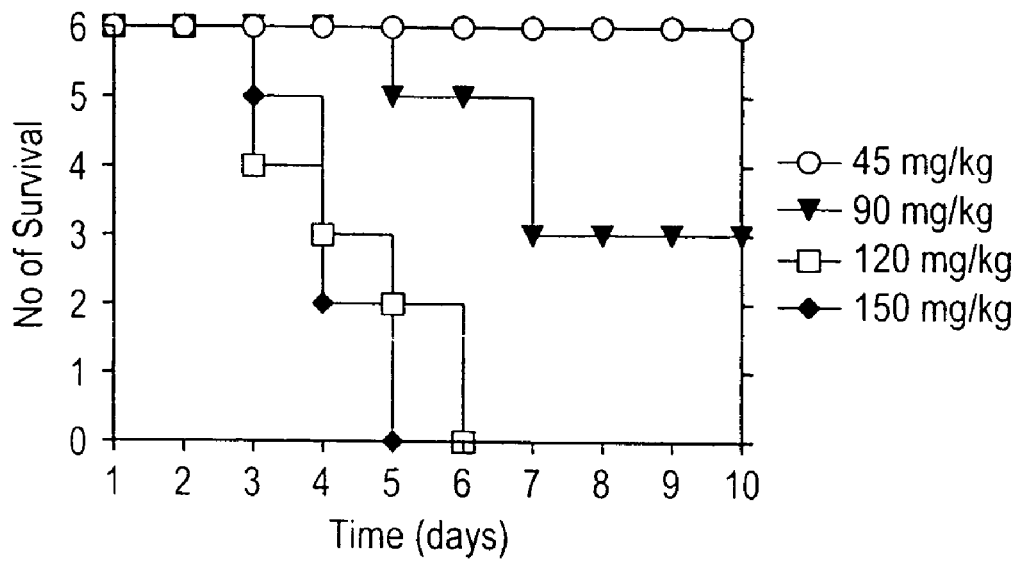
FIGS. 12A-D show graphically results of acute toxicity studies of huC242-SMCC-DM1 compared to conjugates prepared with disulfide-containing linkers.
Figure 12B:
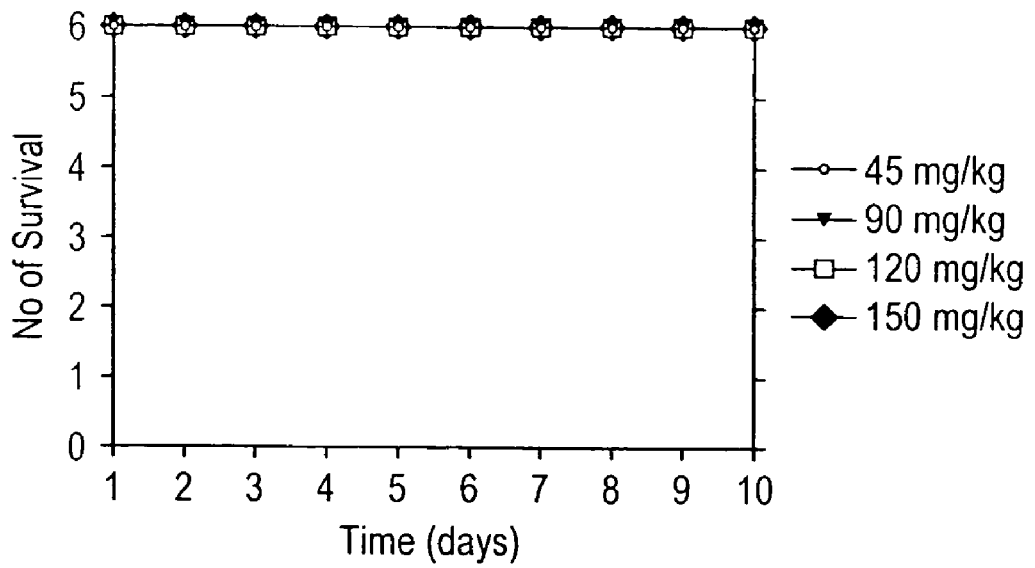
Figure 12C:
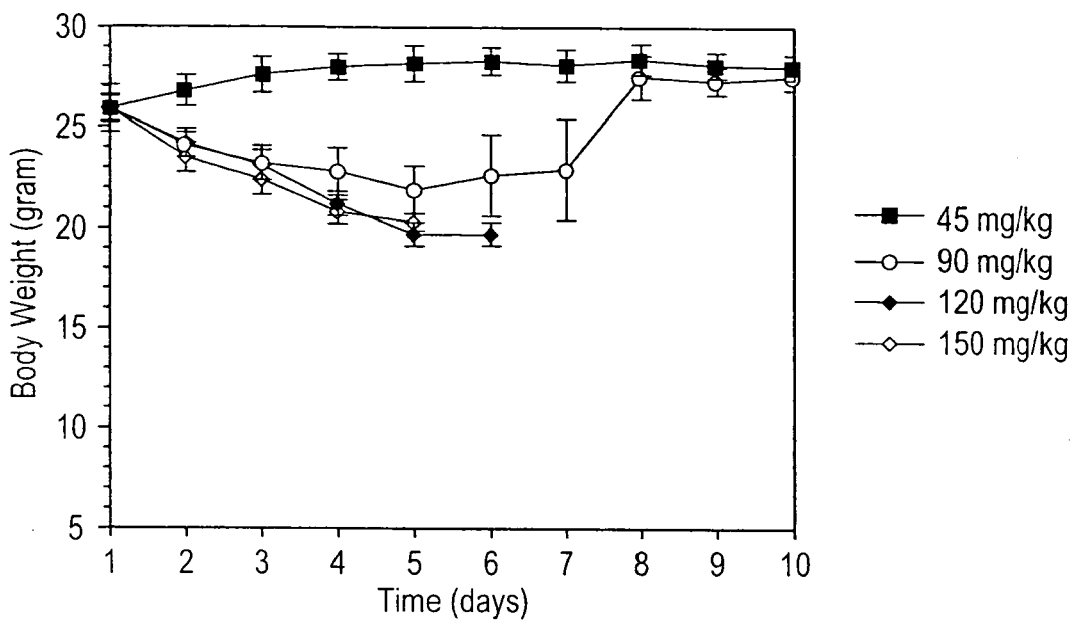
Figure 12D:
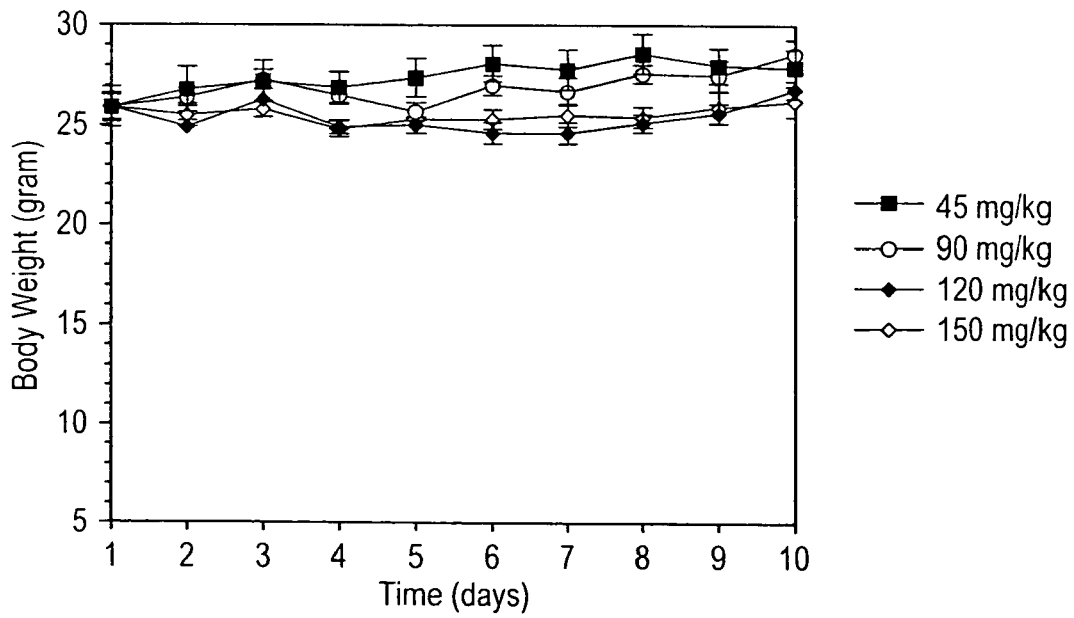

Maytansinoid conjugates prepared with non-cleavable linkers such as SMCC show an unexpected increased tolerability in mice compared with conjugates prepared with cleavable disulfide linkers. An acute toxicity test with a single intravenous dose was carried out in female CD-1 mice. A comparison of the tolerability of a huC242-SMCC-DM1 conjugate (non-cleavable) with huC242 conjugates prepared with linkers containing cleavable disulfide bonds was conducted by monitoring the death of mice (FIGS. 12A and B) and signs of toxicity (FIGS. 12C and D) over a series of four escalating doses of each conjugate. The maximum tolerated dose (MTD) for the SMCC-DM1 conjugate was greater than the highest dose tested (150 mg/kg) while the MTD for the disulfide-linked conjugate SPP-DM1 was in the range of 45-90 mg/kg. At 150 mg/kg, all mice in the SMCC-DM1 treated group survived, while lethal toxicity was observed for all mice in the SPP-DM1 treated group by 96 hours post-treatment.

Figure 13:
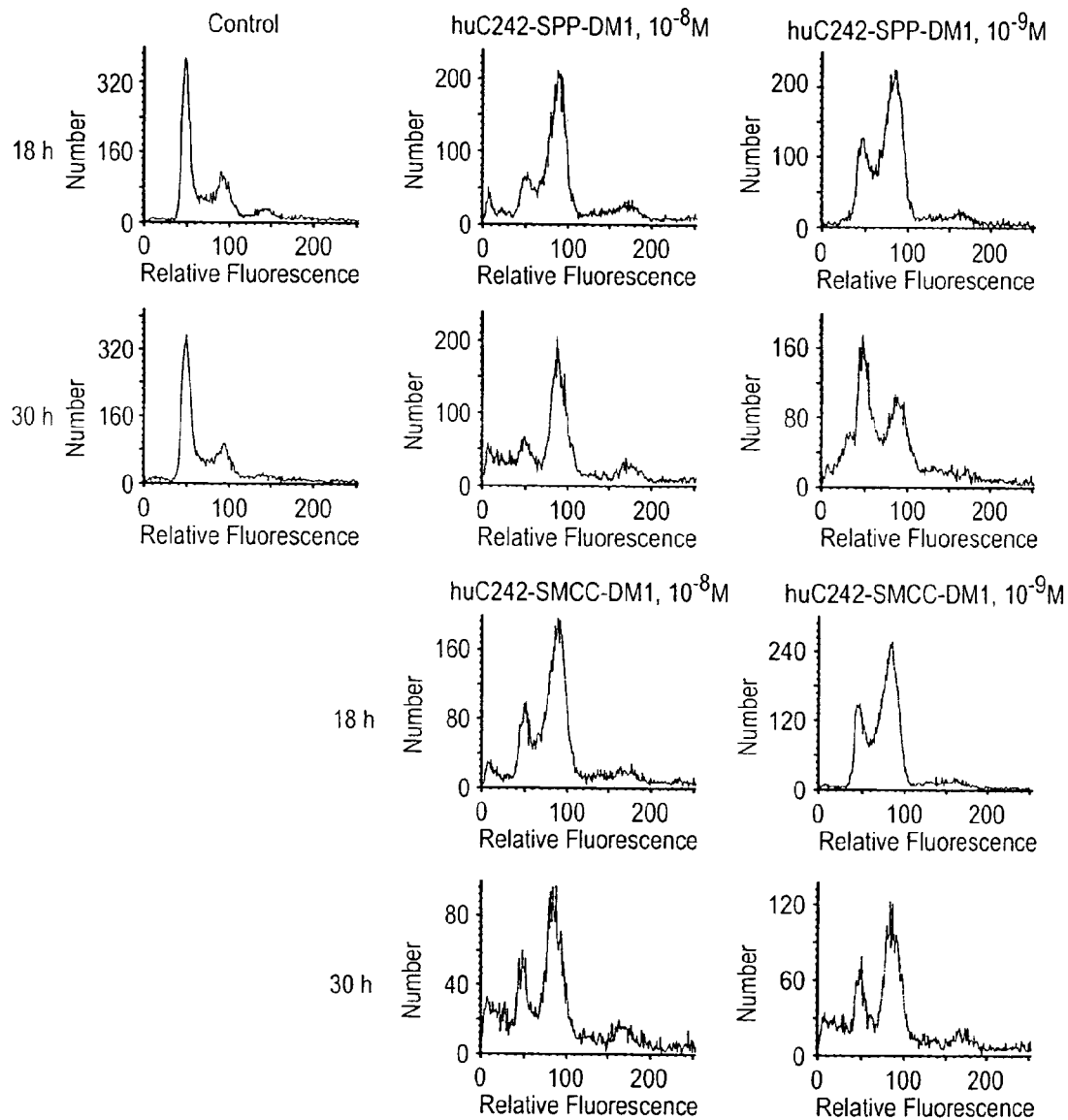
FIG. 13 shows the durability of cell-cycle arrest and cell destroying activity demonstrated by huC242-SMCC-DM1 compared to conjugates prepared with disulfide-containing linkers.

Maytansinoid conjugates are thought to impart their cell destroying activity through the inhibition of microtubule polymerization. This inhibition of microtubule polymerization leads to an arrest of the cell cycle principally at G2/M. The antigen-dependent arrest of cells at G2/M by antibody-maytansinoid conjugates can be monitored by flow cytometry analysis (FIG. 13). Treatment of COLO205 cells with huC242-SPP-DM1 or huC242-SMCC-DM1 conjugate results in a complete G2/M arrest by 6-10 hours. By 30 hours post-treatment however, some of the cells arrested by treatment with the disulfide-linked huC242-SPP-DM1 conjugate escape from cell cycle arrest and reinitiate cell division. Surprisingly, cells treated with the non-cleavable conjugate do not escape from the cell cycle block at this later time point. The difference in the durability of the activity of these two conjugates is also reflected in percentage of dead cells at the 30 hour time point, as judged by a dye exclusion assay using trypan blue. These results demonstrate an unexpected durability of the molecular events induced by treatment with the non-cleavable SMCC linker conjugates.

Figure 14A:
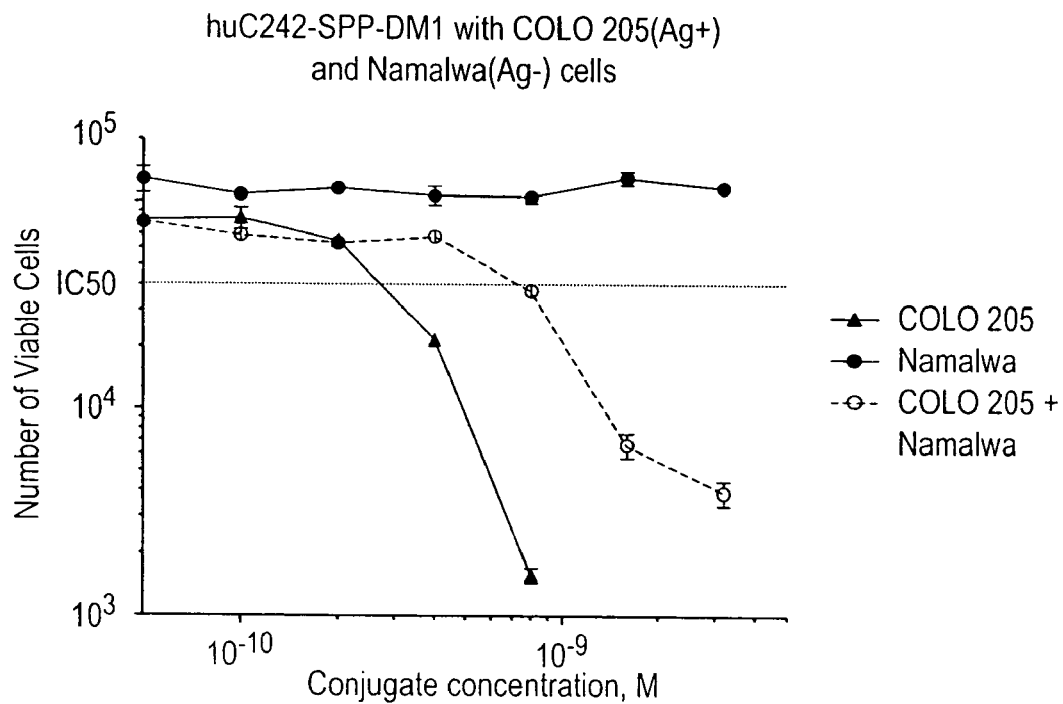
FIGS. 14A-C show the minimal bystander effect activity of huC242-SMCC-DM1 compared to conjugates prepared with disulfide-containing linkers.
Figure 14B:
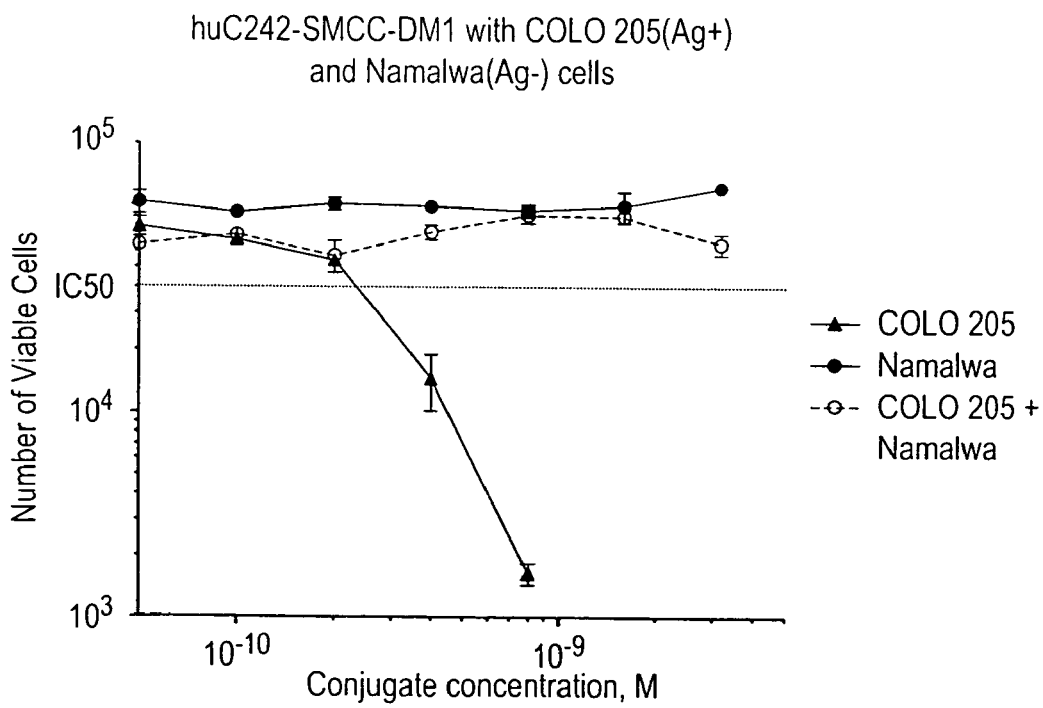
Figure 14C:
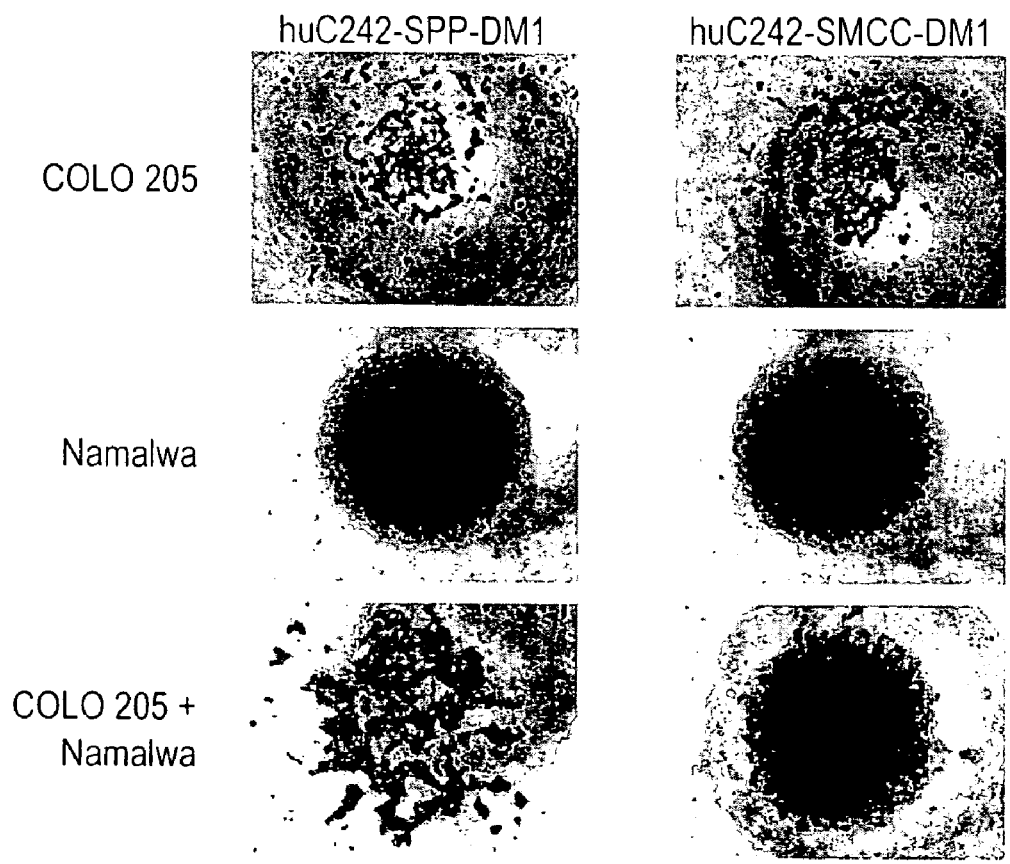
Figure 18:
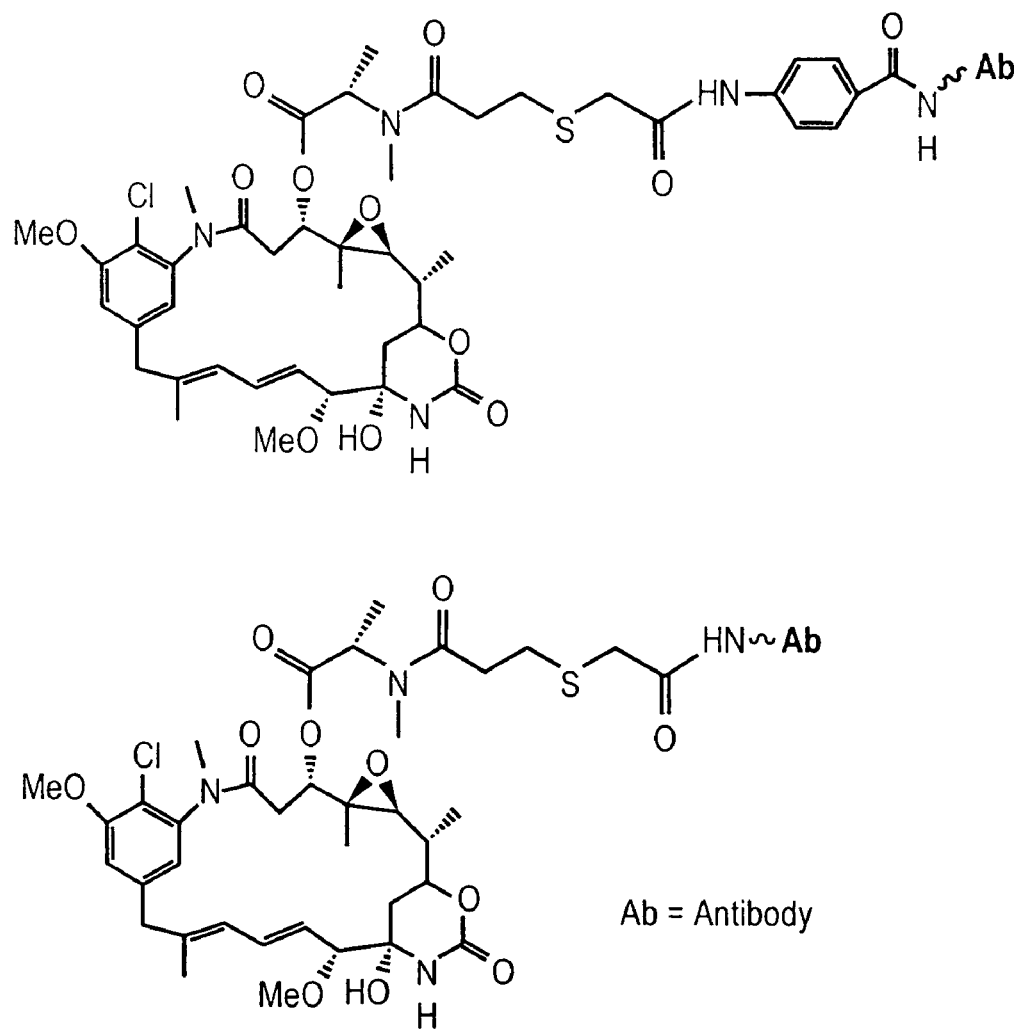
FIG. 18 shows the structure of antibody-SIAB-DM1 conjugates.
Figure 20:
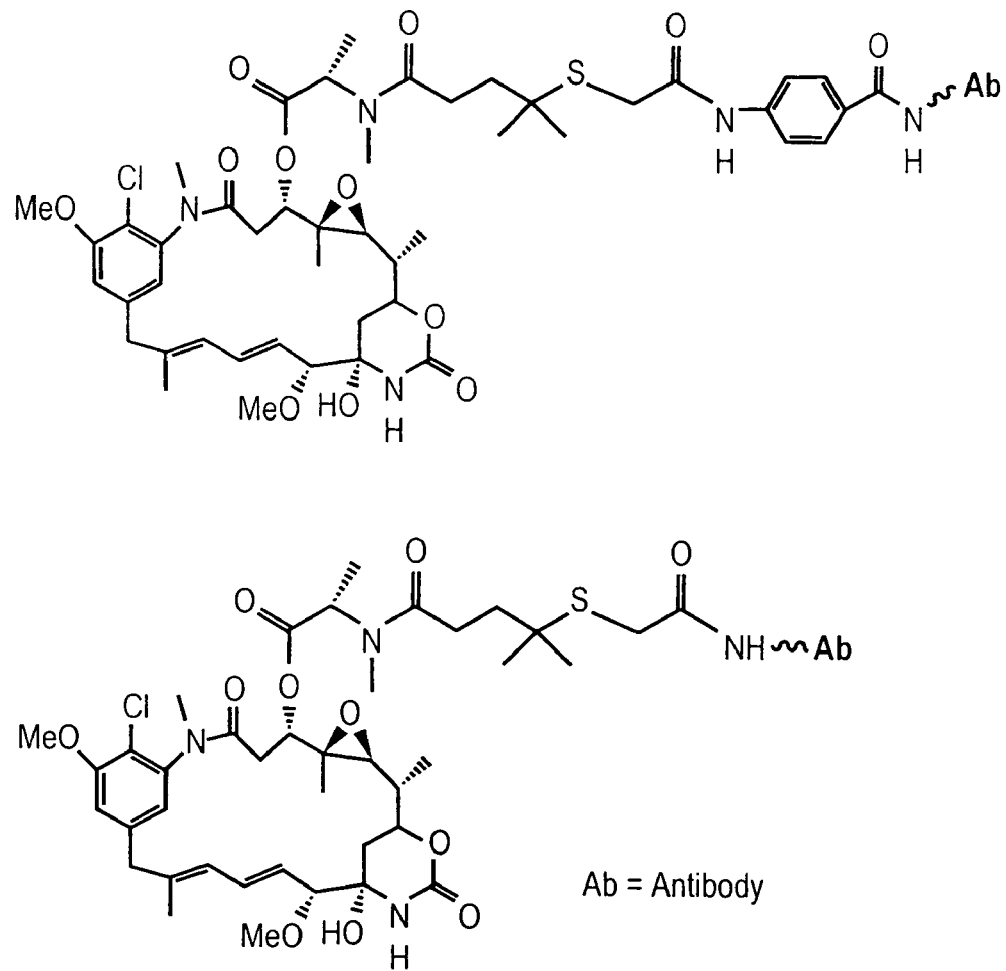
FIG. 20 shows the structure of antibody-SIAB-DM4 conjugates.

An additional aspect of conjugates prepared with non-cleavable linkers compared to conjugates that have cleavable disulfide linkers is the absence of activity toward antigen-negative cells when in close proximity to antigen-positive cells, termed here the bystander effect. That is, the conjugates prepared with non-cleavable linkers have minimal bystander activity. Both the huC242-SPP-DM1 (cleavable) and huC242-SMCC (non-cleavable) conjugates show potent cell destroying activity toward the antigen-positive COLO 205 cell line and have no activity toward the antigen-negative cell line, Namalwa, when cultured separately (FIGS. 14A-C). However, treatment of co-cultures of COLO 205 and Namalwa cells with huC242-SPP-DM1 reveals dramatic cell destroying activity of the conjugate toward even the antigen-negative Namalwa cells. In contrast, the huC242-SMCC-DM1 conjugate does not demonstrate any such bystander activity under these conditions. No cell destroying activity against Namalwa cells is observed with the huC242-SMCC-DM1 conjugate even when co-cultured with the antigen-positive COLO 205 cells. This minimal bystander activity of the non-cleavable conjugate, as measured in this in vitro assay, may contribute to the increased tolerability of conjugate with non-cleavable linkers observed in acute toxicity studies.

Results from the above experiments demonstrate that the maytansinoid conjugates with non-cleavable linkers of the present invention possess vastly improved anti-tumor activity compared to previously described cell-binding agent maytansinoid conjugates.

Methods of Use

The above-described conjugates can be used in a method for targeting maytansinoids to a selected cell population, the method comprising contacting a cell population or tissue suspected of containing the selected cell population with a cell-binding agent maytansinoid conjugate, wherein one or more maytansinoids is covalently linked to the cell-binding agent via a non-cleavable linker and the cell-binding agent binds to cells of the selected cell population.

The above-described conjugates can also be used in a method of destroying cells, the method comprising contacting the cells with a cell-binding agent maytansinoid conjugate, wherein one or more maytansinoids is covalently linked to the cell-binding agent via a non-cleavable linker and the cell-binding agent binds to the cells.

The above-described conjugates can also be used in a method of treatment of afflictions including but not limited to malignant tumors, autoimmune diseases, graft rejections, graft versus host disease, viral infections, microorganism infections, and parasite infections, the method comprising administering to a subject in need of treatment an effective amount of a cell-binding agent maytansinoid conjugate, wherein one or more maytansinoids is covalently linked to the cell-binding agent via a non-cleavable linker and the cell-binding agent binds diseased or infected cells of the affliction.

Examples of medical conditions that can be treated according to the methods of the present invention include but are not limited to malignancy of any type including, for example, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

The methods can be practiced in vitro or in vivo.

The above-described conjugates can be used in a method of in vitro use to treat, for example, autologous bone marrow cells prior to their transplant into the same patient in order to destroy diseased or malignant cells; bone marrow cells or other tissue prior to their transplantation in order to destroy T cells and other lymphoid cells and prevent graft-versus-host-disease (GVHD); cell cultures in order to destroy all cells except for desired variants that do not express the target antigen; or cell cultures in order to destroy variant cells that express undesired antigen; the method comprising treating the cells with an effective amount of a cell-binding agent maytansinoid conjugate, wherein one or more maytansinoids is covalently linked to the cell-binding agent via a non-cleavable linker and the cell-binding agent binds the cells that are to be destroyed.

The conditions of clinical and non-clinical in vitro use are readily determined by one of ordinary skill in the art.

For example, treatment can be carried out as follows. Bone marrow can be harvested from the patient or other individual and then incubated in medium containing serum to which is added the cytotoxic agent of the invention, concentrations range from about 10 pM to 1 nM, for about 30 minutes to about 48 hours at about 37° C. The exact conditions of concentration and time of incubation, i.e., the dose, can be readily determined by one of ordinary skill in the art. After incubation the bone marrow cells can be washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells can be stored frozen in liquid nitrogen using standard medical equipment.

For clinical in vivo use, the cytotoxic agent can be supplied as a solution or a lyophilized powder that is tested for sterility and for endotoxin levels. Examples of suitable protocols of conjugate administration are as follows. Conjugates can be given weekly for 4 weeks as an intravenous bolus each week. Bolus doses can be given in 50 to 500 ml of normal saline to which 5 to 10 ml of human serum albumin can be added. Dosages will be 10 mg to 2000 mg per administration, intravenously (range of 100 ng to 20 mg/kg per day). After four weeks of treatment, the patient can continue to receive treatment on a weekly basis.

Specific in vivo clinical protocols with regard to route of administration, excipients, diluents, dosages, times, etc., can be determined by one of ordinary skill in the art as the clinical situation warrants.

If desired, other active agents, such as other anti-tumor agents, may be administered along with the conjugate.

Novel Conjugates, Compositions and Methods of Making the Conjugates

While some conjugates of antibodies and maytansinoids linked by a non-cleavable linker are known, others are new. Therefore there is provided a cell-binding agent maytansinoid conjugate having at least one maytansinoid linked to a cell-binding agent via a non-cleavable linker, provided that the linker does not comprise a group derived from a cross-linking agent selected from the group consisting of: succinimidyl 4-(N-maleimidomethyl)-cyclohexane-1-carboxylate (SMCC), sulfo-SMCC, m-maleimidobenzoyl-N-hydroxysuccinimide ester (MBS), sulfo-MBS, and succinimidlyl-iodoacetate when the cell-binding agent is an antibody.

The new conjugates can be made and used as described above.

The composition comprises the cell-binding agent maytansinoid conjugate and a carrier.

The carrier may be a pharmaceutically acceptable carrier, diluent or excipient.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

For these new conjugates, syntheses methods are also provided.

One of the processes of making the cell-binding agent maytansinoid conjugate comprises:
(a) providing the cell-binding agent
(b) modifying the cell-binding agent with a cross-linking agent, and
(c) conjugating the modified cell-binding agent with a maytansinoid or a thiol-containing maytansinoid thereby providing the non-cleavable linker between the cell-binding agent and the maytansinoid or thiol-containing maytansinoid to produce the conjugate.

Another process of making the cell-binding agent maytansinoid conjugate comprises:
(a) providing the maytansinoid or a thiol-containing maytansinoid,
(b) modifying the maytansinoid or thiol-containing maytansinoid with a cross-linking agent to thereby form a non-cleavable linker, and
(c) conjugating the modified maytansinoid or thiol-containing maytansinoid with the cell-binding agent, thereby providing the non-cleavable linker between the cell-binding agent and the maytansinoid or thiol-containing maytansinoid to produce the conjugate.

An additional process of making the cell-binding agent maytansinoid conjugate comprises:
(a) providing the maytansinoid,
(b) modifying the maytansinoid to provide a non-sulfur-containing maytansinol having an active ester, and
(c) conjugating the modified maytansinoid with the cell-binding agent, thereby providing a non-S-containing non-cleavable linker between the cell-binding agent and the maytansinol to produce the conjugate. These methods are described in detail above and in the United States patents cited herein and expressly incorporated herein by reference.

EXAMPLES

The invention will now be illustrated by reference to non-limiting examples. Unless otherwise stated, all percents, ratios, parts, etc. are by weight.

The buffers used in the following experiments were: 50 mM potassium phosphate (KPi)/50 mM sodium chloride (NaCl)/2 mM ethylenediaminetetraacetic acid (EDTA), pH 6.5 (Buffer A); 1× phosphate buffered saline (PBS), pH 6.5 (Buffer B); and 0.1 M KPi buffer/2 mM EDTA at pH 7.5 (Assay Buffer).

SMCC (Product No. 22360, M.W. 334.33 g/mole) and SIAB (Product No. 22329, M.W. 402.15 g/mole) were purchased from Pierce. The huC242 antibody is a humanized form of the monoclonal antibody C242, described in U.S. Pat. No. 5,552,293, for which the hybridoma is deposited with the ECACC Identification Number 90012601). Trastuzumab antibody was obtained from Genentech. DM1 (free thiol form; M.W. 737.5 g/mole) was prepared as-described previously in U.S. Pat. Nos. 5,208,020 and 6,333,410 B1.

Chromatography was performed using chromatography columns purchased from Amersham Biosciences (Sephadex G25 NAP-25 prepacked columns (Amersham 17-0852-02); HiPrep 26/10 Desalting Columns, Sephadex G25 fine resin, 3 connected in series (Amersham 17-5087-01)). TSK-GEL G3000SWXL chromatography columns (TOSOH Bioscience, 08541) were also used, with TSK Column Guard SW×1 (TOSOH Bioscience 08543).

Solvents used in the following experiments were dimethylsulfoxide (DMSO), dimethylacetamide (DMA), ethanol (EtOH), and 100 mM Ellman's Reagent (DTNB, available from Cayman Chemical) in DMSO.

Example 1A

Preparation of huC242-SMCC-DM1 Conjugate a. Preparation and Measurement of huC242 Antibody The concentration of antibody was measured using an extinction coefficient of 1.48 (mg/mL)$^{-1}$ at 280 nm and a molecular weight of 147,000 g/mole.

b. Preparation and Measurement of SMCC Stock Solution

A 20 mM solution of SMCC (6.69 mg/mL) was prepared in dimethylsulfoxide (DMSO). The solution was diluted 1/40 in Assay Buffer and the absorbance of the samples measured at 302 nm. The concentration of the stock solution was calculated using an extinction coefficient of 602 M$^{-1}$cm$^{-1}$.

c. Preparation and Measurement of DM1 Stock Solution

Figure 2:
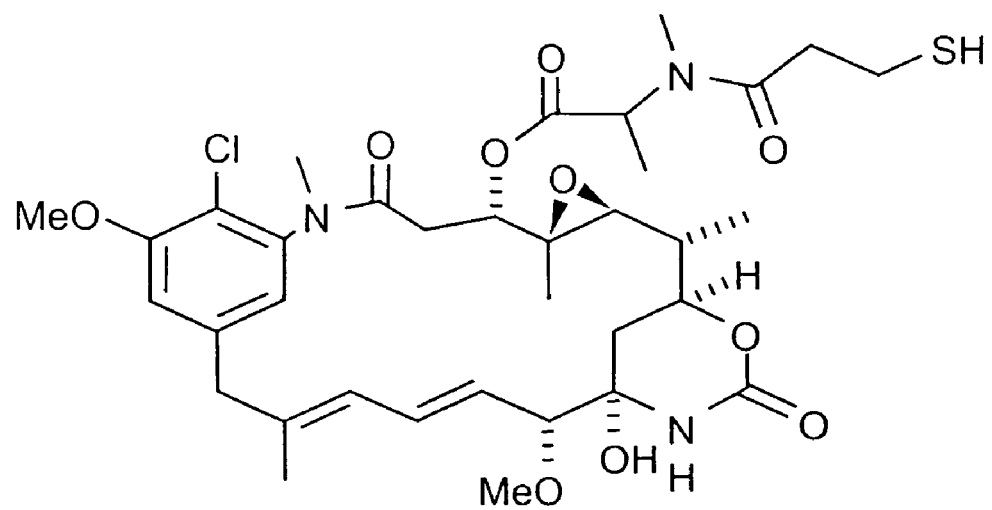
FIG. 2 shows the structure of DM1.

A 10 mM solution of DM1 (free thiol form) was prepared in dimethylacetamide (DMA) (7.37 mg/mL) (FIG. 2). The absorbance of dilutions of the stock solution in ethanol (EtOH) was measured at 280 nm. The concentration of stock DM1 was calculated by using an extinction coefficient of 5700 M$^{-1}$ at 280 nm. The concentration of free sulfhydryl or thiol groups (—SH) in the stock DM1 preparation was measured using Ellman's reagent (DTNB). Dilutions of the stock solution were prepared in Assay buffer made to 3% (v/v) DMA, and then 100 mM DTNB in DMSO (1/100th volume) was added. The increase in absorbance at 412 nm was measured against a reagent blank and the concentration was calculated using an extinction coefficient of 14150 M$^{-1}$cm$^{-1}$. The concentration of —SH resulting from the Ellman's assay was used to represent the DM1 stock concentration in calculations for conjugation conditions.

d. Modification of huC242 with SMCC Crosslinker

The antibody was split into two samples; one was modified using a 7.5-fold molar excess of SMCC cross-linker, the other with a 8.5-fold molar excess of SMCC cross-linker. Samples were reacted at 8 mg/mL antibody. The reactions were carried out in Buffer A (95% v/v) with DMSO (5% v/v) for 2 hours at room temperature with stirring.

e. G25 Chromatography to Remove Excess SMCC

The huC242-SMCC reaction mixtures were gel-filtered through 1.5×4.9 cm pre-packed columns of Sephadex G25 resin equilibrated in Buffer A. The load and elution volumes were according to manufacturer's instructions. The modified antibody elutions were assayed to determine the concentration of the antibody using the extinction co-efficient described above. The yield of modified antibody was 74.6% for the 7.5-fold molar excess SMCC reaction and 81.6% for the 8.5-fold molar excess SMCC reaction.

f. Conjugation of huC242-SMCC with DM1

The modified antibody samples were reacted with a 1.7-fold excess of DM1 over linker (assuming 5 linkers per antibody). The reactions were carried out at 2.5 mg/mL antibody concentration in Buffer A (97% v/v) with DMA (3% v/v). After addition of DM1, the reactions were incubated at room temperature for approximately 20 hours with stirring.

g. Conjugation Purification by G25 Chromatography

The conjugation reaction mixtures were gel-filtered through 1.5×4.9 cm pre-packed columns of Sephadex G25 resin equilibrated in Buffer B. The load and elution volumes were according to manufacturer's instructions. The number of DM1 molecules linked per mole of huC242 was determined by measuring absorbance of the eluted material at both 252 nm and 280 nm. The DM1/antibody ratio for the 7.5-fold molar excess SMCC sample was found to be 3.54 and the ratio for the 8.5-fold molar excess SMCC sample was found to be 3.65. The conjugation step yields were 83.7% and 75.4%, respectively. Both conjugates were pooled together, sterile-filtered, and re-assayed for drug and antibody concentrations. The pooled sample was assigned Lot #1713-146C and analyzed for binding, cytotoxicity, specificity, extent of aggregation and free drug content.

TABLE I

Characteristics of huC242-SMCC-DM1

| Reference Number | Final Protein Conc. (mg/ml) | Final DM1 Conc. (ug/ml) | DM1/Ab |
| --- | --- | --- | --- |
| 1713-146C | 1.77 | 26.96 | 3.05 |

Example 1B

In Vitro Testing of huC242-SMCC-DM1 a. Binding

Figure 3:
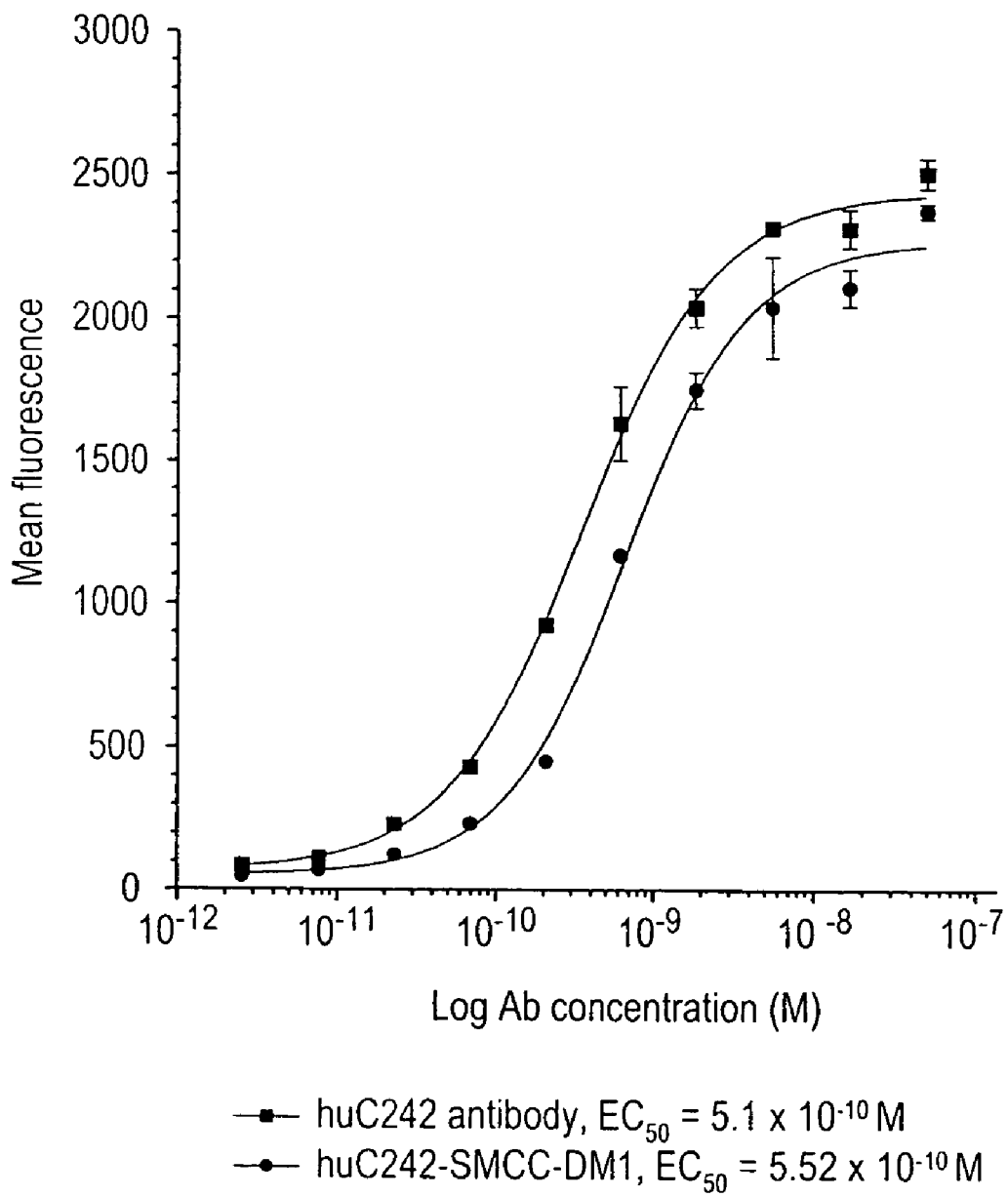
FIG. 3 shows graphically results of a FACS binding assay comparing huC242 antibody to the antibody-maytansinoid conjugate huC242-SMCC-DM1.

The binding affinities of huC242 antibody and huC242-SMCC-DM1 were compared using an indirect method on COLO 205 cells, where 5×10³ cells per well were used, with a three hour primary incubation on ice. The results are shown in FIG. 3. The naked antibody bound with a KD of $5.1 \times 10^{-10}$ M and the conjugated version bound with a KD of $5.52 \times 10^{-10}$ M. Thus, conjugation with DM1 does not appear to alter the binding affinity of huC242.

b. Cytotoxicity and Specificity

The in vitro cytotoxicity and specificity of the huC242-SMCC-DM1 conjugate were evaluated using a continuous exposure clonogenic assay. The results are shown in FIG. 4. HuC242-SMCC-DM1 was effective in destroying the antigen-positive SKBR3 cells ($IC_{50} = 3.5 \times 10^{-12}$ M). Specificity was shown by comparing the $IC_{50}$ value of the target SKBR3 cells to that of the antigen-negative cell line, A375, in which the $IC_{50}$ of the conjugate was greater than $3.0 \times 10^{-9}$ M.

c. Size Exclusion Chromatography Analysis

Figure 5:
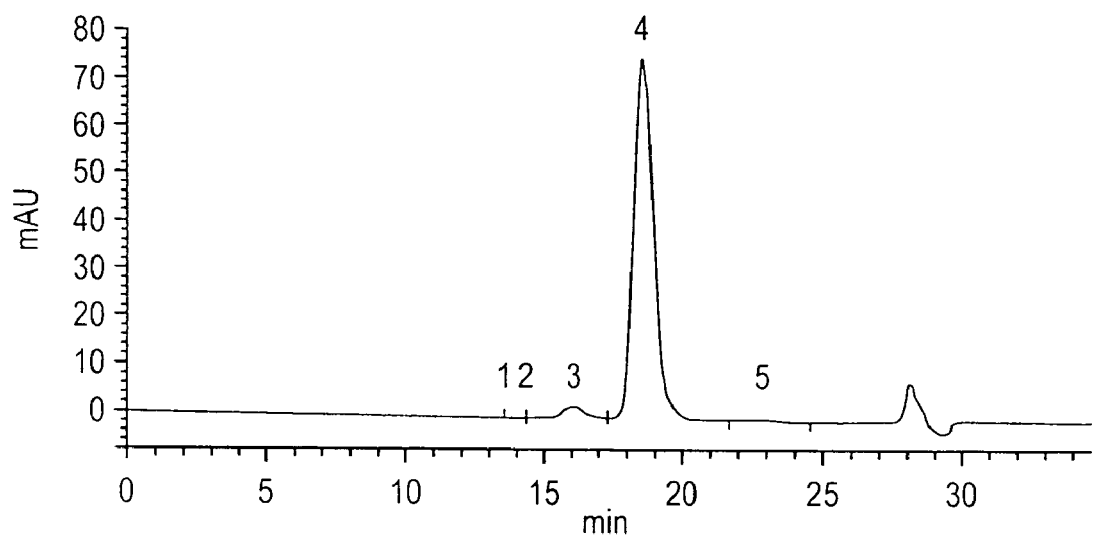
FIG. 5 shows size exclusion chromatography for huC242-SMCC-DM1. Peaks 1 and 2 represent high molecular weight aggregates, peak 3 represents dimeric conjugate, peak 4 represents monomeric conjugate and peak 5 represents low molecular weight antibody fragments. The peak eluting after peak 5 (at 28 minutes) represents buffer salts.

The conjugate was analyzed using a TSK3000 size exclusion column (FIG. 5). Peak 4 represents the monomer fraction of the conjugate while earlier peaks represent multimer and later peaks represent fragment. The area under each curve divided by total peak areas represents the peak's contribution to the sample. The conjugate sample was found to be 96.0% monomer.

d. Free Drug

The percent of free drug was measured by ELISA and was found to be 4.4%.

Example 2A

Preparation of Trastuzumab-SMCC-DM1 Conjugate

Trastuzumab antibody was obtained from Genentech for conjugation to DM1 using the non-cleavable heterobifunctional cross-linking reagent SMCC. The antibody was buffer-exchanged from 50 mM potassium phosphate/2 mM EDTA, pH 6.0 into 50 mM potassium phosphate/50 mM sodium chloride/2 mM EDTA, pH 6.5 (Buffer A). The antibody was then reacted with 7.5-fold molar excess SMCC linker and purified by Sephadex G25 resin before it was conjugated with DM1. The final conjugate was again purified by Sephadex G25 resin. The resulting conjugate contained 3.1 moles of DM1 per mole of antibody.

a. Preparation and Measurement of Trastuzumab Antibody

Trastuzumab antibody in 50 mM potassium phosphate/2 mM EDTA, pH 6.0 buffer was passed over a Sephadex G25 column equilibrated with Buffer A and eluted into Buffer A. All buffers used in this experiment were tested to be free of endotoxin using a chromogenic Lymulus amoebocyte lysate (LAL) method (Cambrex). The concentration of antibody was measured using an extinction coefficient of 1.45 mL mg$^{-1}$ cm$^{-1}$ at 280 nm and a molecular weight of 145,423 g.

b. Preparation and Measurement of SMCC Stock Solution

A 20 mM solution of SMCC (6.69 mg/mL) was prepared in DMSO. The solution was diluted 1/40 in Assay Buffer and the absorbance of the samples was measured at 302 nm. The concentration of the stock solution was calculated using a molar extinction coefficient of 602 M$^{-1}$ cm$^{-1}$.

c. Preparation and Measurement of DM1 Stock Solution

A 10 mM solution of DM1 (free thiol form) was prepared in DMA (7.37 mg/mL) (FIG. 2). The absorbance of dilutions of the stock solution in EtOH was measured at 280 nm. The concentration of stock DM1 was calculated by using a molar extinction coefficient of 5700 M$^{-1}$ cm$^{-1}$ at 280 nm. The concentration of free —SH in the stock DM1 preparation was measured using Ellman's reagent (DTNB). Dilutions of the stock solution were prepared in Assay buffer made to 3% (v/v) DMA, and then 100 mM DTNB in DMSO (1/100$^{th}$ volume) was added. The increase in absorbance at 412 nm was measured against a reagent blank and the concentration was calculated using an extinction coefficient of 14150 M$^{-1}$ cm$^{-1}$. The concentration of —SH resulting from the Ellman's assay was used to represent the DM1 stock concentration in calculations for conjugation conditions.

d. Modification of Trastuzumab with SMCC Crosslinker

The antibody was modified using a 7.5-fold molar excess of SMCC at 20 mg/mL antibody. The reaction was carried out in Buffer A (95% v/v) with DMSO (5% v/v) for 2 hours at room temperature with stirring.

e. G25 Chromatography to Remove Excess SMCC

The trastuzumab-SMCC reaction mixture was gel-filtered through a 1.5×4.9 cm pre-packed column of Sephadex G25 resin equilibrated in Buffer A. The load and elution volumes were according to manufacturer's instructions (Amersham Biosciences). The concentration of the modified antibody solution was assayed spectrophotometrically using the extinction co-efficient described above. The yield of modified antibody was 88% based on protein concentration.

f. Conjugation of Trastuzumab-SMCC with DM1

The modified antibody was reacted with a 1.7-fold excess of DM1 over linker (assuming 5 linkers per antibody). The reaction was carried out at 10 mg/mL antibody concentration in Buffer A (94% v/v) with DMA (6% v/v). After addition of DM1, the reaction was incubated at room temperature for 16.5 hours with stirring.

g. Conjugation Purification by G25 Chromatography

The conjugation reaction mixture was gel-filtered through a 1.5×4.9 cm pre-packed column of Sephadex G25 resin equilibrated in Buffer B. The load and elution volumes were according to manufacturer's instructions (Amersham Biosciences). The number of DM1 molecules linked per mole of trastuzumab was determined by measuring absorbance at both 252 nm and 280 nm of the eluted material. The DM1/antibody ratio was found to be 3.13 and the conjugation step yield was 95.7%. The overall yield of conjugated trastuzumab was 84% based on the starting antibody. The resulting conjugate was analyzed for binding, cytotoxicity, specificity, extent of aggregation and free drug content.

TABLE II

Characteristics of Trastuzumab-SMCC-DM1

| Reference Number | Final Protein Conc. (mg/ml) | Final DM1 Conc. (ug/ml) | DM1/Ab |
|---|---|---|---|
| 1762-14 | 6.71 | 106. | 3.13 |

Example 2B

In Vitro Testing of Trastuzumab-SMCC-DM1

Binding studies showed that the conjugation of antibody to DM1 did not affect the apparent $K_D$; both naked trastuzumab antibody and trastuzumab-SMCC-DM1 conjugate had the same binding affinity to ECD plates ($5.5 \times 10^{-11}$ M). Evaluation of the in vitro cytotoxicity of the sample showed that the trastuzumab-SMCC-DM1 conjugate is both highly toxic ($IC_{50}$ $3.6 \times 10^{-12}$ M on antigen-positive cell line) and specific ($IC_{50}$ greater than $3.0 \times 10^{-9}$ M on antigen-negative cell line).

a. Binding

Figure 24:
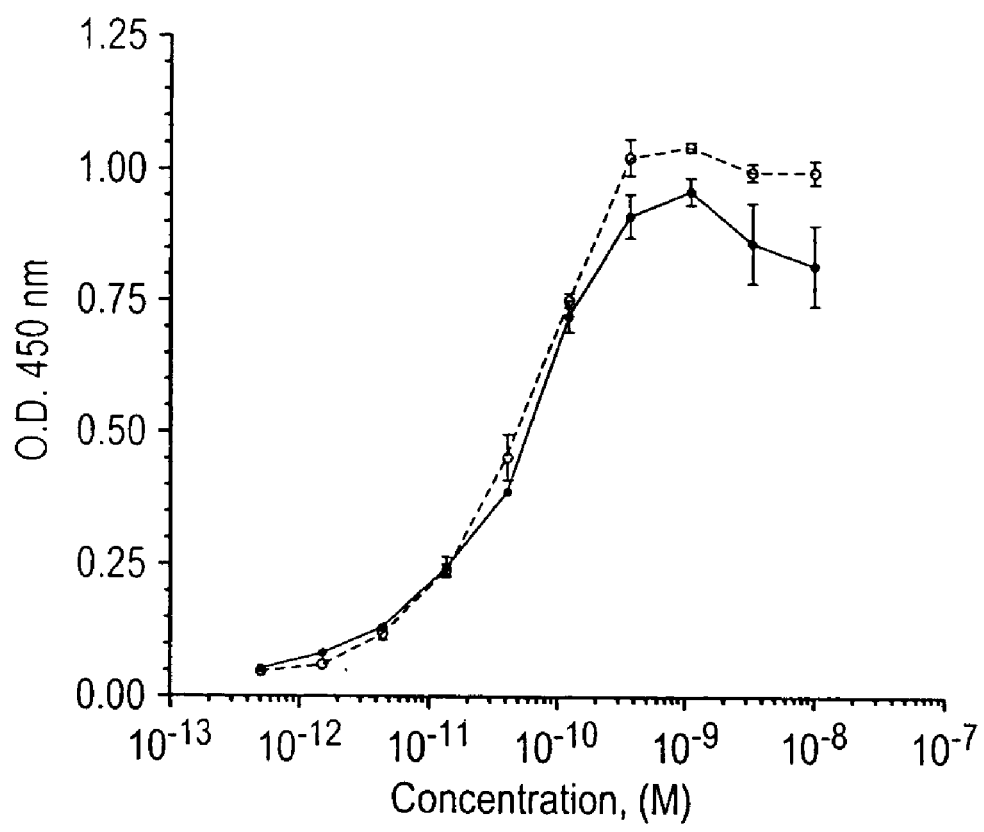
FIG. 24 shows graphically results of a HER2 ECD plate-binding assay comparing trastuzumab antibody to the antibody-maytansinoid conjugate trastuzumab-SMCC-DM1.

The binding affinity of trastuzumab antibody and trastuzumab-SMCC-DM1 were compared using the HER2 ECD plate-binding assay provided by Genentech. The results are shown in FIG. 24. Both the naked antibody and conjugated version bind with an apparent $K_D$ of $5.5 \times 10^{-11}$M. Thus, conjugation with DM1 does not alter the binding affinity of trastuzumab.

b. Cytotoxicity and Specificity

Figure 25:
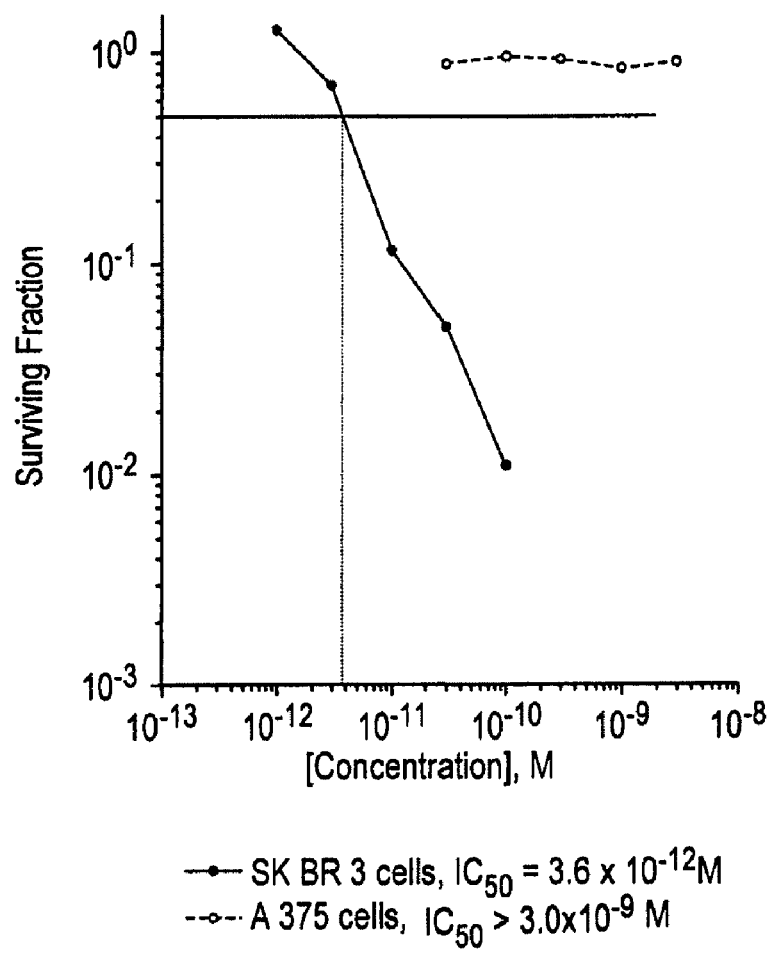
FIG. 25 shows graphically the cytotoxicity and specificity of trastuzumab-SMCC-DM1.

The in vitro cytotoxicity and specificity of the trastuzumab-SMCC-DM1 conjugate were evaluated using a continuous exposure clonogenic assay. The results are shown in FIG. 25. Trastuzumab-SMCC-DM1 was effective in destroying the antigen-positive SKBR3 cells ($IC_{50}=3.6 \times 10^{-12}$ M). Specificity was shown when comparing the $IC_{50}$ of the target SKBR3 cells to the antigen-negative cell line, A375, in which the $IC_{50}$ of the conjugate was greater than $3.0 \times 10^{-9}$ M.

c. Size Exclusion Chromatography Analysis

Figure 26:
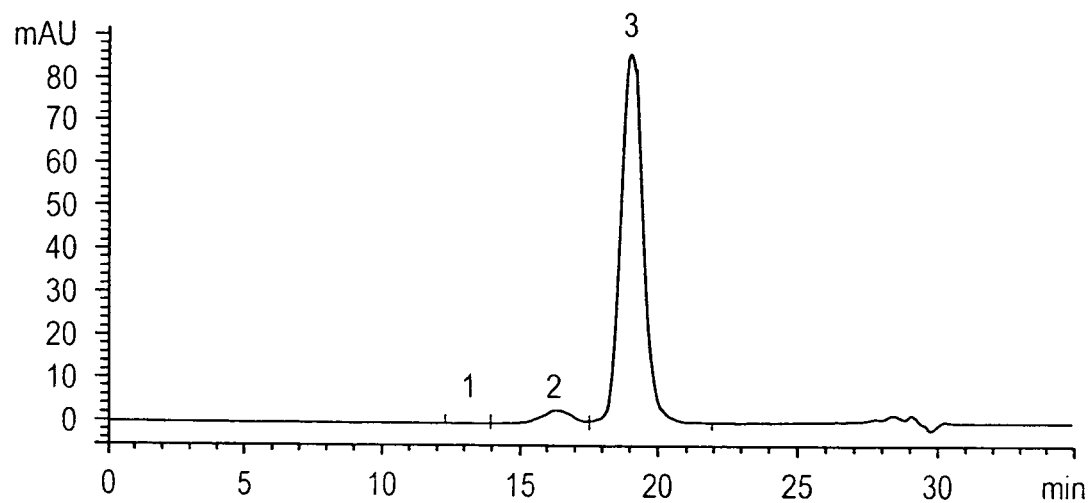
FIG. 26 shows size exclusion chromatography for trastuzumab-SMCC-DM1. Peak 1 represents high molecular weight aggregates, peak 2 represents dimeric conjugate and peak 3 represents monomeric conjugate. The peak eluting after peak 3 (at 28 minutes) represents buffer salts.

The conjugate was analyzed using a TSK3000 size exclusion column (FIG. 26). Peak 1 represents multimer, peak 2 represents dimer, and peak 3 represents monomer. The area under each curve divided by total peak areas represents the peak's contribution to the sample. The conjugate sample was found to be 95.3% monomer.

d. Free Drug Analysis

The percent free drug was measured by ELISA and found to be 3.4%.

e. Endotoxin Level

The conjugate was tested using a chromatographic LAL test and found to contain 0.03 EU/mg.

Example 3A

Preparation of Trastuzumab-SIAB-DM1 Conjugate

Trastuzumab antibody was obtained from Genentech for conjugation to DM1 using the non-cleavable heterobifunctional crosslinker SIAB. The antibody was reacted with 7.0-fold molar excess SIAB linker at pH 6.5 and purified by Sephadex G25F resin. Antibody containing fractions were pooled and reacted with DM1 overnight at standard conjugation conditions of pH 6.5 and room temperature but in the dark. An aliquot was removed from the reaction vessel and analyzed to determine incorporation of DM1. The aliquot was measured after a NAP 5 filtration to have only 1.4 drugs/Ab. An additional 8-fold excess of SIAB was added to the reaction for 2 hours and then the pH was increased to 8 just prior to the addition of an additional 1.5-fold excess DM1/SIAB. The reaction was allowed to proceed and was purified using Sepahadex G25F resin. The resulting conjugate contained 3.42 moles of DM1 per mole of antibody.

a. Measurement of Trastuzumab Antibody

The concentration of antibody was measured using an extinction coefficient of 1.45 mL mg$^{-1}$ cm$^{-1}$ at 280 nm and a molecular weight of 145,423 g.

b. Preparation and Measurement of SIAB Stock Solution

An 18 mM solution of SIAB (7.2 mg/mL) was prepared in DMSO. A wavelength scan of the solution diluted into pH 4 buffer was recorded for informational purposes only.

c. Preparation and Measurement of DM1 Stock Solution

An approximately 30 mM solution of DM1 (free thiol form) was prepared in DMA. The concentration of free —SH in the stock DM1 preparation was measured using Ellman's reagent (DTNB). Dilutions of the stock solution were prepared in Assay buffer made to 3% (v/v) DMA, and then 100 mM DTNB in DMSO ($\frac{1}{100}^{th}$ volume) was added. The increase in absorbance at 412 nm was measured against a reagent blank and the concentration was calculated using a molar extinction coefficient of 14150 M$^{-1}$ cm$^{-1}$. The concentration of —SH resulting from the Ellman's assay was used to represent the DM1 stock concentration in calculations for conjugation conditions.

d. Modification of Trastuzumab with SIAB Cross Linker

The antibody was modified using a 7.0-fold molar excess of SIAB at 20 mg/mL antibody. The reaction was carried out in Buffer A (95% v/v) with DMSO (5% v/v) for 2 hours at room temperature with stirring in the dark.

e. G25 Chromatography to Remove Excess SIAB

The Trastuzumab-SIAB reaction mixture was gel-filtered through HiPrep 26/10 Desalting Columns equilibrated in Buffer A. There appeared to be interference at 280 nm from the SIAB reagent, so the yield of modified antibody was assumed to be 100% and a modification of 5 linkers/antibody was assumed for determination of the amount of DM1 in the conjugation reaction.

f. Conjugation of Trastuzumab-SIAB with DM1

The modified antibody was reacted with a 1.7-fold excess of DM1 over linker assuming 100% yield and 5 cross-linkers/antibody as stated above. The concentration of antibody in the reaction was estimated to be 12.5 mg/mL and the reaction was carried out in Buffer A (97% v/v) with DMA (3% v/v). After addition of DM1, the reaction was incubated at room temperature in the dark for 16.5 hours with stirring.

g. Conjugation Reaction Analysis

A 0.25 mL aliquot of the reaction mixture was removed and gel-filtered over a prepacked G25 Sephadex column equilibrated in Buffer B. The number of DM1 molecules linked per mole of trastuzumab was determined by measuring absorbance at both 252 nm and 280 nm of the eluted material. The DM1/antibody ratio was only 1.4.

h. Additional Modification/Conjugation Reaction

An additional 8-fold molar excess of SIAB was added and allowed to incubate for 2 hours at room temperature. A 1.5 fold molar excess of DM1 over SIAB was added and the pH of the reaction was increased to 8 with the addition of 1 N NaOH. The reaction was incubated at room temperature in the dark and gel-filtered over a column of G25F resin equilibrated into Buffer B.

i. Pooling and Characterization of Conjugate

Protein containing fractions were pooled, filtered and measured by absorbance at 252 and 280 nm. Samples of the conjugate were tested for endotoxin level, binding, specific and non-specific cytotoxicity, % monomer and free drug level.

TABLE III

Characteristics of Trastuzumab-SIAB-DM1

| Reference Number | Final Protein Conc. (mg/ml) | Final DM1 Conc. (ug/ml) | DM1/Ab |
|---|---|---|---|
| 1806-32 | 5.62 | 97.3 | 3.42 |

Example 3B

In Vitro Testing of Trastuzumab-SIAB-DM1

Binding studies showed that the conjugation of antibody to DM1 did not affect the apparent $K_D$; both naked trastuzumab and trastuzumab-SIAB-DM1 had a similar binding affinities ($1.2\times10^{-10}$M Ab and $1.9\times10^{-10}$M apparent $K_D$ conjugate). Evaluation of the in vitro cytotoxicity of the sample showed that the trastuzumab-SLAB-DM1 conjugate is both highly toxic ($IC_{50}$ $5\times10^{-12}$M on antigen-positive cell line SKBR3) and specific ($IC_{50}$ greater than $3.0\times10^{-9}$M on antigen-negative cell line, A375).

a. Binding

Figure 27:
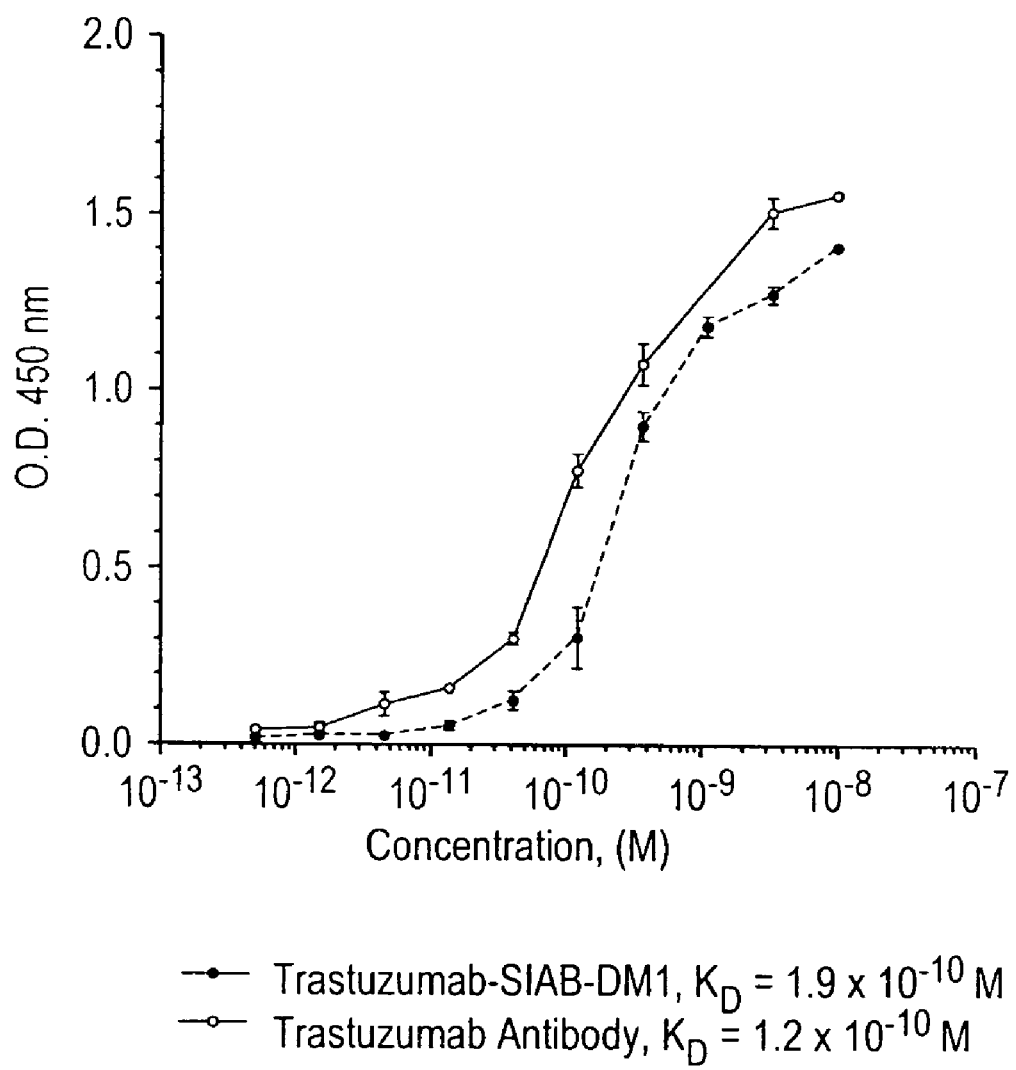
FIG. 27 shows graphically results of a HER2 ECD plate-binding assay comparing trastuzumab antibody to the antibody-maytansinoid conjugate trastuzumab-SIAB-DM1.

The binding affinity of trastuzumab antibody and trastuzumab-SIAB-DM1 were compared using the HER2 ECD plate binding assay provided by Genentech. The results are shown in FIG. 27. Naked trastuzumab and trastuzumab-SIAB-DM1 had similar binding affinities ($1.2\times10^{-10}$M for the antibody and $1.9\times10^{-10}$M apparent $K_D$ for the conjugate).

b. Cytotoxicity and Specificity

Evaluation of the in vitro cytotoxicity of the sample showed that the trastuzumab-SIAB-DM1 conjugate is both highly toxic ($IC_{50}=5\times10^{-12}$M on antigen-positive cell line, SKBR3) and specific ($IC_{50}$ greater than $3.0\times10^{-9}$M on antigen-negative cell line, A375). See FIG. 28.

c. Size Exclusion Chromatography Analysis

Figure 29:
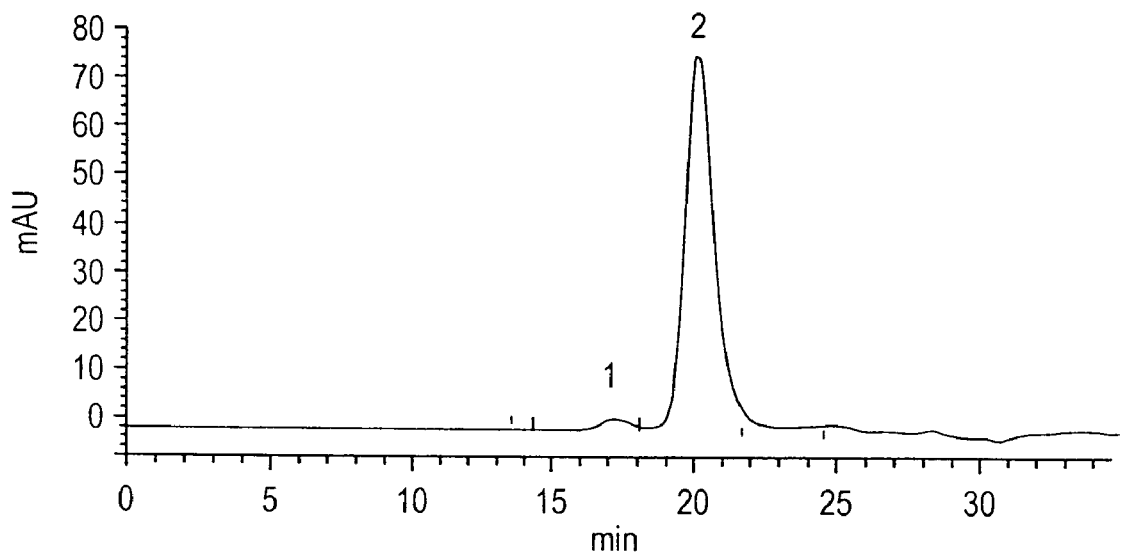
FIG. 29 shows size exclusion chromatography for trastuzumab-SIAB-DM1. Peak 1 represents dimeric conjugate and peak 2 represents monomeric conjugate.

The conjugate was analyzed using a TSK3000 size exclusion column (FIG. 29). Peak 1 represents dimer and peak 2 represents monomer. The area under each curve divided by total peak area represents the peak's contribution to the sample. The conjugate sample was found to be 96.4% monomer.

d. Free Drug

The percent of free drug was measured by ELISA and was found to be 0.35%.

e. Endotoxin Level

The conjugate was tested using a chromatographic LAL test and found to contain <0.04 EU/mg.

Example 4

Conjugation of HuC242 with a Cross-Linking Reagent that Forms a Non-S-Containing Non-Cleavable Linker a. Synthesis A stock solution of the cross-linking reagent (see FIG. 21 for structure) was made up in DMA, insoluble precipitate was spun out, and the concentration of the remaining solution was determined using an extinction coefficient of $\epsilon^{280}=5700$ $M^{-1}cm^{-1}$ which is the extinction for DM1 at this wavelength. Since the real extinction coefficient for this material has not been measured this is only an estimate of concentration. It should be noted that the ratio $\epsilon^{252}/\epsilon^{280}$ for DM1 is 4.7 (in ETOH) while $\epsilon^{252}/\epsilon^{280}$ for this cross-linking reagent solution (in pH 7.5 buffer) was measured as 1.42 suggesting either different extinctions or impurities.

The conjugation reaction was carried out on a 2 mg scale using 2.8 mg/ml huC242 antibody in 16% DMA in Buffer E, pH 7.5 (Buffer E=50 mM sodium phosphate, 150 mM NaCl, 10 mM EDTA). Based on the estimated cross-linking reagent concentration of the stock solution, 30 equivalents of cross-linker/antibody were used (an earlier experiment using 10 eq. of cross-linker/antibody produced a conjugate with only 0.9 DM1/antibody). The reaction was allowed to go for 3 hours and then the conjugate was purified by passage over a Nap 10 (G25) column. After filtering (Millex GV filter, 0.2 um pore size), the conjugate had 2.56 DM1/antibody (Lot #1749-119A, antibody recovery=78%). An aliquot of the conjugate was examined by HPLC (HiPrep column) for free DM1 and a sizeable DM1 peak was observed at 12.09'. The sample was therefore dialyzed in Buffer B to get rid of this peak and then reassayed. The final conjugate sample (Lot #1749-124A) had no free DM1 by HPLC and had 1.84 DM1/antibody. SEC HPLC was carried out on the conjugate to show that it was 97% monomeric antibody.

b. Cytotoxicity and Binding

Figure 23:
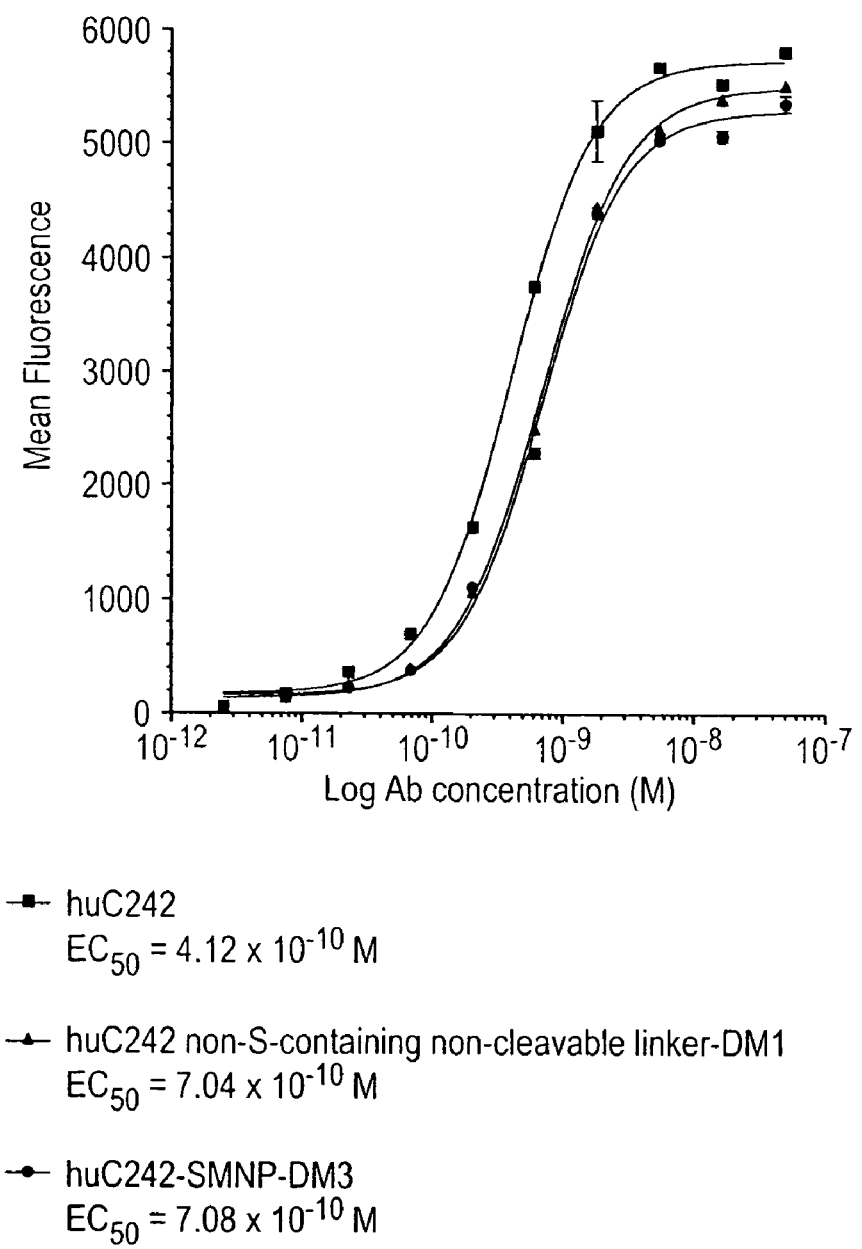
FIG. 23 shows graphically results of a FACS binding assay of huC242-non-S-containing non-cleavable linker-DM1.

The inventors carried out binding and cytotoxicity studies on the huC242-non-S-containing non-cleavable linker-DM1 conjugate. First, the binding affinities of huC242 antibody, huC242-SMNP-DM3, and huC242-non-S-containing non-cleavable linker-DM1 to COLO 205 cells were compared. $5\times10^3$ cells per well were used, with a three hour primary incubation on ice. The results are shown in FIG. 23. The huC242-non-S-containing non-cleavable linker-DM1 conjugate had about a two-fold higher apparent dissociation constant than free antibody (see FIG. 23). In addition, the huC242-non-S-containing non-cleavable linker-DM1 conjugate had an in vitro cytotoxicity comparable to huC242-SMNP-DM3 ($IC_{50}$ of the non-S-containing non-cleavable linker conjugate=$7.0\times10^{-12}$ M) (see FIG. 22).

While the invention has been described in detail and with reference to specific embodiments thereof, it will be apparent to one skilled in the art that various changes and modifications can be made therein without departing from the spirit and scope of the invention.

All patents, publications, and other references cited herein are expressly incorporated by reference in their entireties.

What is claimed is:

1. A method for targeting maytansinoids to a selected cell population in vivo, the method comprising contacting a cell population or tissue suspected of containing the selected cell population with a cell-binding agent maytansinoid conjugate, wherein one or more maytansinoids is covalently linked to the cell-binding agent via a non-cleavable linker and the cell-binding agent binds to cells of the selected cell population,
wherein the cell-binding agent is an antibody, a single chain antibody or an antibody fragment that specifically bind to a target cell, wherein at least a constant region of the antibody, single chain antibody or antibody fragment comprises a human antibody sequence, and, provided that the cell-binding agent is not an anti-erbB antibody.

2. The method of claim 1, wherein the non-cleavable linker is substantially resistant to acid-induced cleavage, light-induced cleavage, peptidase-induced cleavage, esterase-induced cleavage, and disulfide bond cleavage.

3. The method of claim 1, wherein the non-cleavable linker has a sulfur atom.

4. The method of claim 3, wherein the non-cleavable linker is derived from a maleimido-based moiety.

5. The method of claim 4, wherein the non-cleavable linker is derived from a maleimido-based moiety selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidcaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), and N-(p-maleimidophenyl)isocyanate (PMPI).

6. The method of claim 5, wherein the non-cleavable linker is derived from SMCC.

7. The method of claim 3, wherein the non-cleavable linker is derived from a haloacetyl-based moiety.

8. The method of claim 7, wherein the non-cleavable linker is derived from a haloacetyl-based moiety selected from the group consisting of N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

9. The method of claim 8, wherein the non-cleavable linker is derived from SIAB.

10. The method of claim 1, wherein the linker is at any one of the C-3 hydroxyl, C-14 hydroxymethyl, C-15 hydroxyl or C-20 desmethyl groups of the at least one maytansinoid.

11. The method of claim 1, wherein the at least one maytansinoid is an N-methyl-alanine-containing ester of maytansinol.

12. The method of claim 1, wherein the at least one maytansinoid is an N-methyl-cysteine-containing ester of maytansinol.

13. The method of claim 1, wherein the at least one maytansinoid is represented by formula (II'-L), (II'-D) or (II'-D, L):

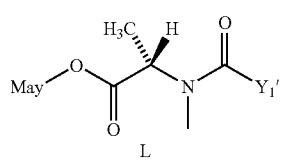

(II')

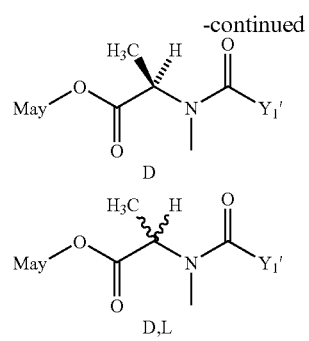

wherein:
$Y_1'$ represents $(CR_7R_8)_l(CR_9=CR_{10})_p(C\equiv C)_qA_o(CR_5R_6)_mD_u(CR_{11}=CR_{12})_r(C\equiv C)_sB_t(CR_3C_4)_nCR_1R_2S-$,
wherein:
$R_1$ to $R_{12}$ are each independently linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition, $R_2$ to $R_{12}$ can be H;
A, B, and D, each independently is cyclic alkyl or cyclic alkenyl having 3 to 10 carbon atoms, simple or substituted aryl, or heterocyclic aromatic or heterocycloalkyl radical;
l, m, n, o, p, q, r, s, t and u are each independently 0 or an integer of 1 to 5, provided that at least two of l, m, n, o, p, q, r, s, t and u are not both zero; and
May represents a maytansinoid that bears a side chain at C-3 hydroxyl, C-14 hydroxymethyl, C-15 hydroxyl or C-20 desmethyl.

14. The method of claim 13, wherein $R_1$ is methyl and $R_2$ is H or $R_1$ and $R_2$ are methyl.

15. The method of claim 13, wherein $R_1$ is methyl, $R_2$ is H, $R_5$, $R_6$, $R_7$ and $R_8$ are each H, l and m are each 1, and n is 0; or wherein $R_1$ and $R_2$ are methyl, $R_5$, $R_6$, $R_7$, $R_8$ are each H, l and m are 1, and n is 0.

16. The method of claim 1, wherein the at least one maytansinoid is represented by formula (II-L), (II-D), or (II-D,L):

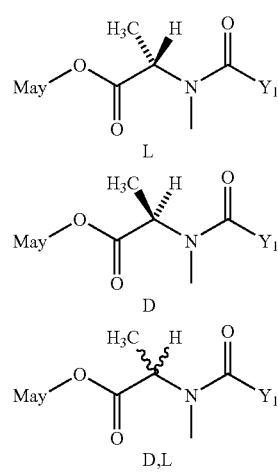

(II)

wherein:
$Y_1$ represents $(CR_7R_8)_l(CR_5R_6)_m(CR_3R_4)_nCR_1R_2S-$,
wherein:

$R_1$ to $R_8$ are each independently, linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition $R_2$ to $R_8$ can be H;

l, m and n are each independently an integer of 1 to 5, and in addition n can be 0; and May represents a maytansinoid that bears the side chain at C-3 hydroxyl, C-14 hydroxymethyl, C-15 hydroxyl or C-20 desmethyl.

17. The method of claim 16, wherein $R_1$ is methyl and $R_2$ is H or $R_1$ and $R_2$ are methyl.

18. The method of claim 16, wherein $R_1$ is methyl, $R_2$ is H, $R_5$, $R_6$, $R_7$ and $R_8$ are each H, l and m are each 1, and n is 0; or wherein $R_1$ and $R_2$ are methyl, $R_5$, $R_6$, $R_7$, $R_8$ are each H, l and m are 1, and n is 0.

19. The method of claim 1, wherein the at least one maytansinoid is represented by formula 41':

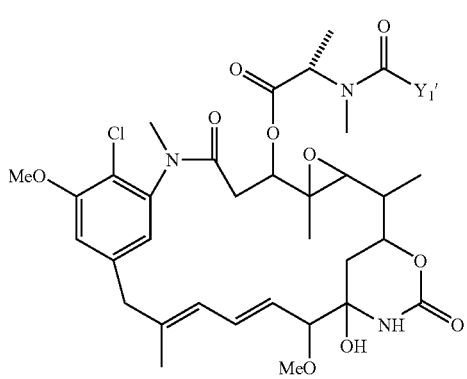

41' wherein:

$Y_1'$ represents
$(CR_7R_8)_l(CR_9=CR_{10})_p(C≡C)_qA_o(CR_5R_6)_mD_u(CR_{11}=CR_{12})_r(C≡C)_sB_t(CR_3R_4)_nCR_1R_2S—$, wherein:

$R_1$ to $R_{12}$ are each independently linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition, $R_2$ to $R_{12}$ can be H;

A, B, and D, each independently is cyclic alkyl or cyclic alkenyl having 3 to 10 carbon atoms, simple or substituted aryl, or heterocyclic aromatic or heterocycloalkyl radical; and l, m, n, o, p, q, r, s, t and u are each independently 0 or an integer of 1 to 5, provided that at least two of l, m, n, o, p, q, r, s, t and u are not both zero.

20. The method of claim 19, wherein $R_1$ is methyl and $R_2$ is H or $R_1$ and $R_2$ are methyl.

21. The method of claim 19, wherein $R_1$ is methyl, $R_2$ is H, $R_5$, $R_6$, $R_7$ and $R_8$ are each H, l and m are each 1, and n is 0; or wherein $R_1$ and $R_2$ are methyl, $R_5$, $R_6$, $R_7$, $R_8$ are each H, l and m are 1, and n is 0.

22. The method of claim 1, wherein the at least one maytansinoid is represented by formula 41:

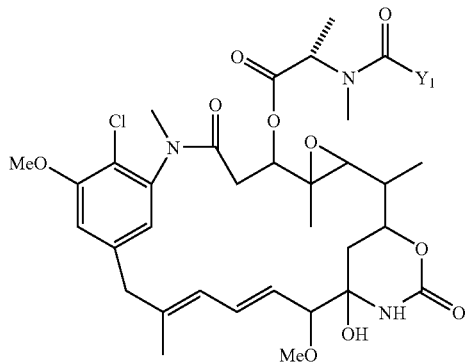

41 wherein:

$Y_1$ represents $(CR_7R_8)_l(CR_5R_6)_m(CR_3R_4)_nCR_1R_2S—$, wherein:

$R_1$ to $R_8$ are each independently, linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition $R_2$ to $R_8$ can be H; and l, m and n are each independently an integer of 1 to 5, and in addition n can be 0.

23. The method of claim 22, wherein $R_1$ is methyl and $R_2$ is H or $R_1$ and $R_2$ are methyl.

24. The method of claim 22, wherein $R_1$ is methyl, $R_2$ is H, $R_5$, $R_6$, $R_7$ and $R_8$ are each H, l and m are each 1, and n is 0; or wherein $R_1$ and $R_2$ are methyl, $R_5$, $R_6$, $R_7$, $R_8$ are each H, l and m are 1, and n is 0.

25. The method of claim 1, wherein the at least one maytansinoid is $N^{2'}$-deacetyl-$N^{2'}$-(3-mercapto-1-oxopropyl)-maytansine (DM1).

26. The method of claim 1, wherein the at least one maytansinoid is $N^{2'}$-deacetyl-$N^{2'}$-(4-mercapto-1-oxopentyl)-maytansine (DM3).

27. The method of claim 1, wherein the at least one maytansinoid is $N^{2'}$-deacetyl-$N^{2'}$-(4-methyl-4-mercapto-1-oxopentyl)-maytansine (DM4).

28. The method of claim 1, wherein the cell-binding agent binds to tumor cells; virus infected cells, microorganism infected cells, parasite infected cells, autoimmune cells, activated cells in graft rejection or graft vs. host disease, myeloid cells, activated T-cells, B cells, or melanocytes; cells expressing the CD33, CD19, CanAg, or CALLA antigens; or cells expressing insulin growth factor receptor or folate receptor.

29. The method of claim 1, wherein the cell-binding agent binds to breast cancer cells, kidney cancer cells, lung cancer cells, prostate cancer cells, ovarian cancer cells, colorectal cancer cells, gastric cancer cells, squamous cancer cells, small-cell lung cancer cells, non-small-cell lung cancer cells, pancreatic cancer cells, testicular cancer cells, neuroblastoma cells, melanoma cells, cells from cancer of the lymphatic organs or a combination thereof.

30. The method of claim 1, wherein the cell-binding agent is said resurfaced antibody, said resurfaced single chain antibody, or said resurfaced antibody fragment that specifically bind to a target cell.

31. The method of claim 1, wherein the cell-binding agent is a humanized antibody, a humanized single chain antibody, or a humanized antibody fragment that specifically binds to a target cell.

32. The method of claim 1, wherein the cell-binding agent is a resurfaced monoclonal antibody, a resurfaced single chain monoclonal antibody, or a resurfaced monoclonal antibody fragment that specifically bind to a target cell.

33. The method of claim 1, wherein the cell-binding agent is a humanized monoclonal antibody, a humanized single chain monoclonal antibody, or a humanized monoclonal antibody fragment that specifically bind to a target cell.

34. The method of claim 1, wherein the cell-binding agent is a resurfaced monoclonal antibody, a resurfaced single chain monoclonal antibody, or a resurfaced monoclonal antibody fragment that specifically bind to tumor cells.

35. The method of claim 1, wherein the cell-binding agent is a humanized monoclonal antibody, a humanized single chain monoclonal antibody, or a humanized monoclonal antibody fragment that specifically bind to tumor cells.

36. The method of claim 1, wherein the cell-binding agent is a resurfaced monoclonal antibody, a resurfaced single chain monoclonal antibody, or a resurfaced monoclonal antibody fragment that specifically bind to colorectal cancer cells, breast cancer cells, kidney cancer cells, lung cancer cells, prostate cancer cells, ovarian cancer cells, gastric cancer cells, squamous cancer cells, small-cell lung cancer cells, non-small-cell lung cancer cells, pancreatic cancer cells, testicular cancer cells, neuroblastoma cells, melanoma cells, cells from cancer of the lymphatic organs or a combination thereof.

37. The method of claim 1, wherein the cell-binding agent is a humanized monoclonal antibody, a humanized single chain monoclonal antibody, or a humanized monoclonal antibody fragment that specifically bind to colorectal cancer cells, breast cancer cells, kidney cancer cells, lung cancer cells, prostate cancer cells, ovarian cancer cells, gastric cancer cells, squamous cancer cells, small-cell lung cancer cells, non-small-cell lung cancer cells, pancreatic cancer cells, testicular cancer cells, neuroblastoma cells, melanoma cells, cells from cancer of the lymphatic organs or a combination thereof.

38. The method of claim 1, wherein the cell-binding agent is a resurfaced monoclonal antibody, a resurfaced single chain monoclonal antibody, or a resurfaced monoclonal antibody fragment that specifically bind to breast cancer cells.

39. The method of claim 1, wherein the cell-binding agent is a humanized monoclonal antibody, a humanized single chain monoclonal antibody, or a humanized monoclonal antibody fragment that specifically bind to breast cancer cells.

40. The method of any one of claims 1 to 2 and 3 to 27, wherein the cell-binding agent is an anti-PSMA antibody, an anti-CanAg antibody, an anti-CD19 antibody, an anti-CD33 antibody, an anti-CALLA antibody, an anti-CD56 antibody, or an anti-IGF-IR antibody.

41. The method of any one of claims 1 to 2 and 3 to 27, wherein the cell-binding agent is a resurfaced or humanized My9-6 or N901 antibody or fragment thereof, wherein said My9-6 antibody comprises a heavy chain and a light chain, said heavy chain comprising three complementarity determining regions comprising HCCDR1, HCCDR2 and HCCDR3 of murine antibody My9-6, and wherein said light chain comprises three complementarity determining regions comprising LCCDR1, LCCDR2 and LCCDR3 of murine antibody My9-6; and wherein said resurfaced or humanized N901 antibody or fragment thereof comprises a heavy chain and a light chain, said heavy chain comprising three complementarity determining regions comprising HCCDR1, HCCDR2 and HCCDR3 of murine antibody N901, and said light chain comprising three complementarity determining regions comprising LCCDR1, LCCDR2 and LCCDR3 of murine antibody N901.

42. The method of any one of claims 1 to 2 and 3 to 27, wherein the cell-binding agent is a resurfaced or humanized B4 antibody, or a resurfaced or humanized C242 antibody or fragment thereof, wherein said resurfaced or humanized C242 antibody comprises a heavy chain and a light chain, said heavy chain comprising three complementarity determining regions comprising HCCDR1, HCCDR2 and HCCDR3 of murine antibody C242, and said light chain comprising three complementarity determining regions comprising LCCDR1, LCCDR2 and LCCDR3 of murine antibody C242.

43. The method of any one of claims 1 to 2 and 3 to 27, wherein the cell-binding agent is a resurfaced or humanized C242 antibody or fragment thereof, wherein said resurfaced or humanized C242 antibody comprises a heavy chain and a light chain, said heavy chain comprising three complementarity determining regions comprising HCCDR1, HCCDR2 and HCCDR3 of murine antibody C242, and said light chain comprising three complementarity determining regions comprising LCCDR1, LCCDR2 and LCCDR3 of murine antibody C242.

44. A method of eliminating cells in vivo, the method comprising contacting the cells in vivo with a cell-binding agent maytansinoid conjugate, wherein one or more maytansinoids is covalently linked to the cell-binding agent via a non-cleavable linker and the cell-binding agent binds to the cells,
wherein the cell-binding agent is an antibody, a single chain antibody or an antibody fragment that specifically binds to a target cell, wherein at least a constant region of the antibody, single chain antibody or antibody fragment comprises a human antibody sequence, and provided that the cell-binding agent is not an anti-erbB antibody.

45. A method of treatment of afflictions selected from the group consisting of tumors, autoimmune diseases, graft rejections, graft versus host disease, viral infections, and parasite infections, the method comprising administering to a subject in need of treatment an effective amount of a cell-binding agent maytansinoid conjugate, wherein one or more maytansinoids is covalently linked to the cell-binding agent via a non-cleavable linker and the cell-binding agent binds diseased or infected cells of the affliction,
wherein the cell-binding agent is an antibody, a single chain antibody or an antibody fragment that specifically binds to diseased or infected cells of the affliction, wherein at least a constant region of the antibody, single chain antibody or antibody fragment comprises a human antibody sequence, and provided that the cell-binding agent is not an anti-erbB antibody.

46. The method of claim 44, wherein the non-cleavable linker is substantially resistant to acid-induced cleavage, light-induced cleavage, peptidase-induced cleavage, esterase-induced cleavage, and disulfide bond cleavage.

47. The method of claim 44, wherein the non-cleavable linker has a sulfur atom.

48. The method of claim 47, wherein the non-cleavable linker is derived from a maleimido-based moiety.

49. The method of claim 48, wherein the non-cleavable linker is derived from a maleimido-based moiety selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidcaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI).

50. The method of claim 49, wherein the non-cleavable linker is derived from SMCC.

51. The method of claim 47, wherein the non-cleavable linker is derived from a haloacetyl-based moiety.

52. The method of claim 51, wherein the non-cleavable linker is derived from a haloacetyl-based moiety selected from the group consisting of N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

53. The method of claim 52, wherein the non-cleavable linker is derived from SIAB.

54. The method of claim 44, wherein the linker is at any one of the C-3 hydroxyl, C-14 hydroxymethyl, C-15 hydroxyl or C-20 desmethyl groups of the at least one maytansinoid.

55. The method of claim 44, wherein the at least one maytansinoid is an N-methyl-alanine-containing ester of maytansinol.

56. The method of claim 54, wherein the at least one maytansinoid is an N-methyl-cysteine-containing ester of maytansinol.

57. The method of claim 44, wherein the at least one maytansinoid is represented by formula (II'-L), (II'-D) or (II'-D,L):

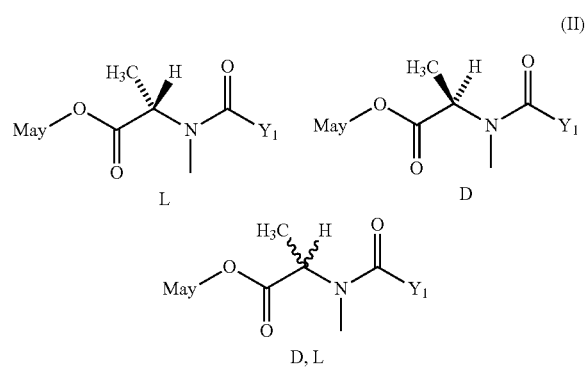

wherein:

$Y_1'$ represents $(CR_7R_8)_l(CR_9=CR_{10})_p(C\equiv C)_qA_o(CR_5R_6)_mD_u(CR_{11}=CR_{12})_r(C\equiv C)_sB_t(CR_3R_4)_nCR_1R_2S-$, wherein:

$R_1$ to $R_{12}$ are each independently linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition, $R_2$ to $R_{12}$ can be H;

A, B, and D, each independently is cyclic alkyl or cyclic alkenyl having 3 to 10 carbon atoms, simple or substituted aryl, or heterocyclic aromatic or heterocycloalkyl radical;

l, m, n, o, p, q, r, s, t and u are each independently 0 or an integer of 1 to 5, provided that at least two of l, m, n, o, p, q, r, s, t and u are not both zero; and May represents a maytansinoid that bears a side chain at C-3 hydroxyl, C-14 hydroxymethyl, C-15 hydroxyl or C-20 desmethyl.

58. The method of claim 57, wherein $R_1$ is methyl and $R_2$ is H or $R_1$ and $R_2$ are methyl.

59. The method of claim 57, wherein $R_1$ is methyl, $R_2$ is H, $R_5$, $R_6$, $R_7$ and $R_8$ are each H, l and m are each 1, and n is 0; or wherein $R_1$ and $R_2$ are methyl, $R_5$, $R_6$, $R_7$, $R_8$ are each H, l and m are 1, and n is 0.

60. The method of claim 44, wherein the at least one maytansinoid is represented by formula (II-L), (II-D), or (II-D,L):

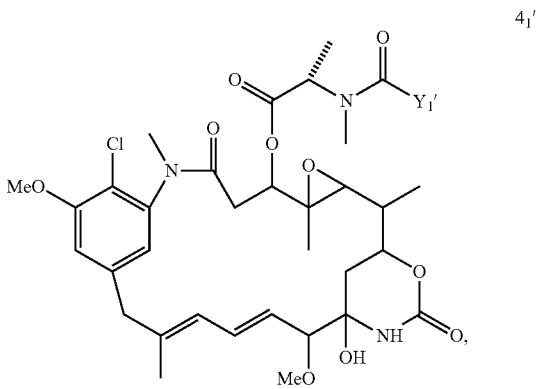

wherein:

$Y_1$ represents $(CR_7R_8)_l(CR_5R_6)_m(CR_3R_4)_nCR_1R_2S-$, wherein:

$R_1$ to $R_8$ are each independently, linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition $R_2$ to $R_8$ can be H;

l, m and n are each independently an integer of 1 to 5, and in addition n can be 0; and May represents a maytansinoid that bears the side chain at C-3 hydroxyl, C-14 hydroxymethyl, C-15 hydroxyl or C-20 desmethyl.

61. The method of claim 60, wherein $R_1$ is methyl and $R_2$ is H or $R_1$ and $R_2$ are methyl.

62. The method of claim 60, wherein $R_1$ is methyl, $R_2$ is H, $R_5$, $R_6$, $R_7$ and $R_8$ are each H, l and m are each 1, and n is 0; or wherein $R_1$ and $R_2$ are methyl, $R_5$, $R_6$, $R_7$, $R_8$ are each H, l and m are 1, and n is 0.

63. The method of claim 44, wherein the at least one maytansinoid is represented by formula $4_1'$:

wherein:

$Y_1'$ represents $(CR_7R_8)_l(CR_9=CR_{10})_p(C\equiv C)_qA_o(CR_5R_6)_mD_u(CR_{11}=CR_{12})_r(C\equiv C)_sB_t(CR_3R_4)_nCR_1R_2S—$, wherein:

$R_1$ to $R_{12}$ are each independently linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition, $R_2$ to $R_{12}$ can be H;

A, B, and D, each independently is cyclic alkyl or cyclic alkenyl having 3 to 10 carbon atoms, simple or substituted aryl, or heterocyclic aromatic or heterocycloalkyl radical; and l, m, n, o, p, q, r, s, t and u are each independently 0 or an integer of 1 to 5, provided that at least two of l, m, n, o, p, q, r, s, t and u are not both zero.

64. The method of claim 63, wherein $R_1$ is methyl and $R_2$ is H or $R_1$ and $R_2$ are methyl.

65. The method of claim 64, wherein $R_1$ is methyl, $R_2$ is H, $R_5$, $R_6$, $R_7$ and $R_8$ are each H, l and m are each 1, and n is 0; or wherein $R_1$ and $R_2$ are methyl, $R_5$, $R_6$, $R_7$, $R_8$ are each H, l and m are 1, and n is 0.

66. The method of claim 44, wherein the at least one maytansinoid is represented by formula $4_1$:

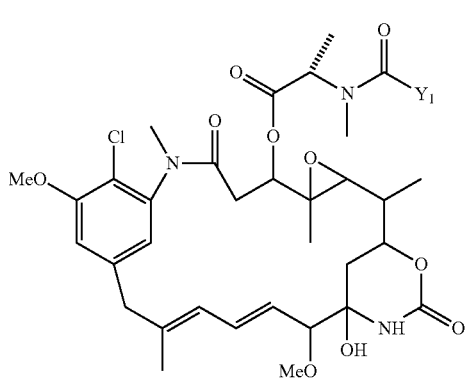

wherein:

$Y_1$ represents $(CR_7R_8)_l(CR_5R_6)_m(CR_3R_4)_nCR_1R_2S—$, wherein:

$R_1$ to $R_8$ are each independently, linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition $R_2$ to $R_8$ can be H; and l, m and n are each independently an integer of 1 to 5, and in addition n can be 0.

67. The method of claim 66, wherein $R_1$ is methyl and $R_2$ is H or $R_1$ and $R_2$ are methyl.

68. The method of claim 66, wherein $R_1$ is methyl, $R_2$ is H, $R_5$, $R_6$, $R_7$ and $R_8$ are each H, l and m are each 1, and n is 0; or wherein $R_1$ and $R_2$ are methyl, $R_5$, $R_6$, $R_7$, $R_8$ are each H, l and m are 1, and n is 0.

69. The method of claim 44, wherein the at least one maytansinoid is $N^{2'}$-deacetyl-$N^{2'}$-(3-mercapto-1-oxopropyl)-maytansine (DM1).

70. The method of claim 44, wherein the at least one maytansinoid is $N^{2'}$-deacetyl-$N^{2'}$-(4-mercapto-1-oxopentyl)-maytansine (DM3).

71. The method of claim 44, wherein the at least one maytansinoid is $N^{2'}$-deacetyl-$N^{2'}$-(4-methyl-4-mercapto-1-oxopentyl)-maytansine (DM4).

72. The method of claim 44, wherein the cell-binding agent binds to tumor cells; virus infected cells, microorganism infected cells, parasite infected cells, autoimmune cells, activated cells in graft rejection or graft vs. host disease, myeloid cells, activated T-cells, B cells, or melanocytes; cells expressing the CD33, CD19, CanAg, or CALLA antigens; or cells expressing insulin growth factor receptor or folate receptor.

73. The method of claim 44, wherein the cell-binding agent binds to breast cancer cells, kidney cancer cells, lung cancer cells, prostate cancer cells, ovarian cancer cells, colorectal cancer cells, gastric cancer cells, squamous cancer cells, small-cell lung cancer cells, non-small-cell lung cancer cells, pancreatic cancer cells, testicular cancer cells, neuroblastoma cells, melanoma cells, cells from cancer of the lymphatic organs or a combination thereof.

74. The method of claim 44, wherein the cell-binding agent is a resurfaced antibody, a resurfaced single chain antibody, or a resurfaced antibody fragment that specifically binds to a target cell.

75. The method of claim 44, wherein the cell-binding agent is a humanized antibody, a humanized single chain antibody, or a humanized antibody fragment that specifically binds to a target cell.

76. The method of claim 44, wherein the cell-binding agent is a resurfaced monoclonal antibody, a resurfaced single chain monoclonal antibody, or a resurfaced monoclonal antibody fragment that specifically bind to a target cell.

77. The method of claim 44, wherein the cell-binding agent is a humanized monoclonal antibody, a humanized single chain monoclonal antibody, or a humanized monoclonal antibody fragment that specifically bind to a target cell.

78. The method of claim 44, wherein the cell-binding agent is a resurfaced monoclonal antibody, a resurfaced single chain monoclonal antibody, or a resurfaced monoclonal antibody fragment that specifically bind to tumor cells.

79. The method of claim 44, wherein the cell-binding agent is a humanized monoclonal antibody, a humanized single chain monoclonal antibody, or a humanized monoclonal antibody fragment that specifically bind to tumor cells.

80. The method of claim 44, wherein the cell-binding agent is a resurfaced monoclonal antibody, a resurfaced single chain monoclonal antibody, or a resurfaced monoclonal antibody fragment that specifically bind to colorectal cancer cells or breast cancer cells.

81. The method of claim 44, wherein the cell-binding agent is a humanized monoclonal antibody, a humanized single chain monoclonal antibody, or a humanized monoclonal antibody fragment that specifically bind to colorectal cancer cells or breast cancer cells.

82. The method of claim 44, wherein the cell-binding agent is a resurfaced monoclonal antibody, a resurfaced single chain monoclonal antibody, or a resurfaced monoclonal antibody fragment that specifically bind to breast cancer cells.

83. The method of claim 44, wherein the cell-binding agent is a humanized monoclonal antibody, a humanized single chain monoclonal antibody, or a humanized monoclonal antibody fragment that specifically bind to breast cancer cells.

84. The method of claim 44, wherein the cell-binding agent is an anti-PSMA antibody, an anti-CanAg antibody, an anti-CD19 antibody, an anti-CD33 antibody, an anti-CALLA antibody, an anti-CD56 antibody, or an anti-IGF-IR antibody.

85. The method of claim 44, wherein the cell-binding agent is a resurfaced or humanized My9-6 or N901 antibody or fragment thereof, wherein said My9-6 antibody comprises a heavy chain and a light chain, said heavy chain comprising three complementarity determining regions comprising HCCDR1, HCCDR2 and HCCDR3 of murine antibody My9-

6, and wherein said light chain comprises three complementarity determining regions comprising LCCDR1, LCCDR2 and LCCDR3 of murine antibody My9-6; and wherein said resurfaced or humanized N901 antibody or fragment thereof comprises a heavy chain and a light chain, said heavy chain comprising three complementarity determining regions comprising HCCDR1, HCCDR2 and HCCDR3 of murine antibody N901, and said light chain comprising three complementarity determining regions comprising LCCDR1, LCCDR2 and LCCDR3 of murine antibody N901.

86. The method of claim 44, wherein the cell-binding agent is a resurfaced or humanized B4 antibody, or a resurfaced or humanized C242 antibody or fragment thereof, wherein said resurfaced or humanized C242 antibody comprises a heavy chain and a light chain, said heavy chain comprising three complementarity determining regions comprising HCCDR1, HCCDR2 and HCCDR3 of murine antibody C242, and said light chain comprising three complementarity determining regions comprising LCCDR1, LCCDR2 and LCCDR3 of murine antibody C242.

87. The method of claim 44, wherein the cell-binding agent is a humanized C242 antibody or fragment thereof, wherein said humanized C242 antibody comprises a heavy chain and a light chain, said heavy chain comprising three complementarity determining regions comprising HCCDR1, HCCDR2 and HCCDR3 of murine antibody C242, and said light chain comprising three complementarity determining regions comprising LCCDR1, LCCDR2 and LCCDR3 of murine antibody C242.

88. The method of claim 44, wherein the cell-binding agent is a resurfaced C242 antibody or fragment thereof, wherein said resurfaced or humanized C242 antibody comprises a heavy chain and a light chain, said heavy chain comprising three complementarity determining regions comprising HCCDR1, HCCDR2 and HCCDR3 of murine antibody C242, and said light chain comprising three complementarity determining regions comprising LCCDR1, LCCDR2 and LCCDR3 of murine antibody C242.

89. The method of claim 45, wherein the tumors are selected from the group consisting of lung cancer, breast cancer, colorectal cancer, gastric cancer, squamous cell cancer, small-cell lung cancer, non-small-cell lung cancer cells, pancreatic cancer cells, testicular cancer, neuroblastoma cells, prostate cancer, kidney cancer, cancer of the pancreas, cancer of the ovary and cancer of the lymphatic organs.

90. The method of claim 45, wherein the non-cleavable linker is substantially resistant to acid-induced cleavage, light-induced cleavage, peptidase-induced cleavage, esterase-induced cleavage, and disulfide bond cleavage.

91. The method of claim 45, wherein the non-cleavable linker has a sulfur atom.

92. The method of claim 91, wherein the non-cleavable linker is derived from a maleimido-based moiety.

93. The method of claim 92, wherein the non-cleavable linker is derived from a maleimido-based moiety selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), E-maleimidcaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI).

94. The method of claim 93, wherein the non-cleavable linker is derived from SMCC.

95. The method of claim 91, wherein the non-cleavable linker is derived from a haloacetyl-based moiety.

96. The method of claim 95, wherein the non-cleavable linker is derived from a haloacetyl-based moiety selected from the group consisting of N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

97. The method of claim 96, wherein the non-cleavable linker is derived from SIAB.

98. The method of claim 45, wherein the linker is at any one of the C-3 hydroxyl, C-14 hydroxymethyl, C-15 hydroxyl or C-20 desmethyl groups of the at least one maytansinoid.

99. The method of claim 45, wherein the at least one maytansinoid is an N-methyl-alanine-containing ester of maytansinol.

100. The method of claim 45, wherein the at least one maytansinoid is an N-methyl-cysteine-containing ester of maytansinol.

101. The method of claim 45, wherein the at least one maytansinoid is represented by formula (II'-L), (II'-D) or (II'-D,L):

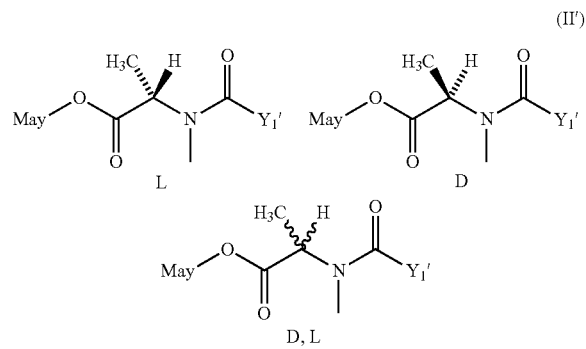

wherein:
$Y_1'$ represents $(CR_7R_8)_l(CR_9=CR_{10})_p(C\equiv C)_qA_o(CR_5R_6)_mD_u(CR_{11}=CR_{12})_r(C\equiv C)_sB_t(CR_3R_4)_nCR_1R_2S-$,
wherein:
$R_1$ to $R_{12}$ are each independently linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition, $R_2$ to $R_{12}$ can be H;
A, B, and D, each independently is cyclic alkyl or cyclic alkenyl having 3 to 10 carbon atoms, simple or substituted aryl, or heterocyclic aromatic or heterocycloalkyl radical;
l, m, n, o, p, q, r, s, t and u are each independently 0 or an integer of 1 to 5, provided that at least two of l, m, n, o, p, q, r, s, t and u are not both zero; and
May represents a maytansinoid that bears a side chain at C-3 hydroxyl, C-14 hydroxymethyl, C-15 hydroxyl or C-20 desmethyl.

102. The method of claim 101, wherein $R_1$ is methyl and $R_2$ is H or $R_1$ and $R_2$ are methyl.

103. The method of claim 101, wherein $R_1$ is methyl, $R_2$ is H, $R_5$, $R_6$, $R_7$ and $R_8$ are each H, l and m are each 1, and n is 0; or wherein $R_1$ and $R_2$ are methyl, $R_5$, $R_6$, $R_7$, $R_8$ are each H, l and m are 1, and n is 0.

104. The method of claim 45, wherein the at least one maytansinoid is represented by formula (II-L), (II-D), or (II-D,L):

$$(II)$$

wherein:
Y$_1$ represents (CR$_7$R$_8$)$_l$(CR$_5$R$_6$)$_m$(CR$_3$R$_4$)$_n$CR$_1$R$_2$S—, wherein:
R$_1$ to R$_8$ are each independently, linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition R$_2$ to R$_8$ can be H;
l, m and n are each independently an integer of 1 to 5, and in addition n can be 0; and
May represents a maytansinoid that bears the side chain at C-3 hydroxyl, C-14 hydroxymethyl, C-15 hydroxyl or C-20 desmethyl.

105. The method of claim 104, wherein R$_1$ is methyl and R$_2$ is H or R$_1$ and R$_2$ are methyl.

106. The method of claim 104, wherein R$_1$ is methyl, R$_2$ is H, R$_5$, R$_6$, R$_7$ and R$_8$ are each H, l and m are each 1, and n is 0; or wherein R$_1$ and R$_2$ are methyl, R$_5$, R$_6$, R$_7$, R$_8$ are each H, l and m are 1, and n is 0.

107. The method of claim 45, wherein the at least one maytansinoid is represented by formula 4$_1$':

$$4_1'$$

wherein:
Y$_1$' represents (CR$_7$R$_8$)$_l$(CR$_9$=CR$_{10}$)$_p$(C≡C)$_q$A$_o$ (CR$_5$R$_6$)$_m$D$_u$(CR$_{11}$=CR$_{12}$)$_r$(C≡C)$_s$B$_t$(CR$_3$R$_4$)$_n$CR$_1$R$_2$S—,
wherein:
R$_1$ to R$_{12}$ are each independently linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition, R$_2$ to R$_{12}$ can be H;
A, B, and D, each independently is cyclic alkyl or cyclic alkenyl having 3 to 10 carbon atoms, simple or substituted aryl, or heterocyclic aromatic or heterocycloalkyl radical; and
l, m, n, o, p, q, r, s, t and u are each independently 0 or an integer of 1 to 5, provided that at least two of l, m, n, o, p, q, r, s, t and u are not both zero.

108. The method of claim 107, wherein R$_1$ is methyl and R$_2$ is H or R$_1$ and R$_2$ are methyl.

109. The method of claim 107, wherein R$_1$ is methyl, R$_2$ is H, R$_5$, R$_6$, R$_7$ and R$_8$ are each H, l and m are each 1, and n is 0; or wherein R$_1$ and R$_2$ are methyl, R$_5$, R$_6$, R$_7$, R$_8$ are each H, l and m are 1, and n is 0.

110. The method of claim 45, wherein the at least one maytansinoid is represented by formula 4$_1$:

$$4_1$$

wherein:
Y$_1$ represents (CR$_7$R$_8$)$_l$(CR$_5$R$_6$)$_m$(CR$_3$R$_4$)$_n$CR$_1$R$_2$S—, wherein:
R$_1$ to R$_8$ are each independently, linear alkyl or alkenyl having 1 to 10 carbon atoms, branched or cyclic alkyl or alkenyl having 3 to 10 carbon atoms, phenyl, substituted phenyl or heterocyclic aromatic or heterocycloalkyl radical, and in addition R$_2$ to R$_8$ can be H; and
l, m and n are each independently an integer of 1 to 5, and in addition n can be 0.

111. The method of claim 110, wherein R$_1$ is methyl and R$_2$ is H or R$_1$ and R$_2$ are methyl.

112. The method of claim 110, wherein R$_1$ is methyl, R$_2$ is H, R$_5$, R$_6$, R$_7$ and R$_8$ are each H, l and m are each 1, and n is 0; or wherein R$_1$ and R$_2$ are methyl, R$_5$, R$_6$, R$_7$, R$_8$ are each H, l and m are 1, and n is 0.

113. The method of claim 45, wherein the at least one maytansinoid is N$^{2'}$-deacetyl-N$^{2'}$-(3-mercapto-1-oxopropyl)-maytansine (DM1).

114. The method of claim 45, wherein the at least one maytansinoid is N$^{2'}$-deacetyl-N$^{2'}$-(4-mercapto-1-oxopentyl)-maytansine (DM3).

115. The method of claim 45, wherein the at least one maytansinoid is N$^{2'}$-deacetyl-N$^{2'}$-(4-methyl-4-mercapto-1-oxopentyl)-maytansine (DM4).

116. The method of claim 45, wherein the cell-binding agent is said resurfaced antibody, said resurfaced single chain antibody, or said resurfaced antibody fragment that specifically bind to diseased or infected cells of the affliction.

117. The method of claim 45, wherein the cell-binding agent is said humanized antibody, said humanized single chain antibody, or said humanized antibody fragment that specifically bind to diseased or infected cells of the affliction.

118. The method of claim 45, wherein the cell-binding agent is a resurfaced monoclonal antibody, a resurfaced single chain monoclonal antibody, or a resurfaced monoclonal antibody fragment that specifically bind to diseased or infected cells of the affliction.

119. The method of claim 45, wherein the cell-binding agent is a humanized monoclonal antibody, a humanized single chain monoclonal antibody, or a humanized monoclonal antibody fragment that specifically bind to diseased or infected cells of the affliction.

120. The method of claim 45, wherein the cell-binding agent is an anti-PSMA antibody, an anti-CanAg antibody, an anti-CD19 antibody, an anti-CD33 antibody, an anti-CALLA antibody, an anti-CD56 antibody, or an anti-IGF-IR antibody.

121. The method of claim 45, wherein the cell-binding agent is a resurfaced or humanized My9-6 or N901 antibody or fragment thereof, wherein said My9-6 antibody comprises a heavy chain and a light chain, said heavy chain comprising three complementarity determining regions comprising HCCDR1, HCCDR2 and HCCDR3 of murine antibody My9-6, and wherein said light chain comprises three complementarity determining regions comprising LCCDR1, LCCDR2 and LCCDR3 of murine antibody My9-6; and wherein said resurfaced or humanized N901 antibody or fragment thereof comprises a heavy chain and a light chain, said heavy chain comprising three complementarity determining regions comprising HCCDR1, HCCDR2 and HCCDR3 of murine antibody N901, and said light chain comprising three complementarity determining regions comprising LCCDR1, LCCDR2 and LCCDR3 of murine antibody N901.

122. The method of claim 45, wherein the cell-binding agent is a resurfaced or humanized B4 antibody, or a resurfaced or humanized C242 antibody or fragment thereof, wherein said resurfaced or humanized C242 antibody comprises a heavy chain and a light chain, said heavy chain comprising three complementarity determining regions comprising HCCDR1, HCCDR2 and HCCDR3 of murine antibody C242, and said light chain comprising three complementarity determining regions comprising LCCDR1, LCCDR2 and LCCDR3 of murine antibody C242.

123. The method of claim 45, wherein the cell-binding agent is a humanized C242 antibody or fragment thereof, wherein said humanized C242 antibody comprises a heavy chain and a light chain, said heavy chain comprising three complementarity determining regions comprising HCCDR1, HCCDR2 and HCCDR3 of murine antibody C242, and said light chain comprising three complementarity determining regions comprising LCCDR1, LCCDR2 and LCCDR3 of murine antibody C242.

124. The method of claim 45, wherein the cell-binding agent is a resurfaced C242 antibody or fragment thereof, wherein said resurfaced C242 antibody comprises a heavy chain and a light chain, said heavy chain comprising three complementarity determining regions comprising HCCDR1, HCCDR2 and HCCDR3 of murine antibody C242, and said light chain comprising three complementarity determining regions comprising LCCDR1, LCCDR2 and LCCDR3 of murine antibody C242.

125. The method of claim 1, wherein an average of 1 to about 10 maytansinoids is covalently linked to the cell-binding agent.

126. The method of claim 1, wherein the cell-binding agent is a fully human antibody, a fully human single chain antibody, or a fully human antibody fragment that specifically bind to a target cell.

127. The method of claim 1, wherein the cell-binding agent is a fully human antibody, a fully human single chain antibody, or a fully human antibody fragment that specifically bind to tumor cells.

128. The method of claim 1, wherein the cell-binding agent is a fully human antibody, a fully human single chain antibody, or a fully human antibody fragment, the maytansinoid is $N^{2'}$-deacetyl-$N^{2'}$-(3-mercapto-1-oxopropyl)-maytansine (DM1) and the linker is derived from SMCC.

129. The method of claim 1, wherein the cell-binding agent is a resurfaced antibody, a resurfaced single chain antibody or a resurfaced antibody fragment that specifically bind to target cells, the maytansinoid is $N^{2'}$-deacetyl-$N^{2'}$-(3-mercapto-1-oxopropyl)-maytansine (DM1) and the linker is derived from SMCC.

130. The method of claim 1, wherein the cell-binding agent is a humanized antibody, a humanized single chain antibody or a humanized antibody fragment that specifically bind to target cells, the maytansinoid is $N^{2'}$-deacetyl-$N^{2'}$-(3-mercapto-1-oxopropyl)-maytansine (DM1) and the linker is derived from SMCC.

131. The method of claim 44, wherein an average of 1 to about 10 maytansinoids is covalently linked to the cell-binding agent.

132. The method of claim 44, wherein the cell-binding agent is a fully human antibody, a fully human single chain antibody, or a fully human antibody fragment that specifically bind to a target cell.

133. The method of claim 44, wherein the cell-binding agent is a fully human antibody, a fully human single chain antibody, or a fully human antibody fragment that specifically bind to tumor cells.

134. The method of claim 44, wherein the cell-binding agent is a fully human antibody, a fully human single chain antibody, or a fully human antibody fragment, the maytansinoid is $N^{2'}$-deacetyl-$N^{2'}$-(3-mercapto-1-oxopropyl)-maytansine (DM1) and the linker is derived from SMCC.

135. The method of claim 44, wherein the cell-binding agent is a resurfaced antibody, a resurfaced single chain antibody or a resurfaced antibody fragment that specifically bind to target cells, the maytansinoid is $N^{2'}$-deacetyl-$N^{2'}$-(3-mercapto-1-oxopropyl)-maytansine (DM1) and the linker is derived from SMCC.

136. The method of claim 44, wherein the cell-binding agent is a humanized antibody, a humanized single chain antibody or a humanized antibody fragment that specifically bind to target cells, the maytansinoid is $N^{2'}$-deacetyl-$N^{2'}$-(3-mercapto-1-oxopropyl)-maytansine (DM1) and the linker is derived from SMCC.

137. The method of claim 45, wherein an average of 1 to about 10 maytansinoids is covalently linked to the cell-binding agent.

138. The method of claim 45, wherein the cell-binding agent is a fully human antibody, a fully human single chain antibody, or a fully human antibody fragment that specifically bind to diseased or infected cells of the affliction.

139. The method of claim 45, wherein the cell-binding agent is a fully human antibody, a fully human single chain antibody, or a fully human antibody fragment, the maytansinoid is $N^{2'}$-deacetyl-$N^{2'}$-(3-mercapto-1-oxopropyl)-maytansine (DM1) and the linker is derived from SMCC.

140. The method of claim 45, wherein the cell-binding agent is a resurfaced antibody, a resurfaced single chain antibody or a resurfaced antibody fragment that specifically bind to target cells, the maytansinoid is $N^{2'}$-deacetyl-$N^{2'}$-(3-mercapto-1-oxopropyl)-maytansine (DM1) and the linker is derived from SMCC.

141. The method of claim 45, wherein the cell-binding agent is a humanized antibody, a humanized single chain antibody or a humanized antibody fragment that specifically bind to target cells, the maytansinoid is $N^{2'}$-deacetyl-$N^{2'}$-(3-mercapto-1-oxopropyl)-maytansine (DM1) and the linker is derived from SMCC.

142. The method of claim 1, wherein the cell-binding agent is a fully human antibody, a fully human single chain antibody, or a fully human antibody fragment that specifically bind to colorectal cancer cells, breast cancer cells, kidney cancer cells, lung cancer cells, prostate cancer cells, ovarian cancer cells, gastric cancer cells, squamous cancer cells, small-cell lung cancer cells, non-small-cell lung cancer cells, pancreatic cancer cells, testicular cancer cells, neuroblastoma cells, melanoma cells, cells from cancer of the lymphatic organs or a combination thereof.

143. The method of claim 1, wherein the cell-binding agent is a fully human antibody, a fully human single chain antibody, or a fully human antibody fragment that specifically bind to colorectal cancer cells, breast cancer cells, kidney cancer cells, lung cancer cells, prostate cancer cells, ovarian cancer cells, gastric cancer cells, squamous cancer cells, small-cell lung cancer cells, non-small-cell lung cancer cells, pancreatic cancer cells, testicular cancer cells, neuroblastoma cells, melanoma cells, cells from cancer of the lymphatic organs or a combination thereof.

\* \* \* \* \*

UNITED STATES PATENT AND TRADEMARK OFFICE
CERTIFICATE OF CORRECTION

| | | |
|---|---|---|
| PATENT NO. | : 8,088,387 B2 | Page 1 of 1 |
| APPLICATION NO. | : 10/960602 | |
| DATED | : January 3, 2012 | |
| INVENTOR(S) | : Rita Steeves et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1468 days.

In claim 18 at column 33, line 20:
Delete "41'" and insert -- $4_1'$ --

In claim 22 at column 33, line 67:
Delete "41" and insert -- $4_1'$ --

In claim 31 at column 34, line 66:
Delete "binds" and insert -- bind --

Signed and Sealed this
Eighth Day of May, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,088,387 B2 | |
| APPLICATION NO. | : 10/960602 | |
| DATED | : January 3, 2012 | |
| INVENTOR(S) | : Rita Steeves et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1468 days.

In claim 18 at column 33, line 20:
Delete "41'" and insert -- $4_1'$ --

In claim 22 at column 33, line 67:
Delete "41" and insert -- $4_1'$ --

In claim 31 at column 34, line 66:
Delete "binds" and insert -- bind --

In claim 74 at column 40, line 18:
Delete "binds" and insert -- bind --

In claim 75 at column 40, line 22:
Delete "binds" and insert -- bind --

In claim 143 at column 48, line 6:
Delete "colorectal cancer cells, breast cancer cells, kidney" and insert -- breast cancer cells. --

In claim 143 at column 48, lines 7-12:
Delete "cancer cells, lung cancer cells, prostate cancer cells, ovarian cancer cells, gastric cancer cells, sqamous cancer cells, small-cell lung cancer cells, non-small-cell lung cancer cells, pancreatic cancer cells, testicular cancer cells, neuroblastoma cells, melanoma cells, cells from cancer of the lymphatic organs or a combination thereof."

This certificate supersedes the Certificate of Correction issued May 8, 2012.

Signed and Sealed this
Nineteenth Day of June, 2012

David J. Kappos
*Director of the United States Patent and Trademark Office*